United States Patent
De La Cruz et al.

(10) Patent No.: US 9,181,215 B2
(45) Date of Patent: Nov. 10, 2015

(54) MANUFACTURING PROCESS FOR PYRIMIDINE DERIVATIVES

(75) Inventors: Marilyn De La Cruz, Matawan, NJ (US); Piotr H. Karpinski, Lincoln Park, NJ (US); Liladhar Murlidhar Waykole, Succasunna, NJ (US)

(73) Assignee: Novartis AG, Basel (CH)

( * ) Notice: Subject to any disclaimer, the term of this patent is extended or adjusted under 35 U.S.C. 154(b) by 169 days.

(21) Appl. No.: 13/825,880

(22) PCT Filed: Sep. 29, 2011

(86) PCT No.: PCT/US2011/053808
§ 371 (c)(1),
(2), (4) Date: Mar. 25, 2013

(87) PCT Pub. No.: WO2012/044727
PCT Pub. Date: Apr. 5, 2012

(65) Prior Publication Data
US 2013/0225571 A1    Aug. 29, 2013

Related U.S. Application Data

(60) Provisional application No. 61/388,721, filed on Oct. 1, 2010, provisional application No. 61/494,915, filed on Jun. 9, 2011.

(51) Int. Cl.
| | |
|---|---|
| *A61K 31/535* | (2006.01) |
| *C07D 413/14* | (2006.01) |
| *C07D 401/04* | (2006.01) |
| *C07F 5/04* | (2006.01) |
| *C07F 5/02* | (2006.01) |

(52) U.S. Cl.
CPC ............ *C07D 401/04* (2013.01); *A61K 31/535* (2013.01); *C07D 413/14* (2013.01); *C07F 5/025* (2013.01); *C07F 5/04* (2013.01)

(58) Field of Classification Search
CPC ............................ A61K 31/535; C07D 413/14
See application file for complete search history.

(56) References Cited

FOREIGN PATENT DOCUMENTS

| | | |
|---|---|---|
| WO | 2004/048365 A1 | 6/2004 |
| WO | 2007/084786 A1 | 7/2007 |
| WO | 2008/023159 A1 | 2/2008 |
| WO | 2009/066084 A1 | 5/2009 |
| WO | 2010/130779 A2 | 11/2010 |

OTHER PUBLICATIONS

Caira, Mino, Crystalline Polymorphism of Organic Compounds, Topics in Currently Chemistry, vol. 198, 1998.
H.G. Brittain, "Polymorphism in Pharmaceutical solids", p. 236, Marcel Dekker(1999).
Notification No. 568 of the Evaluation and Licensing Division PMSB—Specifications and Test Method of New Drugs, May 1, 2001.
Kawaguchi, Yoko et al: "Drug and crystal polymorphism", Journal of Human Environmental Engineering, vol. 4, No. 2, pp. 310-317 (2002).
Chapter 8, Section 1, Case of Pseudopolymorph, Science of Polymorphison Phenomena and Crystallization of Pharmaceuticals Products, pp. 273, 278, 305-317, Nakajima Printing Kabushiki Kaisha, Sep. 20, 2002.

*Primary Examiner* — Rebecca Anderson
(74) *Attorney, Agent, or Firm* — Sandra Rueck

(57) ABSTRACT

The invention relates to new crystalline forms of processes for manufacturing a compound of formula 5,

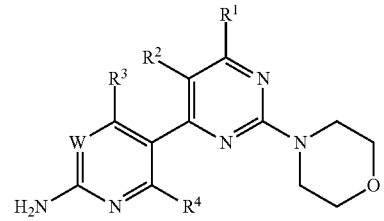

or a stereoisomer, tautomer or a salt thereof, wherein the substituents are as defined in the specification. The invention further relates to new manufacturing processes for specific solid forms of Compound A and its salts, to such solid forms and to use of said solid forms for the therapeutic treatment of warm-blooded animals.

13 Claims, 14 Drawing Sheets

MANUFACTURING PROCESS FOR PYRIMIDINE DERIVATIVES

FIELD OF THE INVENTION

The present invention relates to new manufacturing processes for pyrimidine derivatives, to intermediates thereof and to the manufacturing of intermediates. The present invention further relates to a new manufacturing process for specific solid forms of pyrimidine derivative 5-(2,6-Di-4-morpholinyl-4-pyrimidinyl)-4-trifluoromethylpyridin-2-amine (Compound A, see below), its hydrates, its salts and hydrates and solvates of its salts, to said specific solid forms thereof, to pharmaceutical compositions containing said solid forms, to processes for the preparation of pharmaceutical compositions containing said solid forms, to methods of using said solid forms and to pharmaceutical compositions for the therapeutic treatment of warm-blooded animals, especially humans.

BACKGROUND OF THE INVENTION

WO 2007/084786 (priority date: Jan. 20, 2006) describes certain pyrimidine derivatives having PI3K inhibiting properties, their use as pharmaceuticals and manufacturing processes thereof. One pyrimidine derivative disclosed in WO 2007/084786 is the selective phosphatidylinositol 3-kinase inhibitor compound 5-(2,6-Di-4-morpholinyl-4-pyrimidinyl)-4-trifluoromethylpyridin-2-amine, hereinafter referred to as "Compound A" or "the compound of formula A".

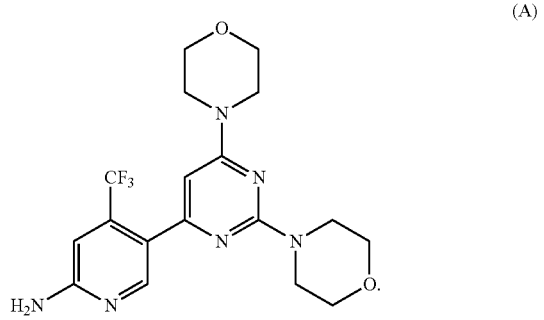 [SMILES: Nc1cc(C(F)(F)F)c(-c2cc(N3CCOCC3)nc(N3CCOCC3)n2)cn1]

(A)

Compound A is described in WO 2007/084786 in free form and as the hydrochloric acid salt. The manufacturing process for preparing Compound A is described in Example 10 of this document. The manufacturing processes described therein are, although suitable, regarded as disadvantageous for commercial production.

Due to the high potency of pyrimidine derivatives, in particular PI3K inhibitors, there is a need for improved manufacturing methods of such compounds. In particular there is a need to provide processes that fulfill one or more of the following criteria: scalable, safer; simpler; higher yielding and more economical when compared to known.

There also remains a need for new solid forms for the treatment of cancer.

SUMMARY OF THE INVENTION

Accordingly, the invention thus provides improved methods for manufacturing pyrimidine derivatives of formula 5, new intermediates useful in such processes and methods for manufacturing such intermediates.

Thus, in one aspect, the invention relates to a process for manufacturing a compound of formula 5,

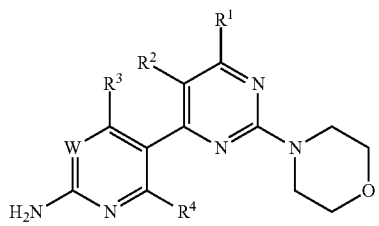

5 or a stereoisomer, tautomer, or a salt thereof, wherein,
W is $CR_W$ or N, wherein $R_w$ is selected from the group consisting of (1) hydrogen, (2) cyano, (3) halogen, (4) methyl, (5) trifluoromethyl, (6) sulfonamido;
$R^1$ is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —$COR_{1a}$, (13) —$CO_2R_{1a}$, (14) —$CONR_{1a}R_{1b}$, (15) —$NR_{1a}R_{1b}$ (17) —$NR_{1a}SO_2R_{1b}$, (18) —$OCOR_{1a}$, (19) —$OR_{1a}$, (21) —$SOR_{1a}$, wherein $R_{1a}$ and $R_{1b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl;
$R^2$ is selected from the group consisting (1) hydrogen, (2) cyano, (3) nitro, (4) halogen, (5) hydroxy, (6) amino, (7) substituted and unsubstituted alkyl, (8) —$COR_{2a}$, and (9) —$NR_{2a}COR_{2b}$, wherein $R_{2a}$ and $R_{2b}$ are independently selected from the group consisting of (a) hydrogen, and (b) substituted or unsubstituted alkyl;
$R^3$ is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, 11) substituted and unsubstituted cycloalkyl, (12) —$COR_{3a}$, (13) —$NR_{3a}R_{3b}$, (14) —$NR_{3a}COR_{3b}$, (15) —$NR_{3a}SO_2R_{3b}$; (16) —$OR_{3a}$ (17) —$SR_{3a}$, (18) —$SOR_{3a}$, (19) —$SO_2R_{3a}$, and wherein $R_{3a}$, and $R_{3b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl; and
$R^4$ is selected from the group consisting of (1) hydrogen, and (2) halogen.

This process ("process step c") comprises the step of reacting a compound of formula 4

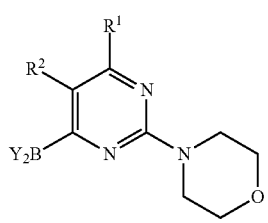

4 wherein $Y_2B$— represents an acyclic boronic acid, an acyclic boronic ester, or a cyclic boronic ester, preferably an acyclic or cyclic boronic ester, $R^1$ and $R^2$ are as defined for formula 5, with a compound of formula 4a

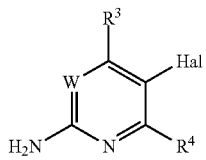

4a wherein Hal represents halogen, W, $R^3$ and $R^4$ are as defined for a compound of formula 5 under Suzuki conditions to obtain a compound of formula 5.

Optionally, process step c) may be followed by one or more a salt forming reactions (i.e., process step d). Thus, this process step c) may be combined with process step d) as described below. Alternatively or additionally, process step c) may be combined with process step b) or process steps a) and b). Thus, the invention provides processes for manufacturing compound 5 comprising process step c) or process steps b) and c) or process steps a), b) and c), in each case optionally followed by process step d). By combination of processes is meant that the starting material is obtained by applying the preceeding process, e.g., as outlined in FIG. 1. Such starting material my by employed directly (i.e., without isolation and/or purification) or after appropriate work-up steps. All such alternatives are encompassed by the present invention.

It was found that the process as described herein (also including the particular process steps) fulfills one or more of the following criteria: safer; simpler; higher yielding and more economical when compared to known processes for manufacturing compounds of formula 5. Further, the process as described herein is considered scalable, making it suitable for commercial production.

In another aspect, the invention relates to a process for manufacturing a compound of formula 4

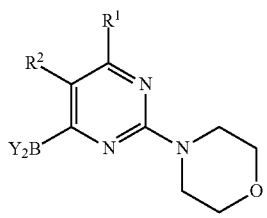

4 wherein
$Y_2B$— represents a boronic ester;
$R^1$ is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —$COR_{1a}$, (13) —$CO_2R_{1a}$, (14) —$CONR_{1a}R_{1b}$, (15) —$NR_{1a}R_{1b}$ (17) —$NR_{1a}SO_2R_{1b}$, (18) —$OCOR_{1a}$, (19) —$OR_{1a}$, (21) —$SOR_{1a}$, wherein $R_{1a}$ and $R_{1b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl;
$R^2$ is selected from the group consisting (1) hydrogen, (2) cyano, (3) nitro, (4) halogen, (5) hydroxy, (6) amino, (7) substituted and unsubstituted alkyl, (8) —$COR_{2a}$, and (9) —$NR_{2a}COR_{2b}$, wherein $R_{2a}$ and $R_{2b}$ are independently selected from the group consisting of (a) hydrogen, and (b) substituted or unsubstituted alkyl.

This process ("process step b") comprises the step of reacting a compound of formula 3

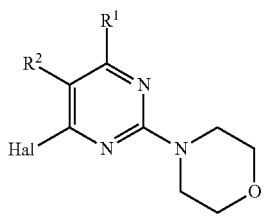

3 wherein
$R^1$ is as defined for a compound of formula 5,
$R^2$ is as defined for a compound of formula 5, and
Hal represents halogen,
with a boronic ester or derivative thereof of the formula 6

6 wherein
$Y_2B$ represents a boronic ester,
X represents hydrogen, hydroxyl, $C_1$-$C_4$ alkoxy or $Y_2B$, preferably $Y_2B$,
optionally in the presence of a catalyst, such as $Pd_2(dba)_3$/$PCy_3$, optionally in the presence of a diluent, optionally in the presence of a reaction aid, to obtain a compound of formula 4.

In yet another aspect, the invention relates to a process for manufacturing a compound of formula 3

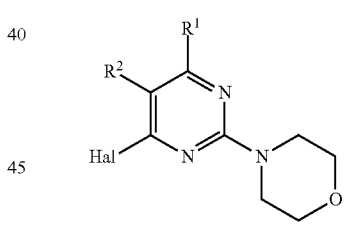

3 wherein
$R^1$ is a substituted or unsubstituted heterocycle,
$R^2$ is as defined for a compound of formula 5,
Hal represents halogen.

This process ("process step a") comprises the step of reacting a compound of formula 1

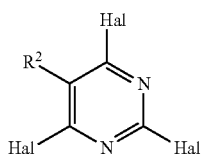

1 wherein
$R^2$ is as defined for a compound of formula 5,
Hal represents halogen, with a compound of the formula 2 or a mixture of different compounds of formula 2

   2 wherein $R^1$ is a substituted or unsubstituted heterocyclyl or a mixture thereof, under biphasic conditions, optionally in the presence of a reaction aid, optionally in the presence of a diluent, optionally followed by work-up and/or isolation steps.

In still another aspect, the invention relates to a compound of formula 4

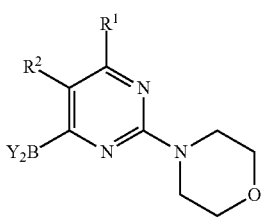   4 or a stereoisomer, tautomer, or a salt thereof, wherein
$R^1$ is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —$COR_{1a}$, (13) —$CO_2R_{1a}$, (14) —$CONR_{1a}R_{1b}$, (15) —$NR_{1a}R_{1b}$ (17) —$NR_{1a}SO_2R_{1b}$, (18) —$OCOR_{1a}$, (19) —$OR_{1a}$, (21) —$SOR_{1a}$, wherein $R_{1a}$, and $R_{1b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl;
$R^2$ is selected from the group consisting (1) hydrogen, (2) cyano, (3) nitro, (4) halogen, (5) hydroxy, (6) amino, (7) substituted and unsubstituted alkyl, (8) —$COR_{2a}$, and (9) —$NR_{2a}COR_{2b}$, wherein $R_{2a}$, and $R_{2b}$ are independently selected from the group consisting of (a) hydrogen, and (b) substituted or unsubstituted alkyl;
$Y_2B$ represents a boronic ester.

In another aspect, the invention relates to salt-forming reactions for manufacturing a compound of formula 5a:

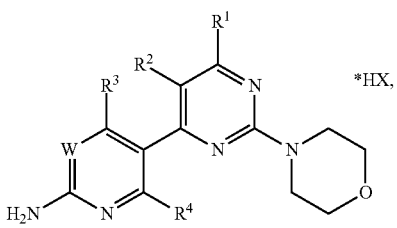   5a wherein
W, $R^1$, $R^2$, $R^3$ and $R^4$ are as defined for a compound of formula 5, and
HX is an acidic compound for formation of an acid addition salt.

In one aspect, provided herein is another process for manufacturing a compound of formula 5,

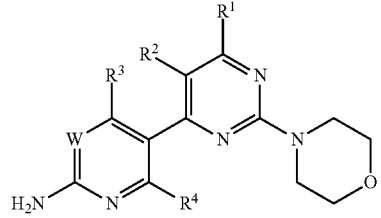   5 or a stereoisomer, tautomer, or a salt thereof, wherein,
W, $R^1$, $R^2$, $R^3$ and $R^4$ are as defined above for a compound of formula 5;
comprising the step of reacting a compound of formula 3

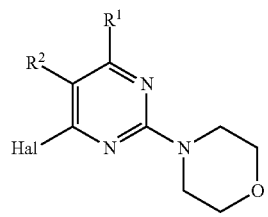   3 wherein Hal represents halogen and $R^1$ and $R^2$ are as defined for a compound of formula 5;
with a compound of formula B3

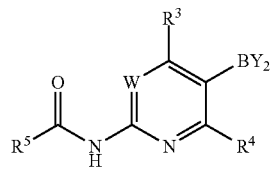   B3 wherein —$BY_2$ represents a boronic acid, an acyclic boronic ester, a cyclic boronic ester, or a trifluoroborate salt, and W, $R^3$ and $R^4$ are as defined for a compound of formula 5; and wherein $R^5$ is selected from the group consisting of (1) hydrogen, (2) substituted or unsubstituted alkyl, (3) substituted or unsubstituted alkyloxy, (4) substituted or unsubstituted aryl, (5) substituted or unsubstituted aryloxy, (6) substituted or unsubstituted arylalkyloxy; under Suzuki conditions, and followed by removal of the $R^5C(O)$— moiety, to obtain a compound of formula 5;
optionally followed by a salt forming reaction.

In another aspect, the invention also provides a compound of formula B3

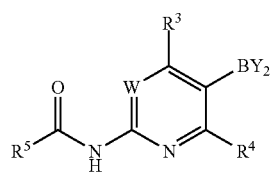   B3 or a stereoisomer, tautomer, or a salt thereof, wherein W, $R^3$, $R^4$, and $R^5$ are as defined above and $BY_2$ represents a boronic acid, an acyclic boronic ester, a cyclic boronic ester, or a trifluoroborate salt.

In yet another aspect, the invention also provides a process for manufacturing a compound of formula 5,

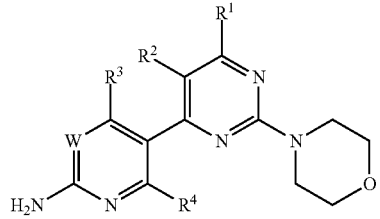

or a stereoisomer, tautomer, or a salt thereof, comprising one or more of the following steps:

Step A: contacting a compound of formula B1

<pre>
                R³
                 \
                  W       Hal
                  ‖
          H₂N─N       R⁴
</pre> with a reaction mixture comprising a solvent and an acid anhydride $(R^5C=O)_2O$, such that a compound of formula B2 is produced

B2

<pre>
                    R³
                     \
            O         W    Hal;
            ‖         ‖
      R⁵─C─N─H   N    R⁴
</pre>

Step B: i) contacting a compound of formula B2 with a reaction mixture comprising a first solvent, a first base and optionally an alcohol additive, ii) contacting the mixture of step (i) with a second solvent and a second base, iii) contacting the mixture of step (ii) with a boric acid derivative, iv) optionally contacting the mixture of step (iii) with a third solvent and a third base and then contacting the resulting mixture with a boric acid derivative, and v) optionally contacting the mixture of step (iii) or step (iv) with water and acid, such that a compound of formula B3 is produced:

B3

<pre>
                   R³
                    \
           O         W    BY₂;
           ‖         ‖
     R⁵─C─N─H   N    R⁴
</pre>

Step C: contacting a compound of formula B3 with a reaction mixture comprising a solvent, a base, a catalyst, and a compound of formula 3

3

<pre>
                R¹
          R²    |
           \    N
            \   ‖
     Hal─────N─N─O
                   \_/
</pre> such that a compound of B5 is produced

B5

<pre>
              R¹
        R²    |
     R³ \    N
         W   ‖
    O    ‖   N
    ‖    N───N─O
  R⁵─C─N     R⁴ \_/
       H
</pre>

Step D: contacting a compound of formula B5 with a reaction mixture comprising a solvent and a reagent for the removal of the $R^5C(=O)$— moiety, such that a compound of formula 5 is produced; optionally followed by a salt forming reaction;
wherein W, $R^1$, $R^2$, $R^3$, $R^4$ and $R^5$ are as defined above;
wherein Hal represents halogen; and
wherein —$BY_2$ represents a boronic acid, an acyclic boronic ester, a cyclic boronic ester, or a trifluoroborate salt.

In still other aspects, the invention relates to specific solid, preferably crystalline, forms of the compound of Formula A, its hydrates, its salts and hydrates and solvates of its salts, and processes for the formation of such specific solid, preferably crystalline, forms. The solid forms of Compound A of the present invention are identified as polymorph Form $H_A$ and polymorph form A anhydrous, and the solid forms of the monohydrochloride salt of Compound A of the present invention are identified as polymorph Form Ha, polymorph Form A, polymorph Form B, polymorph Form $S_A$, polymorph Form $S_B$, polymorph Form $S_C$, polymorph Form $S_D$ and polymorph Form $S_E$.

In another aspect, the invention relates to a method of treating conditions, disorders or diseases mediated by the activation of PI3K, such as indicated above, in a subject in need of such treatment, which method comprises administering to said subject an effective amount of a solid, preferably crystalline, form of the compound of formula A or its monohydrochloride salt (e.g., polymorph Form $H_A$, polymorph A anhydrous, polymorph Form Ha, polymorph Form A, polymorph Form B, polymorph Form $S_A$, polymorph Form $S_B$, polymorph Form $S_C$, polymorph Form $S_D$ and polymorph Form $S_E$).

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

In the X-ray diagrams discussed below, the angle of diffraction 2theta is plotted on the horizontal axis (x-axis) and the relative line intensity (raw peak intensity) on the vertical (y-axis).

Figure 4:
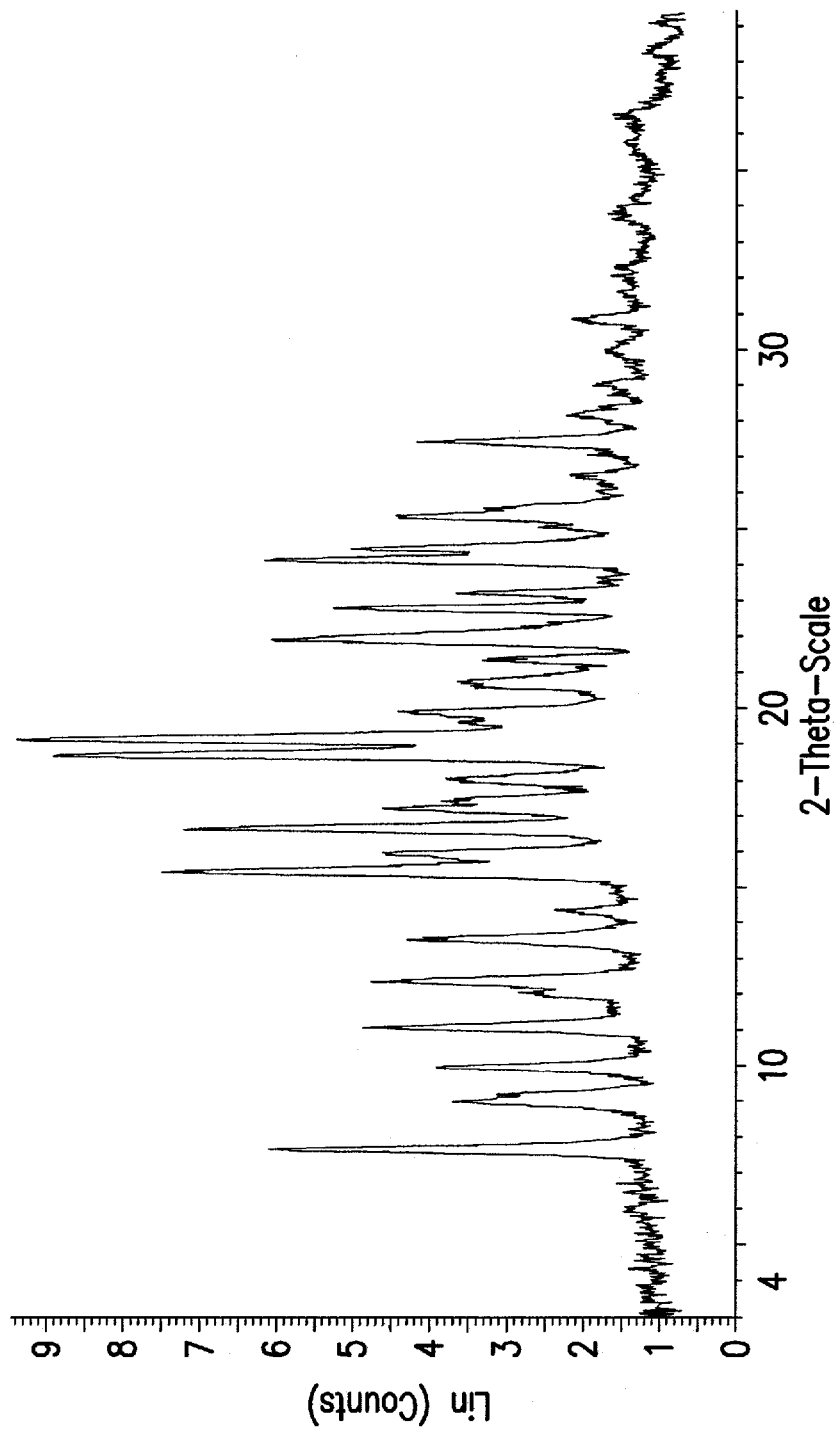

FIG. 4 depicts the X-ray powder diffraction pattern of polymorph Form $H_A$ of 5-(2,6-Di-4-morpholinyl-4-pyrimidinyl)-4-trifluoromethylpyridin-2-amine hemihydrate. X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 5:
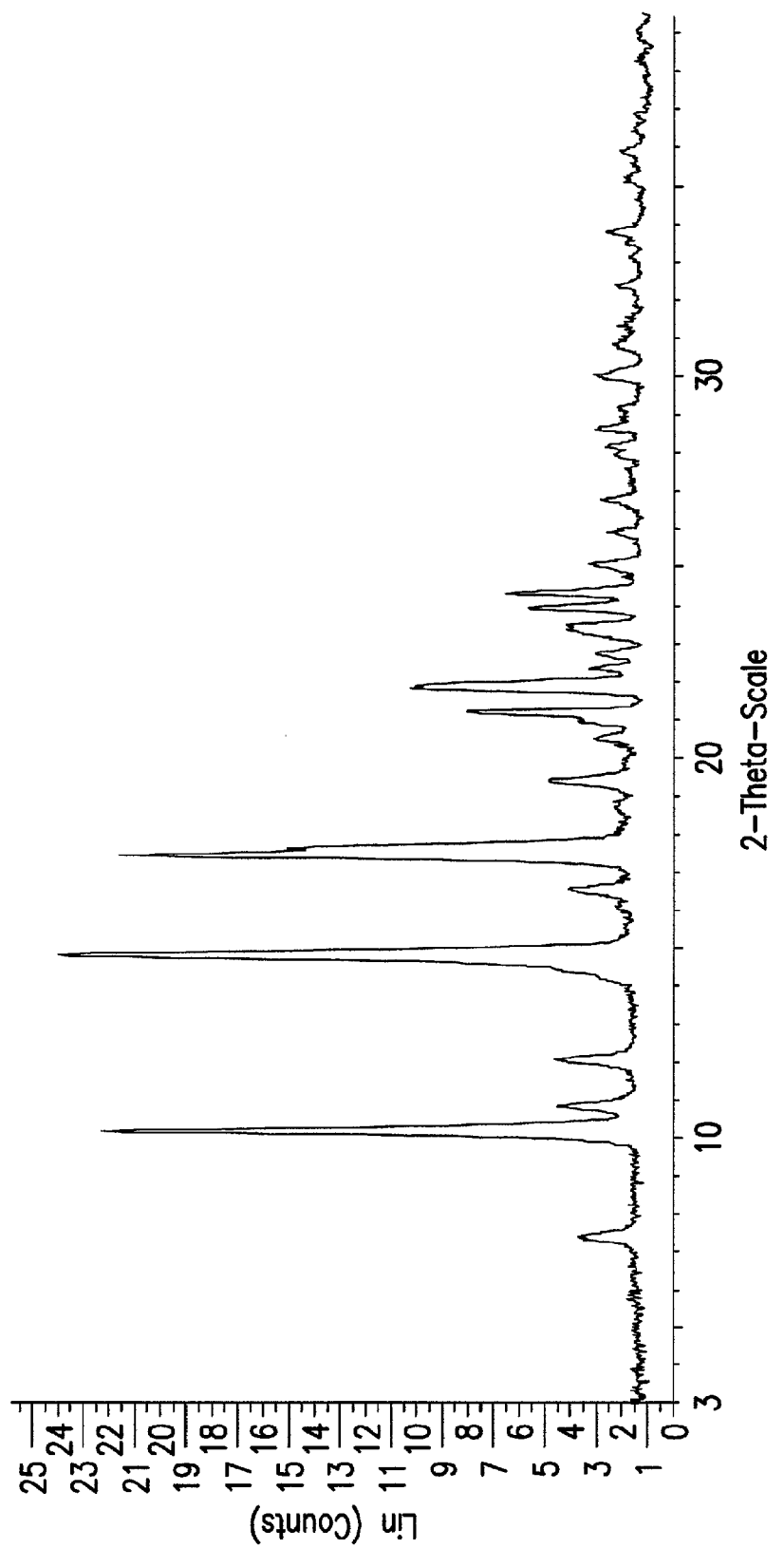

FIG. 5 depicts the X-ray powder diffraction pattern of polymorph Form A anhydrous of 5-(2,6-Di-4-morpholinyl-4-pyrimidinyl)-4-trifluoromethylpyridin-2-amine. X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 6:
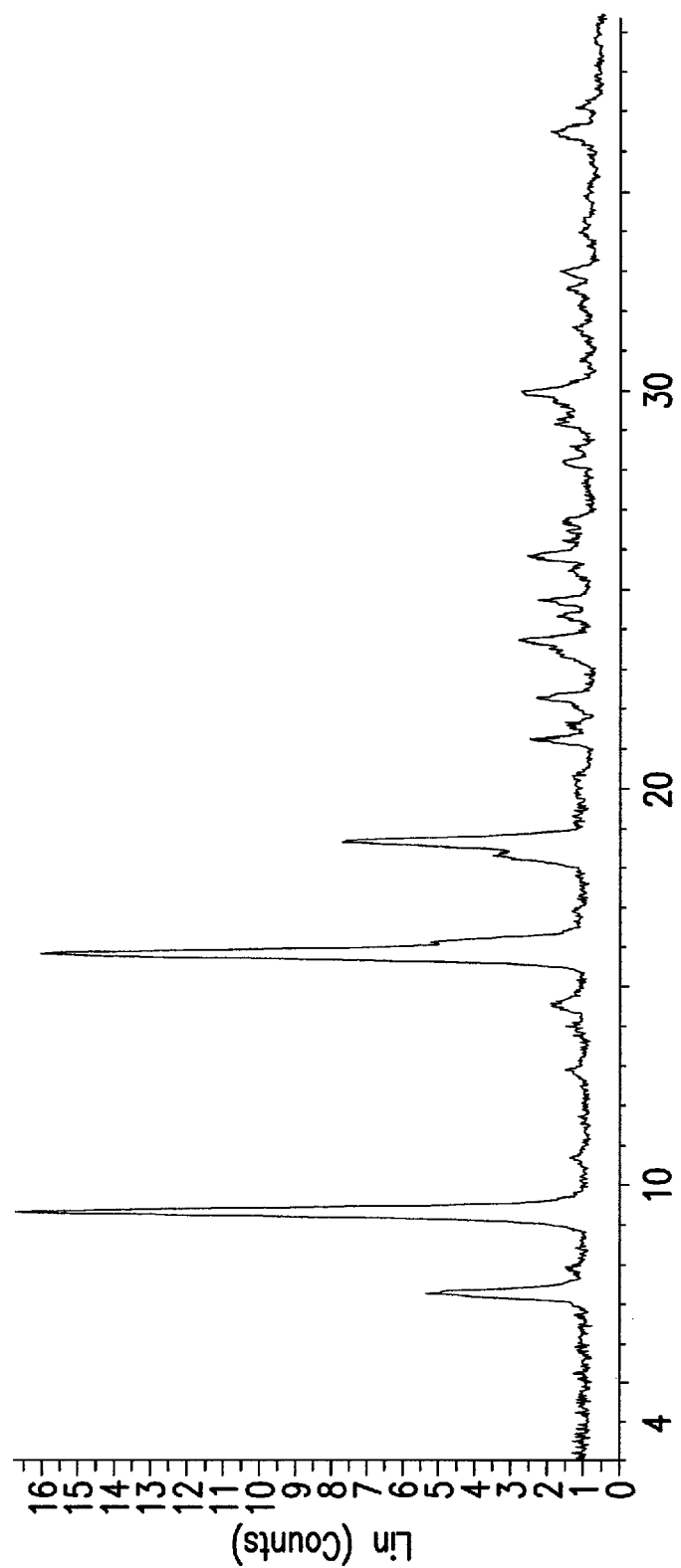

FIG. 6 depicts the X-ray powder diffraction pattern of polymorph Form Ha of 5-(2,6-Di-4-morpholinyl-4-pyrimidinyl)-4-trifluoromethylpyridin-2-amine monohydrochloride monohydrate. X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 7:
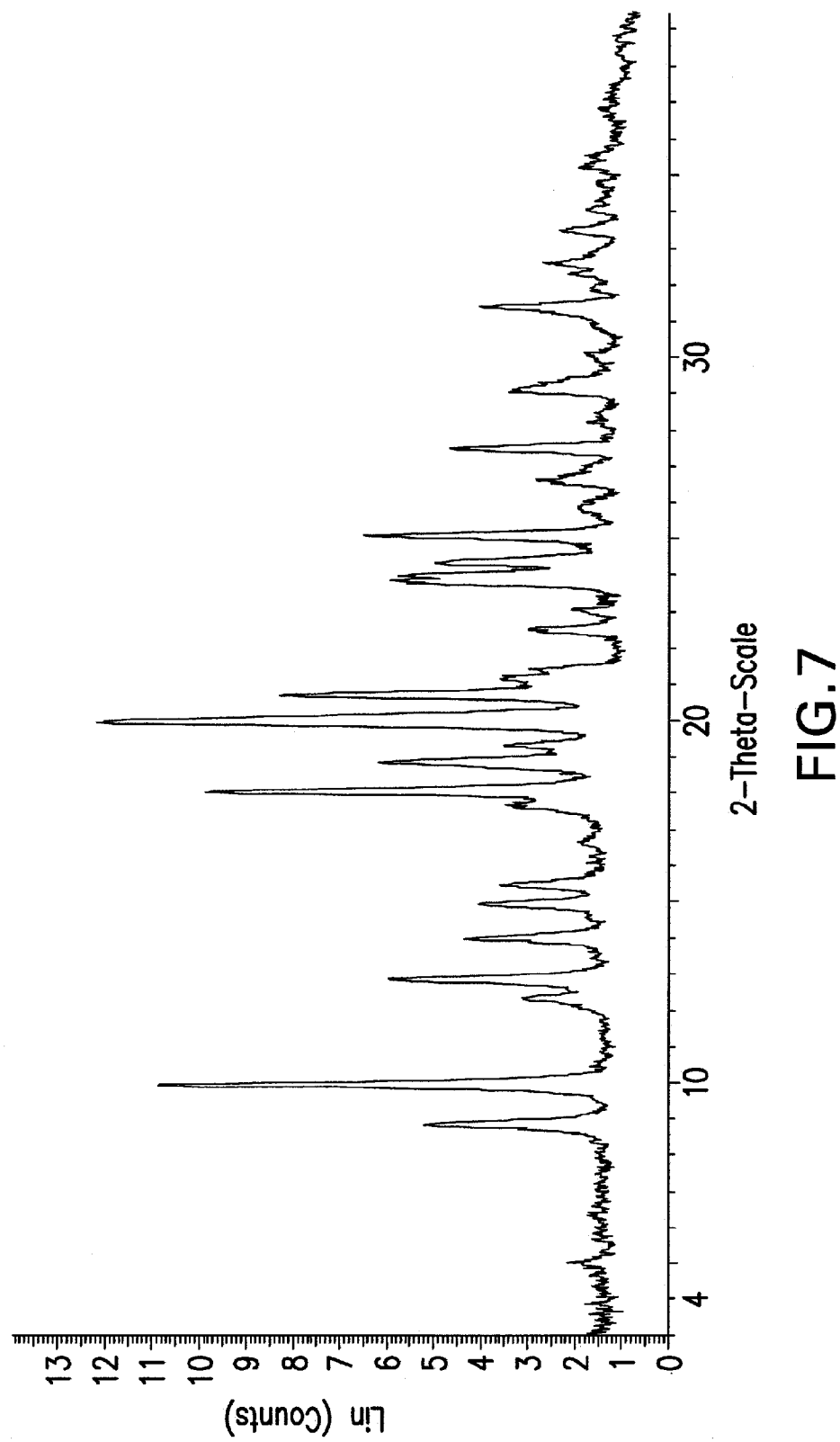

FIG. 7 depicts the X-ray powder diffraction pattern of polymorph Form A of 5-(2,6-Di-4-morpholinyl-4-pyrimidinyl)-4-trifluoromethylpyridin-2-amine monohydrochloride (hydrochloride polymorph form A). X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 8:
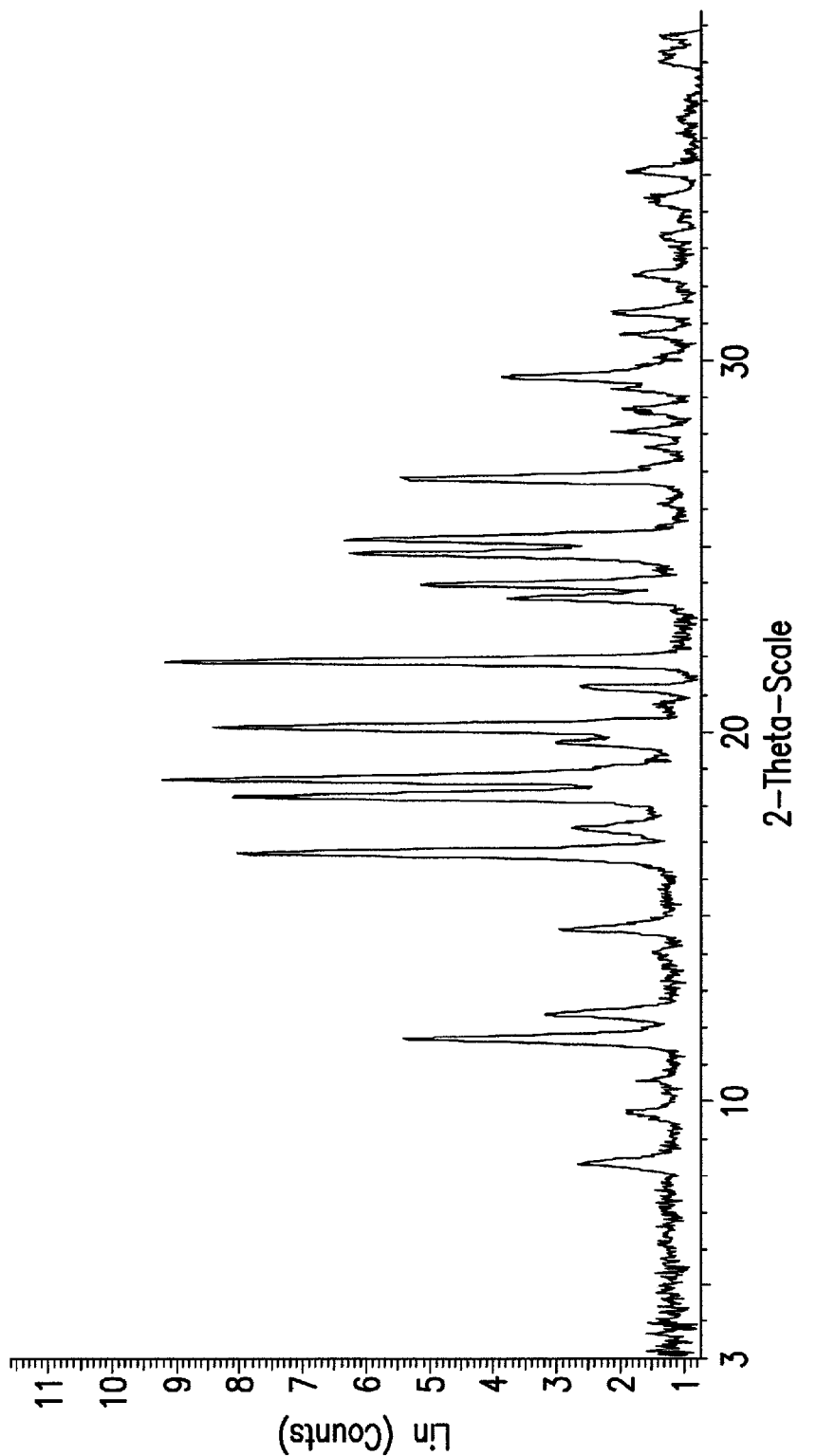

FIG. 8 depicts the X-ray powder diffraction pattern of polymorph Form B of 5-(2,6-Di-4-morpholinyl-4-pyrimidinyl)-4-trifluoromethylpyridin-2-amine monohydrochloride. X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 9:
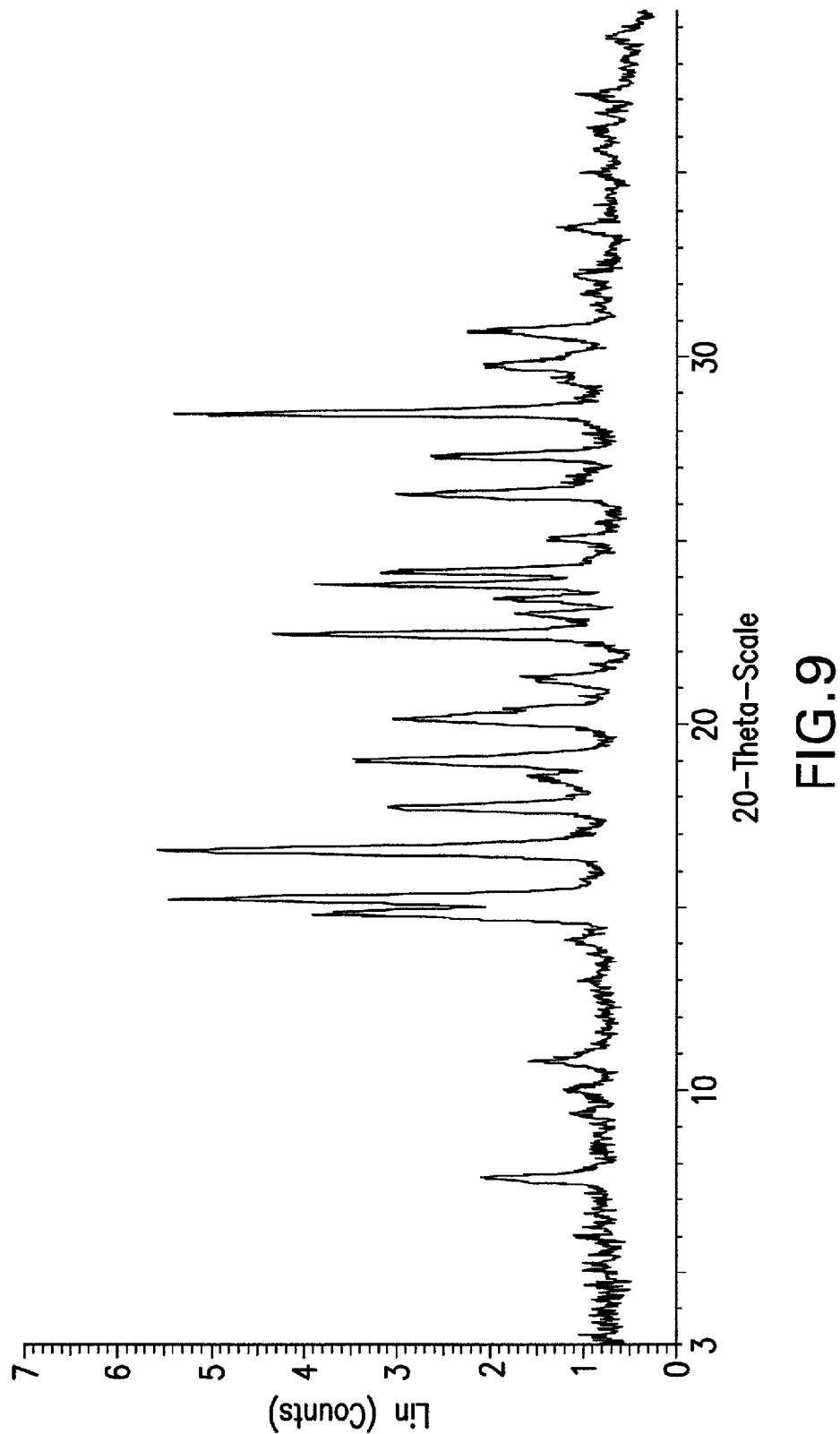

FIG. 9 depicts the X-ray powder diffraction pattern of polymorph Form $S_A$ of 5-(2,6-Di-4-morpholinyl-4-pyrimidinyl)-4-trifluoromethylpyridin-2-amine monohydrochloride solvate. X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 10:
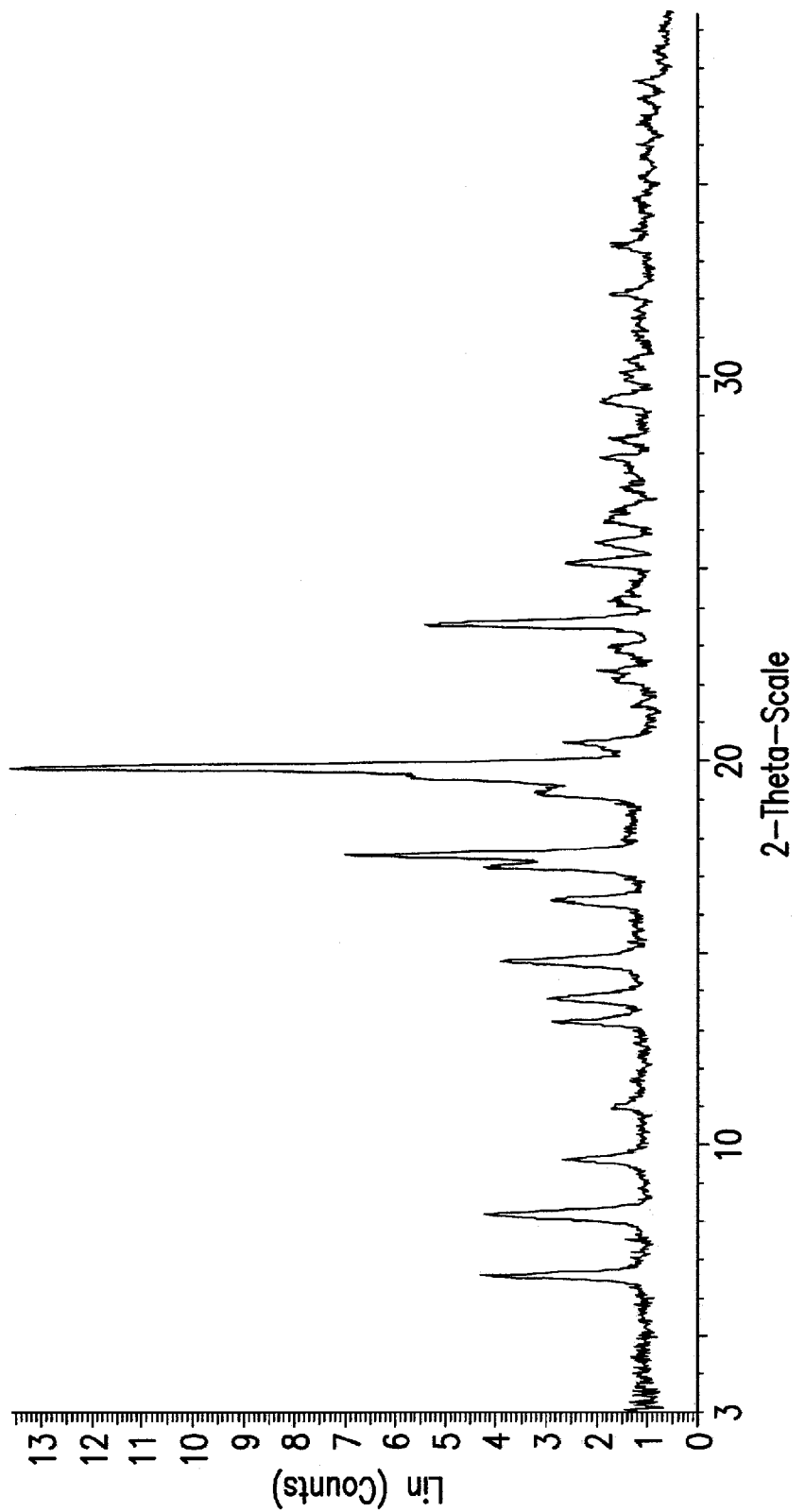

FIG. 10 depicts the X-ray powder diffraction pattern of polymorph Form $S_B$ of 5-(2,6-Di-4-morpholinyl-4-pyrimidinyl)-4-trifluoromethylpyridin-2-amine monohydrochloride solvate. X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 11:
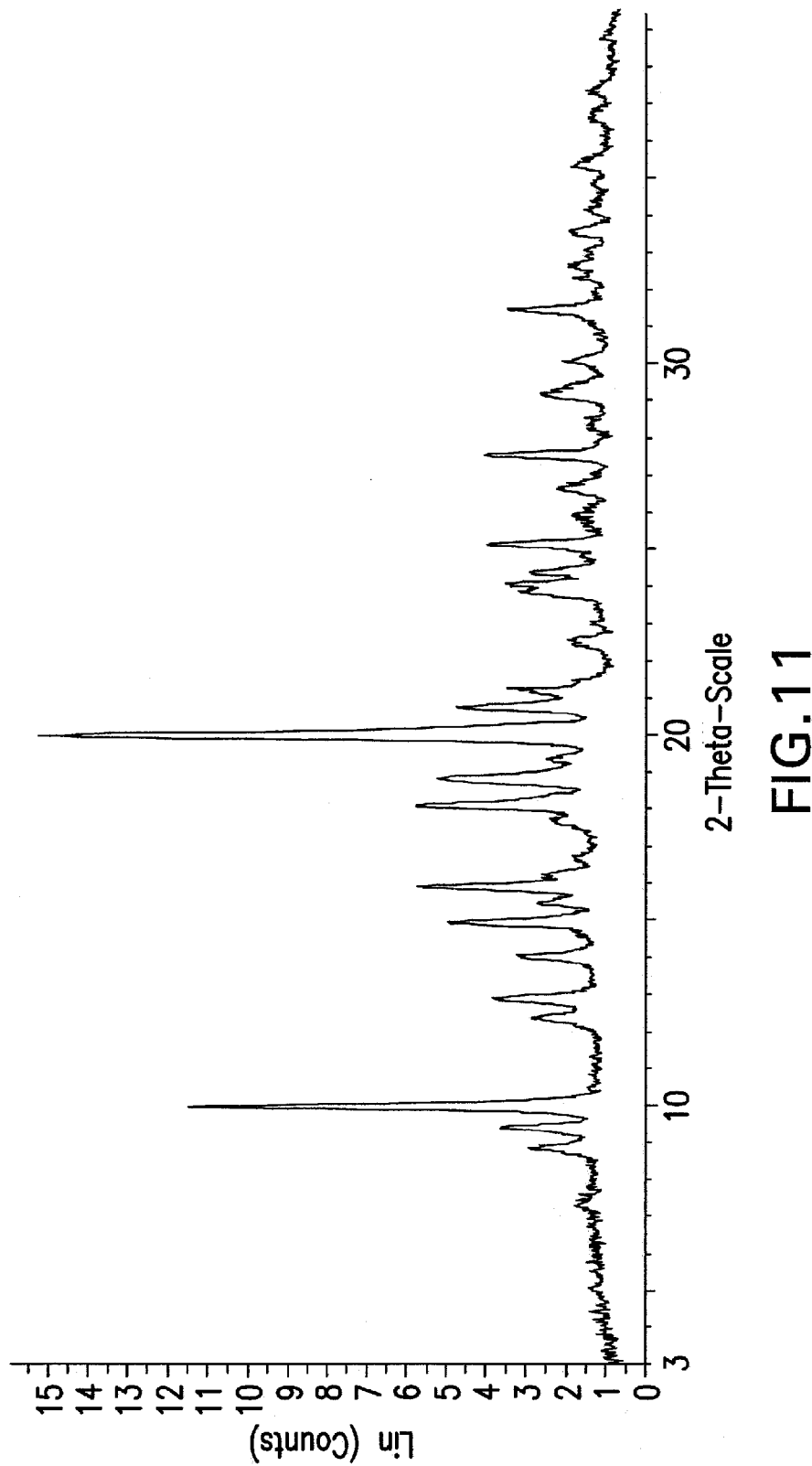

FIG. 11 depicts the X-ray powder diffraction pattern of polymorph Form $S_C$ of 5-(2,6-Di-4-morpholinyl-4-pyrimidinyl)-4-trifluoromethylpyridin-2-amine monohydrochloride solvate. X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 12:
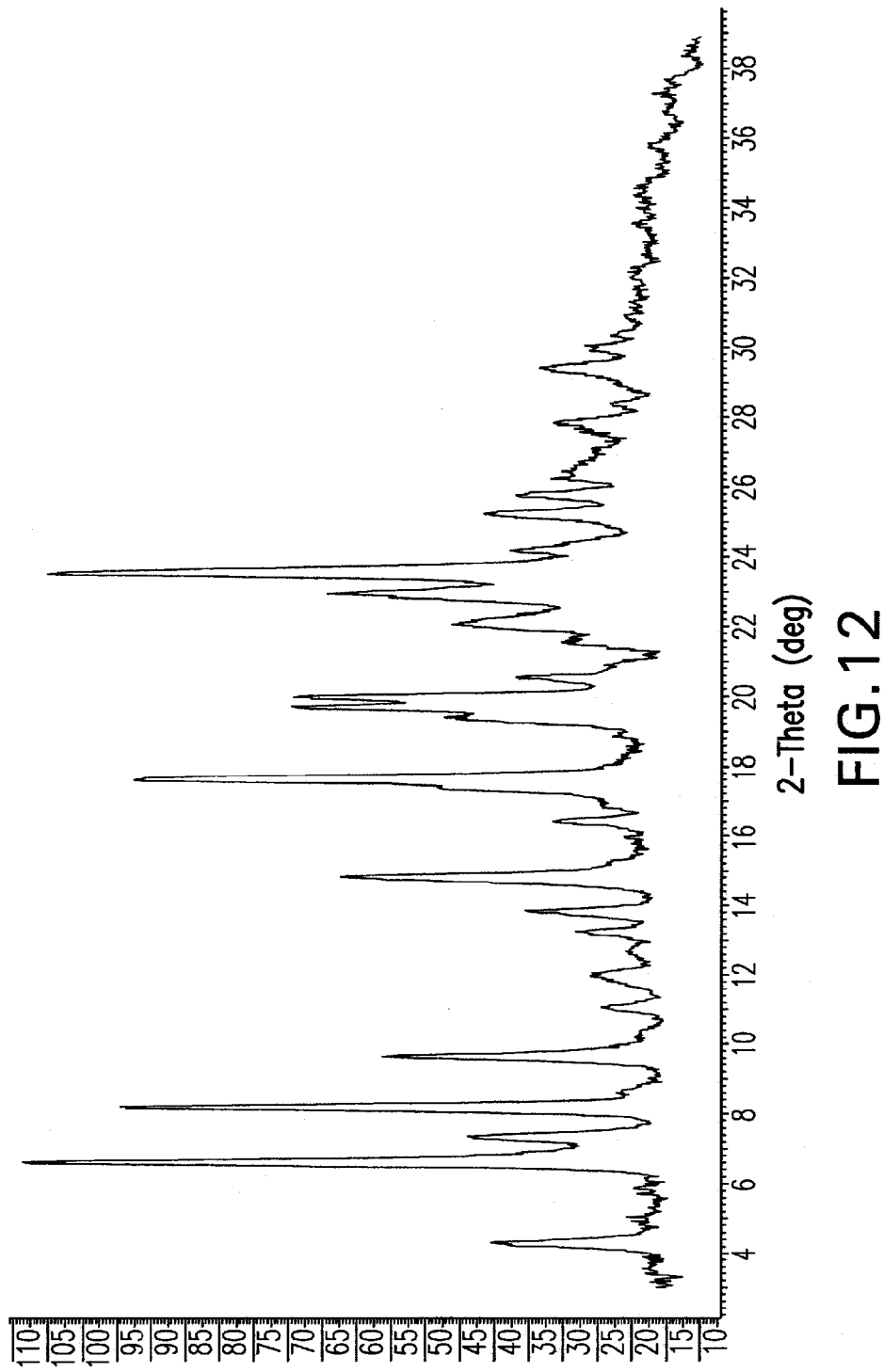

FIG. 12 depicts the X-ray powder diffraction pattern of polymorph Form $S_D$ of 5-(2,6-Di-4-morpholinyl-4-pyrimidinyl)-4-trifluoromethylpyridin-2-amine monohydrochloride solvate. X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 13:
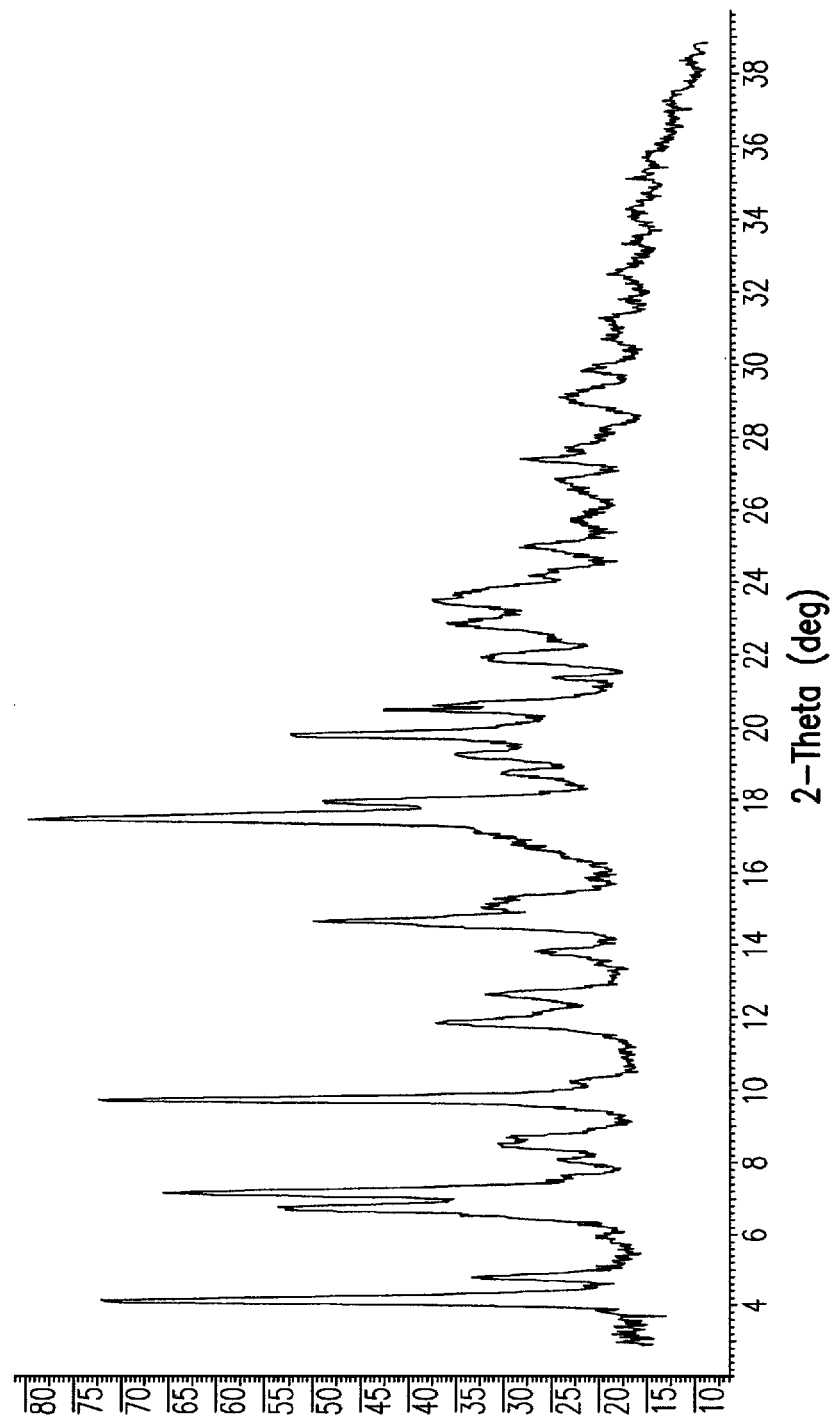

FIG. 13 depicts the X-ray powder diffraction pattern of polymorph Form $S_E$ of 5-(2,6-Di-4-morpholinyl-4-pyrimidinyl)-4-trifluoromethylpyridin-2-amine monohydrochloride solvate. X-ray powder data measured with Bruker AXS Discover D8 instrument (Madison, Wis., USA) with Cu K alpha radiation source, Step 0.02°, Run time 2 minutes, 2Step, Range 2.00-40.00 (Degree Theta) (all 2Theta values are +/−0.3).

Figure 14:
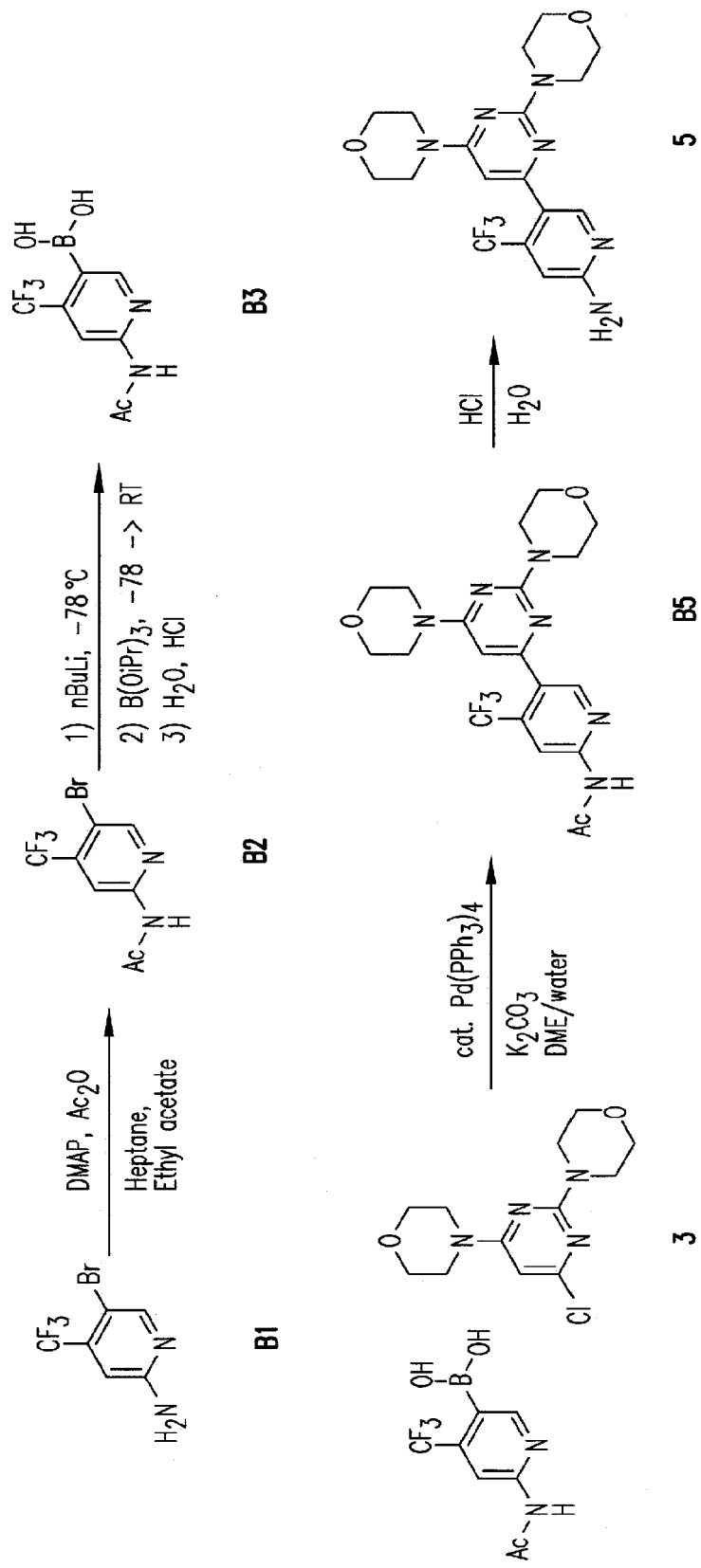

FIG. 14 depicts a process for manufacturing compound 5.

DETAILED DESCRIPTION

The compounds described herein are known to have PI3K inhibiting properties. Accordingly, these compounds are valuable for the treatment of various diseases, in particular for the prophylaxis or treatment of proliferative diseases. Thus, there is a great need to provide improved manufacturing methods for such compounds.

The invention will be better understood and objects other than those set forth above will become apparent when consideration is given to the following detailed description thereof, including the following glossary of terms, the concluding examples and the figures. The following general definitions shall apply in this specification, unless otherwise specified:

"Halogen" (or "halo" or "hal") denotes fluorine, bromine, chlorine or iodine, in particular bromine or chlorine. Halogen-substituted groups and moieties, such as alkyl substituted by halogen (halogenalkyl) can be mono-, poly- or per-halogenated.

Hetero atoms are atoms other than Carbon and Hydrogen, preferably nitrogen (N), oxygen (O) or sulfur (S), in particular nitrogen.

Carbon containing groups, moieties or molecules contain 1 to 12, preferably 1 to 6, more preferably 1 to 4, most preferably 1 or 2, carbon atoms. Any non-cyclic carbon containing group or moiety with more than 1 carbon atom is straight-chain or branched.

The prefix "lower" or "$C_1$-$C_7$" denotes a radical having up to and including a maximum of 7, especially up to and including a maximum of 4 carbon atoms, the radicals in question being either linear or branched with single or multiple branching.

"Alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)—CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_2$, —CH$_2$CH$_2$C(CH$_2$CH$_3$)$_3$, —CH(CH$_3$)CH$_2$.CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Thus the phrase "alkyl groups" includes primary alkyl groups, secondary alkyl groups, and tertiary alkyl groups. Preferred alkyl groups include straight and branched chain alkyl groups having 1 to 12 carbon atoms or 1 to 6 carbon atoms.

"Alkylene" refers to the same residues as noted above for "alkyl," but having two points of attachment. Exemplary alkylene groups include ethylene (—CH$_2$CH$_2$—), propylene (—CH$_2$CH$_2$CH$_2$—), dimethylpropylene (—CH$_2$C(CH$_3$)$_2$CH$_2$—), and cyclohexylpropylene (—CH$_2$CH$_2$CH(C$_6$H$_{13}$)—).

"Alkenyl" refers to straight chain, branched, or cyclic groups from 2 to about 20 carbon atoms such as those described with respect to alkyl groups as defined above, except having one or more carbon-carbon double bonds. Examples include, but are not limited to vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others. Preferred alkenyl groups include straight chain and branched alkenyl groups and cyclic alkenyl groups having 2 to 12 carbon atoms or 2 to 6 carbon atoms.

"Alkynyl" refers to straight chain, branched, or cyclic groups from 2 to about 20 carbon atoms such as those described with respect to alkyl groups as defined above, except having one or more carbon-carbon triple bonds. Examples include, but are not limited to —C⋮C(H), —C⋮C(CH$_3$), —C⋮C(CH$_2$CH$_3$), —C(H$_2$)C⋮C(H), —C(H)$_2$C⋮C(CH$_3$), and —C(H)$_2$C⋮C(CH$_2$CH$_3$) among others. Preferred alkynyl groups include straight chain and branched alkynyl groups having 2 to 12 carbon atoms or 2 to 6 carbon atoms.

Alkyl, alkylene, alkenyl, and alkynyl groups may be substituted. "Substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heteroaryl, heterocyclyl, or cycloalkyl group. Preferred substituted alkyl groups include, among others, alkyl groups in which one or more bonds to a carbon or hydrogen atom is/are replaced by one or more bonds to fluoro, chloro, or bromo group. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other preferred substituted alkyl groups include those in which one or more bonds to a carbon(s) or hydrogen(s) atoms is replaced by a bond to an aryl, heteroaryl, heterocyclyl, or cycloalkyl group. Examples of substituted alkyl are: —(CHz)$_3$NH$_2$, —(CH$_2$)$_3$NH(CH$_3$), —(CH$_2$)$_3$NH(CH$_3$)$_2$—CH$_2$C(═CH$_2$)CH$_2$NH$_2$, .CH$_2$C(═O)CH$_2$NH$_2$, —CH$_2$S(═O)$_2$CH$_3$, —CH$_2$OCH$_2$NH$_2$, —CO$_2$H, —CH$_2$OH, —OH, —OCH$_3$, —OC$_2$H$_5$, —OCF$_3$, —OC(═O)CH$_3$, —OC(═O)NH$_2$)—OC(═O)N(CH$_3$)$_2$, —CN, —NO$_2$, —C(═O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(═O)OCH$_3$, —NHSO—$_2$CH$_3$, —SO$_2$CH$_3$, —SO$_2$NH$_2$, Halo.

"Substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

"Substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

"Alkoxy" refers to RO— wherein R is alkyl. Representative examples of alkoxy groups include methoxy, ethoxy, t-butoxy, trifluoromethoxy, and the like.

"Amino" refers herein to the group —NH$_2$. The term "alkylamino" refers herein to the group —NRR' where R is alkyl and R' is hydrogen or alkyl. The term "arylamino" refers herein to the group —NRR' where R is aryl and R' is hydrogen, alkyl, or aryl. The term "aralkylamino" refers herein to the group —NRR' where R is aralkyl and R' is hydrogen, alkyl, aryl, or aralkyl.

"Alkoxyalkyl" refers to the group -alki-O-alk$_2$ where alki is alkyl or alkenyl, and alk$_2$ is alkyl or alkenyl. The term "aryloxyalkyl" refers to the group -alkyl O-aryl. The term "aralkoxyalkyl" refers to the group -alkylenyl-O-aralkyl.

"Alkoxyalkylamino" refers herein to the group —NR-(alkoxyalkyl), where R is typically hydrogen, aralkyl, or alkyl.

"Aminocarbonyl" refers herein to the group —C(O)—NH$_2$. "Substituted aminocarbonyl" refers herein to the group —C(O)—NRR' where R is alkyl and R$^1$ is hydrogen or alkyl. The term "arylamino-carbonyl" refers herein to the group —C(O)—NRR' where R is aryl and R' is hydrogen, alkyl or aryl. "Aralkylaminocarbonyl" refers herein to the group —C(O)—NRR' where R is aralkyl and R$^1$ is hydrogen, alkyl, aryl, or aralkyl.

"Aminosulfonyl" refers herein to the group —S(O)$_2$—NH$_2$. "Substituted aminosulfonyl" refers herein to the group —S(O)$_2$—NRR' where R is alkyl and R' is hydrogen or alkyl. The term "aralkylaminosulfonlyaryl" refers herein to the group -aryl-S(O)$_2$—NH-aralkyl.

"Carbonyl" refers to the divalent group —C(O)—.

"Carbonyloxy" refers generally to the group —C(O)—O. Such groups include esters, —C(O)—O—R, where R is alkyl, cycloalkyl, aryl, or aralkyl. The term "carbonyloxycycloalkyl" refers generally herein to both a "carbonyloxycarbocycloalkyl" and a "carbonyloxyheterocycloalkyl," i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl.

"Sulfonyl" refers herein to the group —SO$_2$—. "Alkylsulfonyl" refers to a substituted sulfonyl of the structure —SO$_2$R— in which R is alkyl. Alkylsulfonyl groups employed in compounds of the present invention are typically alkylsulfonyl groups having from 1 to 6 carbon atoms in its backbone structure. Thus, typical alkylsulfonyl groups employed in compounds of the present invention include, for example, methyl sulfonyl (i.e., where R is methyl), ethylsulfonyl (i.e., where R is ethyl), propylsulfonyl (i.e., where R is propyl), and the like. The term "arylsulfonyl" refers herein to the group —SO$_2$-aryl. The term "aralkylsulfonyl" refers herein to the group —SO$_2$-aralkyl. The term "sulfonamido" refers herein to —SO$_2$NH$_2$.

"Carbonylamino" refers to the divalent group —NH—C(O)— in which the hydrogen atom of the amide nitrogen of the carbonylamino group can be replaced alkyl, aryl, or aralkyl group. Such groups include moieties such as carbamate esters (—NH—C(O)—O—R) and amides —NH—C(O)—R, where R is a straight or branched chain alkyl, cycloalkyl, or aryl or aralkyl. The term "alkylcarbonylamino" refers to alkylcarbonylamino where R is alkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is aralkyl.

"Guanidino" or "guanidyl" refers to moieties derived from guanidine, H$_2$N—C(=NH)—NH$_2$. Such moieties include those bonded at the nitrogen atom carrying the formal double bond (the "2"-position of the guanidine, e.g., diaminomethyleneamino, (H$_2$N)$_2$C=NH—)) and those bonded at either of the nitrogen atoms carrying a formal single bond (the "1-" and/or "3"-positions of the guanidine, e.g., H$_2$N—C(=NH)—NH—)). The hydrogen atoms at any of the nitrogens can be replaced with a suitable substituent, such as alkyl, aryl, or aralkyl.

"Amidino" refers to the moieties R—C(=N)—NR'— (the radical being at the "N$^1$" nitrogen) and R(NR')C=N— (the radical being at the "N$^2$" nitrogen), where R and R' can be hydrogen, alkyl, aryl, or aralkyl.

"Cycloalkyl" refers to a mono- or polycyclic, heterocyclic or carbocyclic alkyl substituent. Representative cycloalkyl groups include cyclopropyl, cyclobutyl, cyclopentyl, cyclohexyl, cycloheptyl, and cyclooctyl and such rings substituted with straight and branched chain alkyl groups as defined above. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl, and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Substituted heterocycle," "heterocyclic group," "heterocycle," or "heterocyclyl," as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom may be optionally oxidized; wherein the nitrogen and sulfur heteroatoms may be optionally quarternized; and including any bicyclic group in which any of the above heterocyclic rings is fused to a benzene ring or another 5- or 6-membered heterocyclic ring independently defined above. Examples of heterocyclyl groups include, but are not limited to: unsaturated 3- to 8-membered rings containing 1 to 4 nitrogen atoms such as, but not limited to pyrrolyl, dihydropyridyl, pyrimidyl, pyrazinyl, tetrazolyl, (e.g., IH-tetrazolyl, 2H-tetrazolyl); condensed unsaturated heterocyclic groups containing 1 to 4 nitrogen atoms such as, but not limited to, isoindolyl, indolinyl, indolizinyl, quinolyl, indazolyl; unsaturated 3- to 8-membered rings containing 1 to 2 oxygen atoms and 1 to 3 nitrogen atoms such as, but not limited to, oxadiazolyl (e.g., 1,2,4-oxadiazolyl, 1,3,4-oxadiazolyl, 1,2,5-oxadiazolyl); saturated 3- to 8-membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxadiazolyl, benzoxazinyl (e.g., 2H-1,4-benzoxazinyl); unsaturated 3- to 8-membered rings containing 1 to 3 sulfur atoms and 1 to 3 nitrogen atoms such as, but not limited to, thiadiazolyl (e.g., 1,2,3-thiadiazolyl, 1,2,4-thiadiazolyl, 1,3,4-thiadiazolyl, 1,2,-thiadiazolyl); saturated 3- to 8-membered rings containing 1 to 2 sulfur atoms and 1 to 3 nitrogen atoms such as, but not limited to, thiazolodinyl; saturated and unsaturated 3- to 8-membered rings containing 1 to 2 sulfur atoms such as, but not limited to, dihydrodithienyl, dihydrodithionyl, tetrahydrothiophene, tetra-hydrothiopyran; unsaturated condensed heterocyclic rings containing 1 to 2 sulfur atoms and 1 to 3 nitrogen atoms such as, but not limited to, benzothiadiazolyl, benzothiazinyl (e.g., 2H-1,4-benzothiazinyl), dihydrobenzothiazinyl (e.g., 21'-3,4-dihydrobenzothiazinyl), unsaturated 3- to 8-membered rings containing oxygen atoms such as, but not limited to furyl; unsaturated condensed heterocyclic rings containing 1 to 2 oxygen atoms such as benzodioxoyl (e.g., 1,3-benzodioxoyl); unsaturated 3- to 8-membered rings containing an oxygen atom and 1 to 2 sulfur atoms such as, but not limited to, dihydrooxathienyl; saturated 3- to 8-membered rings containing 1 to 2 oxygen atoms and 1 to 2 sulfur atoms such as 1,4-oxathiane; unsaturated condensed rings containing 1 to 2 sulfur atoms such as benzodithienyl; and unsaturated condensed heterocyclic rings containing an oxygen atom and 1 to 2 oxygen atoms such as benzoxathienyl. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl, and benzothienyl. Heterocyclyl groups also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include piperazine, 1,2,3-triazole, 1,2,4-triazole, tetrazole, thiomorpholine, morpholine, homopiperazine, oxazolidin-2-one, pyrrolidin-2-one, quinuclidine, and tetrahydrofuran.

Heterocyclic moieties can be unsubstituted, monosubstituted or disubstituted with various substituents independently selected from hydroxy, halo, oxo (C=O), alkylimino (RN=, wherein R is alkyl or alkoxy group), amino, alkylamino, dialkylamino, acylaminoalkyl, alkoxy, thioalkoxy, polyalkoxy, alkyl, cycloalkyl or haloalkyl. "Unsubstituted heterocyclyl" includes condensed heterocyclic rings such as benzimidazolyl, but does not include heterocyclyl groups that have other groups such as alkyl or halo groups bonded to one of the ring members as compounds such as 2-methylbenzimidazolyl are substituted heterocyclyl groups.

The heterocyclic groups may be attached at various positions as will be apparent to those having skill in the organic and medicinal chemistry arts in conjunction with the disclosure herein. Representative heterocyclics include, for example, imidazolyl, pyridyl, piperazinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, quinolizinyl and those disclosed in WO 2007/084786, para 154 where R is H or a heterocyclic substituent, as described herein.

"Aryl" refers to optionally substituted monocyclic and polycyclic aromatic groups having from 3 to 14 backbone carbon or hetero atoms, and includes both carbocyclic aryl groups and heterocyclic aryl groups. The term refers to, but is not limited to, groups such as phenyl, biphenyl, anthracenyl, naphthenyl by way of example. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms.

"Unsubstituted aryl" includes groups containing condensed rings such as naphthalene. It does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

"Substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g., dihydronaphthyl or tetrahydronaphthyl). Thus, the phrase "substituted aryl" includes, but is not limited to tolyl, and hydroxyphenyl among others.

"Substituted heteroaryl" as used herein refers to a heteroaryl group as defined herein substituted by independent replacement of one, two or three of the hydrogen atoms thereon with Cl, Br, F, I, —OH, —CN, $C_1$-$C_6$-alkyl, $C_1$-$C_6$-alkoxy, $C_1$-$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

When used in connection with aryl substituents, the term "polycyclic aryl" refers herein to fused and non-fused cyclic structures in which at least one cyclic structure is aromatic, such as, for example, benzodioxole (which has a heterocyclic structure fused to a phenyl group), naphthyl, and the like. Exemplary aryl or heteroaryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" or "arylalkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Representative heteroaryl groups include, for example, those shown below. These heteroaryl groups can be further substituted and may be attached at various positions as will be apparent to those having skill in the organic and medicinal chemistry arts in conjunction with the disclosure herein. Representative heteroaryls include, for example, imidazolyl, pyridyl, thiazolyl, triazolyl benzimidazolyl, benzothiazolyl, and benzoxazolyl and those disclosed in WO 2007/084786, para 162 where R is H or a heterocyclic substituent, as described herein.

"Biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy) benzene, and the like. Preferred optionally substituted biaryl groups include: 2-(phenylamino)-N-[4-(2-phenylethynyl)-phenyl]acetamide, 1,4-diphenylbenzene, N-[4-(2-phenylethynyl)phenyl]-2-[benzyl-amino]-acetamide, 2-amino-N-[4-(2-phenylethynyl) phenyl]propanamide, 2-amino-N-[4-(2-phenyl-ethynyl) phenyl]acetamide, 2-(cyclopropylamino)-N-[4-(2-phenylethynyl)-phenyl]-acetamide, 2-(ethylamino)-N-[4-(2-phenylethynyl)phenyl]acetamide, 2-[(2-methyl-propyl) amino]-N-[4-(2-phenylethynyl)phenyl]acetamide, 5-phenyl-2H-benzo-[d]1,3-dioxolene, 2-chloro-1-methoxy-4-phenylbenzene, 2-[(imidazolylmethyl)-amino]-N-[4-(2-phenylethynyl)phenyl]acetamide, 4-phenyl-1-phenoxybenzene, N-(2-amino-ethyl)-[4-(2-phenylethynyl)-phenyl]-carboxamide, 2-{[(4-fluorophenyl)methyl]-amino}-N-[4-(2-phenylethynyl)phenyl]acetamide, 2-{[(4-methylphenyl)methyl]amino}-N-[4-(2-phenyl-ethynyl) phenyl]acetamide, 4-phenyl-1-(trifluoromethyl)-benzene, 1-butyl-4-phenyl-benzene, 2-(cyclohexylamino)-N-[4-(2-phenylethynyl)phenyl]acetamide, 2-(ethyl-methyl-amino)-N-[4-(2-phenylethynyl)phenyl]-acetamide, 2-(butylamino)-N-[4-(2-phenyl-ethynyl)-phenyl]acetamide, N-[4-(2-phenylethynyl)-phenyl]-2-(4-pyridylamino)-acetamide, N-[4-(2-phenylethynyl)phenyl]-2-(quinuclidin-3-ylamino)-acetamide, N-[4-(2-phenyl-ethynyl)phenyl]pyrrolidin-2-yl-carboxamide, 2-amino-3-methyl-N-[4-(2-phenyl-ethynyl)-phenyl]butanamide, 4-(4-phenylbuta-1,3-diynyl) phenylamine, 2-(dimethyl-amino)-N-[4-(4-phenylbuta-1,3-diynyl)phenyl]acetamide, 2-(ethylamino)-N-[4-(4-phenylbuta-1,3-diynyl)-phenyl]acetamide, 4-ethyl-1-phenylbenzene, 1-[4-(2-phenyl-ethynyl)-phenyl]ethan-1-one, N-(1-carbamoyl-2-hydroxypropyl)[4-(4-phenylbuta-1, 3-diynyl)-phenyl]-carbox-amide, N-[4-(2-phenylethynyl)

phenyl]propanamide, 4-methoxy-phenyl phenyl ketone, phenyl-N-benzamide, (tert-butoxy)-N-[(4-phenylphenyl)methyl]-carboxamide, 2-(3-phenyl-phenoxy)ethanehydroxamic acid, 3-phenylphenyl propanoate, 1-(4-ethoxyphenyl)-4-methoxybenzene, and [4-(2-phenylethynyl)-phenyl]pyrrole.

"Optionally substituted" or "substituted" refers to the replacement of hydrogen with one or more monovalent or divalent radical. Suitable substitution groups include, for example, hydroxyl, nitro, amino, imino, cyano, halo, thio, sulfonyl, thioamido, amidino, imidino, oxo, oxamidino, methox-amidino, imidino, guanidino, sulfonamido, carboxyl, formyl, alkyl, substituted alkyl, halo-alkyl, alkyamino, haloalkylamino, alkoxy, haloalkoxy, alkoxy-alkyl, alkylcarbonyl, amino-carbonyl, aryl-carbonyl, aralkylcarbonyl, heteroarylcarbonyl, heteroaralkyl-carbonyl, alkylthio, aminoalkyl, cyanoalkyl, aryl, benzyl, pyridyl, pyrazolyl, pyrrole, thiophene, imidazolyl, and the like.

The substitution group can itself be substituted. The group substituted onto the substitution group can be carboxyl, halo, nitro, amino, cyano, hydroxyl, alkyl, alkoxy, aminocarbonyl, —SR, thioamido, —SO$_3$H, —SO$_2$R, or cycloalkyl, where R is typically hydrogen, hydroxyl or alkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

Representative substituted aminocarbonyl groups include, for example, those shown below. These can be further substituted by heterocyclyl groups and heteroaryl groups as will be apparent to those having skill in the organic and medicinal chemistry arts in conjunction with the disclosure herein. Preferred aminocarbonyl groups include: N-(2-cyanoethyl)-carboxamide, N-(3-methoxypropyl)-carboxamide, N-cyclopropyl-carboxamide, N-(2-hydroxy-isopropyl)-carboxamide, methyl 2-carbonylamino-3-hydroxypropanoate, N-(2-hydroxypropyl)-carboxamide, N-(2-hydroxy-isopropyl)-carboxamide, N-[2-hydroxy-1-(hydroxymethyl)ethyl]-carboxamide, N-(2-carbonylaminoethyl)acetamide, N-(2-(2-pyridyl)ethyl)-carboxamide, N-(2-pyridylmethyl)-carboxamide, N-(oxolan-2-ylmethyl)-carboxamide, N-(4-hydroxypyrrolidin-2-yl)-carboxamide, N-[2-(2-hydroxyethoxy)ethyl]-carboxamide, N-(4-hydroxycyclohexyl)-carboxamide, N-[2-(2-oxo-4-imidazolinyl)ethyl]-carboxamide, N-Carbonylaminomethylyacetamide, N-(3-pyrrolidinylpropyl)-carboxamide, N-[1-(carbonylaminomethyl)pyrrolidin-3-yl]-acetamide, N-(2-morpholin-4-ylethyl)-carboxamide, N-[3-(2-oxopyrrolidinyl)propyl]-carboxamide, 4-methyl-2-oxopiperazine-carbaldehyde, N-(2-hydroxy-3-pyrrolidinylpropyl)carboxamide, N-(2-hydroxy-3-morpholin-4-ylpropyl)-carboxamide, N-{2-[(5-cyano-2-pyridyl)amino]ethyl}-carboxamide, 3-(dimethylamino)-pyrrolidine-carbaldehyde, N-[(5-methylpyrazin-2-yl)methyl]-carboxamide, 2,2,2-trifluoro-N-(1-formylpyrrolidin-3-yl)-acetamide, and the groups shown in WO2007/084786 para 170.

Representative substituted alkoxycarbonyl groups include, for example, those shown in WO2007/084786, paragraphs 171 and 172. These alkoxycarbonyl groups can be further substituted as will be apparent to those having skill in the organic and medicinal chemistry arts in conjunction with the disclosure herein, The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

"Carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, alkyl esters, secondary amides and the like.

As used herein, the term "pharmaceutically acceptable salts" refers to the nontoxic acid or alkaline earth metal salts of the pyrimidine compounds of the invention. These salts can be prepared in situ during the final isolation and purification of the pyrimidine compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-naphth-alenesulfonate, oxalate, pamoate, pectinate, persulfate, 3-phenylproionate, picrate, pivalate, propionate, succinate, sulfate, tartrate, thiocyanate, p-toluene-sulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Basic addition salts can be prepared in situ during the final isolation and purification of the pyrimidine compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethyl-amine, trimethylamine, triethylamine, ethylamine, and the like. Other representative organic amines useful for the formation of base addition salts include diethylamine, ethylenediamine, ethanolamine, diethanolamine, piperazine, pyridine, picoline, triethanolamine and the like, and basic amino acids such as arginine, lysine and ornithine.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula A, such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

Any formula given herein is intended to represent hydrates, solvates, and polymorphs of such compounds, and mixtures thereof, except as specifically identified herein.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. Various isotopically labeled compounds of the present invention, for example those into which radioactive isotopes such as $^3H$, $^{13}C$, and $^{14}C$ are incorporated. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a. readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula (where one or more up to all more general expressions in embodiments characterized as preferred above or below can be replaced with a more specific definition, thus leading to a more preferred embodiment of the invention, respectively).

Where the plural form (e.g., compounds, salts) is used, this includes the singular (e.g., a single compound, a single salt). "A compound" does not exclude that (e.g., in a pharmaceutical formulation) more than one compound of the formula A (or a salt thereof) is present.

Where the singular form (e.g., solvent, base) is used, this includes the plural (e.g., solvents, bases). "A solvent", "the solvent", "a base" or "the base" does not exclude that (e.g., in a reaction mixture) more than one solvent or base is present.

The salts of compounds of formula A are preferably pharmaceutically acceptable salts; such salts are known in the field.

Methods of Synthesizing Compounds of Formula 5

In one aspect, the invention relates to a process for manufacturing a compound of formula 5,

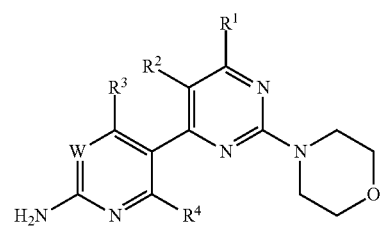

5 or a stereoisomer, tautomer, or a salt thereof, wherein,

W is $CR_W$ or N, wherein $R_W$ is selected from the group consisting of (1) hydrogen, (2) cyano, (3) halogen, (4) methyl, (5) trifluoromethyl, (6) sulfonamido;

$R^1$ is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —$COR_{1a}$, (13) —$CO_2R_{1a}$, (14) —$CONR_{1a}R_{1b}$, (15) —$NR_{1a}R_{1b}$ (17) —$NR_{1a}SO_2R_{1b}$, (18) —$OCOR_{1a}$, (19) —$OR_{1a}$, (21) —$SOR_{1a}$, wherein $R_{1a}$ and $R_{1b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl;

$R^2$ is selected from the group consisting (1) hydrogen, (2) cyano, (3) nitro, (4) halogen, (5) hydroxy, (6) amino, (7) substituted and unsubstituted alkyl, (8) —$COR_{2a}$, and (9) —$NR_{2a}COR_{2b}$, wherein $R_{2a}$ and $R_{2b}$ are independently selected from the group consisting of (a) hydrogen, and (b) substituted or unsubstituted alkyl;

$R^3$ is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, 11) substituted and unsubstituted cycloalkyl, (12) —$COR_{3a}$, (13) —$NR_{3a}R_{3b}$, (14) —$NR_{3a}COR_{3b}$, (15) —$NR_{3a}SO_2R_{3b}$, (16) —$OR_{3a}$ (17) —$SR_{3a}$, (18) —$SOR_{3a}$, (19) —$SO_2R_{3a}$, and wherein $R_{3a}$, and $R_{3b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl; and $R^4$ is selected from the group consisting of (1) hydrogen, and (2) halogen.

This process is referred to as "process step c)". Process step c) may be depicted by the following scheme:

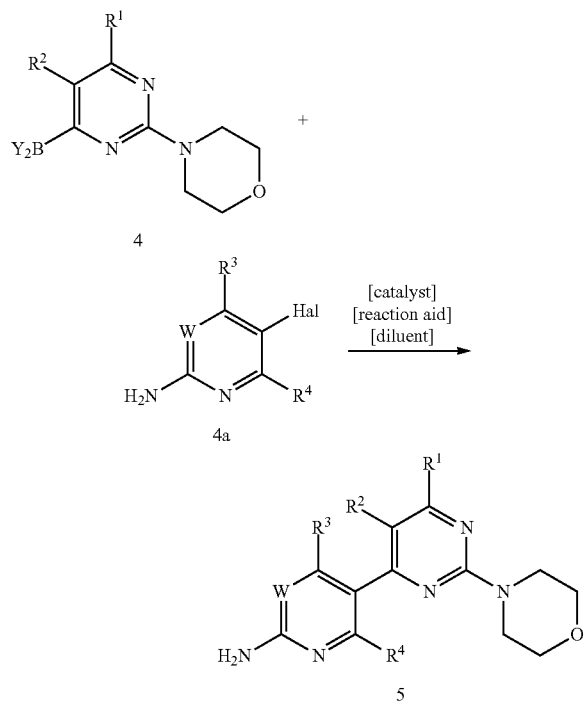

Process step c) comprises the step of reacting a compound of formula 4

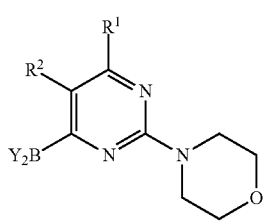

wherein $Y_2B$— represents an acyclic boronic acid, an acyclic boronic ester, an cyclic boronic ester, preferably an acyclic or cyclic boronic ester, $R^1$ and $R^2$ are as defined for formula 5, with a compound of formula 4a

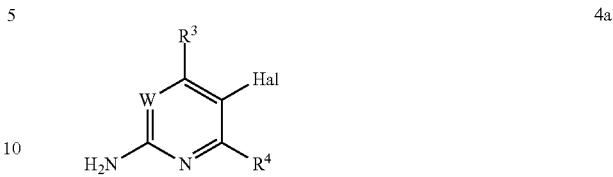

wherein Hal represents halogen, W, $R^3$ and $R^4$ are as defined above for a compound of formula 5 under Suzuki conditions to obtain a compound of formula 5.

Figure 1:
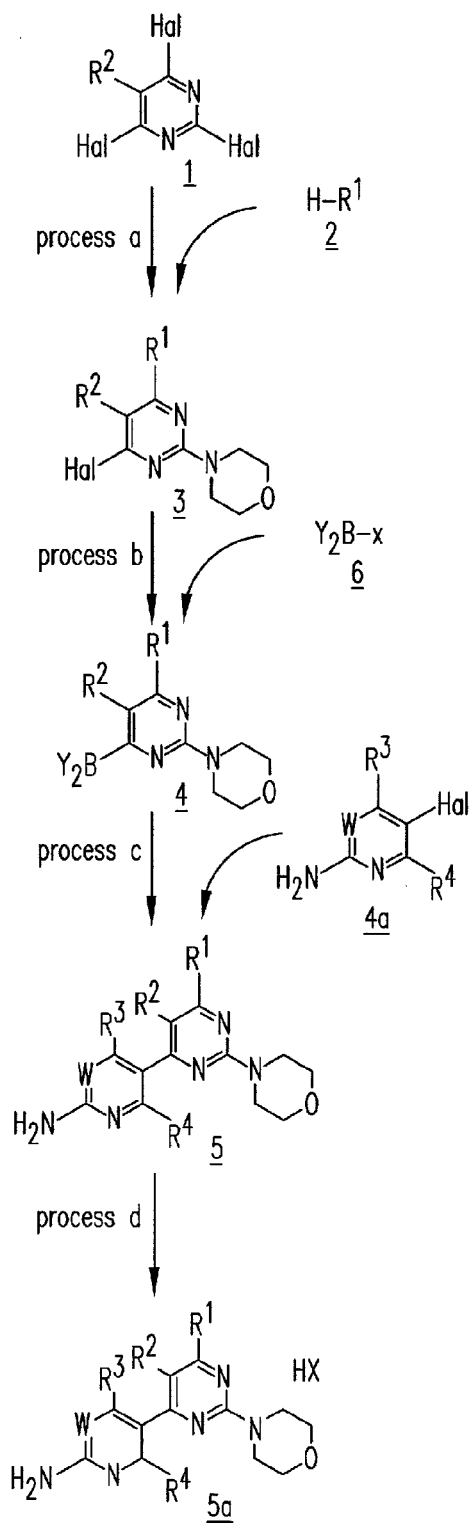
FIG. 1 outlines a general process for manufacturing a compound of formula 5.

Optionally, process step c) may be followed by one or more a salt forming reactions (i.e., process step d). Thus, this process step c) may be combined with process step d) as described below. Alternatively or additionally, process step c) may be combined with process step b) or process steps a) and b). Thus, the invention provides processes for manufacturing compound 5 comprising process step c) or process steps b) and c) or process step a), b) and c), in each case optionally followed by process step d). By combination of processes is meant that the starting material is obtained by applying the preceeding process, e.g., as outlined in FIG. 1. Such starting material my by employed directly (i.e., without isolation and/or purification) or after appropriate work-up steps. All such alternatives are encompassed by the present invention.

Advantageously, catalysts/pre-catalysts for the Suzuki conditions are selected from Pd(0) and Pd(II) compounds, optionally in the presence of phosphines. Particular suitable are $Pd(dbpf)Cl_2$ and $Pd(dppf)Cl_2$ with preference given to $Pd(dbpf)Cl_2$. Suitable amounts of catalyst are in the range of 0.1 to 10 mol %, preferably 3 to 6 mol %.

Advantageously, diluents are selected from the group of polar organic solvents, preferably an ether (such as THF, dioxane, cyclopentylmethyl ether, 2-methyl THF, DMF).

Advantageously, further reaction aids are selected from the group of one or more bases, such as alkalicarbonates, earth alkali carbonates, alkaliphosphates, alkoxides, organic amines with preference given to cesiumcarbonate.

Typical reaction times are in the range of 1 min to 2 days, preferably 10 min to 10 hrs, particular preferably 1 to 3 hours.

Typical reaction temperatures are in the range of 20° C. to reflux conditions, preferably 30° C. to 90° C. particular preferably 40-60° C.

In one embodiment, the invention relates to a process according to process step c) wherein
W represents CH;
$R^1$ represents substituted or unsubstituted heterocyclyl;
$R^2$ represents hydrogen;
$R^3$ represents substituted or unsubstituted alkyl;
$R^4$ represents hydrogen.

In an advantageous embodiment, the invention relates to a process according to process step c) wherein
W represents CH;
$R^1$ represents N-morpholinyl;
$R^2$ represents hydrogen;
$R^3$ represents trifluoromethyl;
$R^4$ represents hydrogen.

In a further advantageous embodiment, the invention relates to a process according to process step c) wherein $Y_2B$— represents a cyclic boronic ester, in particular 4,4,5,5-Tetramethyl-1,3,2-dioxaborolan-2-yl, and acyclic boronic acid and their esters.

In a further advantageous embodiment, the invention relates to a process according to process step c) wherein Hal represents chloro or bromo, in particular bromo.

In a further advantageous embodiment, the invention relates to a process according to process step c) wherein the Suzuki conditions involve the presence of a Pd-catalyst, in particular Pd(dbpf)Cl$_2$.

In a further advantageous embodiment, the invention relates to a process according to process step c) wherein 4, 4a and catalyst are suspended in a diluent as defined above and the reaction aid as defined above is added.

In a further advantageous embodiment, the invention relates to a process according to process step c) wherein the work up of the initially obtained reaction mixture comprises the steps of i) separating insoluble material (e.g., by filtering the insolubles, preferably by filtration using a filtration aid such as a celite pad), ii) separating the organic phase, and optionally replacing the solvent by another solvent (such as isopropyl acetate) iii) removing the residual palladium, and iv) crystallizing the product (preferably after aqueous acid extraction and pH controlled precipitation).

The starting materials, reaction aids and catalysts used in this process step are known or obtainable in analogy to known processes. Advantageously, the starting materials are obtained as described herein.

In another aspect, the invention relates to a process for manufacturing a compound of formula 4

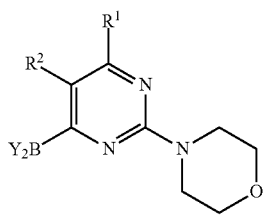
4 wherein
Y$_2$B— represents a boronic ester;
R$^1$ is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —COR$_{1a}$, (13) —CO$_2$R$_{1a}$, (14) —CONR$_{1a}$R$_{1b}$, (15) —NR$_{1a}$R$_{1b}$ (17) —NR$_{1a}$SO$_2$R$_{1b}$, (18) —OCOR$_{1a}$, (19) —OR$_{1a}$, (21) —SOR$_{1a}$, wherein R$_{1a}$ and R$_{1b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl;
R$^2$ is selected from the group consisting (1) hydrogen, (2) cyano, (3) nitro, (4) halogen, (5) hydroxy, (6) amino, (7) substituted and unsubstituted alkyl, (8) —COR$_{2a}$, and (9) —NR$_{2a}$COR$_{2b}$, wherein R$_{2a}$ and R$_{2b}$ are independently selected from the group consisting of (a) hydrogen, and (b) substituted or unsubstituted alkyl.

This process for manufacturing a compound of formula 4 is referred to as "process step b)". Process step b) for the synthesis of compounds of formula 4 may be depicted by the following scheme:

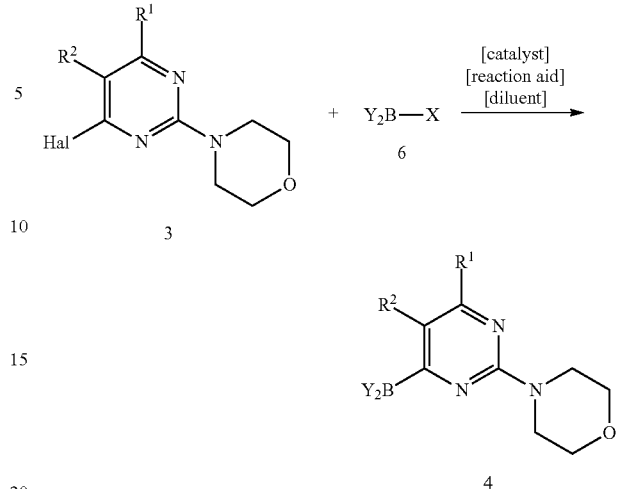

Process step b) comprises the step of reacting a compound of formula 3

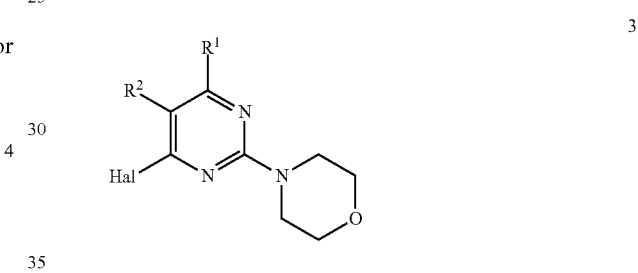
3 wherein
R$^1$ is as defined for a compound of formula 5,
R$^2$ is as defined for a compound of formula 5, and
Hal represents halogen,
with a boronic ester or derivative thereof of the formula 6

Y$_2$B—X    6 wherein
Y$_2$B represents a boronic ester,
X represents hydrogen, hydroxyl, C$_1$-C$_4$ alkoxy or Y$_2$B, preferably Y$_2$B,
optionally in the presence of a catalyst, such as Pd$_2$(dba)$_3$/PCy$_3$, optionally in the presence of a diluent, optionally in the presence of a reaction aid, to obtain a compound of formula 4.

In an advantageous embodiment, the invention relates to a process according to process step b) wherein R$^1$ represents N-morpholinyl.

In an advantageous embodiment, the invention relates to a process according to process step b) wherein Hal represents chloro.

In an advantageous embodiment, the invention relates to a process according to process step b) wherein compound 6 is of the formula 6a:

Y$_2$B—BY$_2$    6a wherein the substituents are as defined herein.

Advantageously, catalysts/pre-catalysts are selected from Pd(0) and Pd(II) compounds, optionally in the presence of phosphines. Particular suitable are Pd$_2$(dba)$_3$/PCy$_3$. Suitable amounts of catalyst are in the range of 0.1 to 20 mol % to preferably 1 to 10 mol %.

Advantageously, diluents are selected from the group of organic solvents, preferably THF, Dioxane, acetonitrile, propionitrile etc.

Advantageously, further reaction aids are selected from the group of one or more bases, such as alkalicarbonates, earth alkali carbonates, with preference given to potassium acetate.

Typical reaction times are in the range of 1 min to 2 days, preferably 10 min to 10 hrs, particular preferably 2 to 4 hours.

Typical reaction temperatures are in the range of 20° C. to reflux conditions, preferably 30° C. to 90° C. particular preferably 80 to 90° C.

The starting materials, reaction aids and catalysts used in this process step are known or obtainable in analogy to known processes. Advantageously, the starting materials are obtained as described herein.

In yet another aspect, the invention relates to process for manufacturing a compound of formula 3

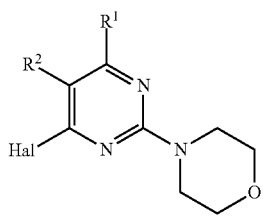

wherein
$R^1$ is a substituted or unsubstituted heterocycle,
$R^2$ is as defined for a compound of formula 5,
Hal represents halogen.

This process for manufacturing a compound of formula 3 is referred to as "process step a)". Process step a) for the synthesis of compounds of formula 3 may be depicted by the following scheme:

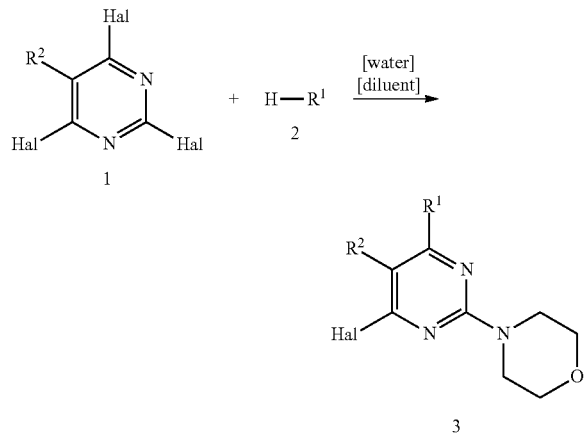

Process step a) comprises the step of reacting a compound of formula 1

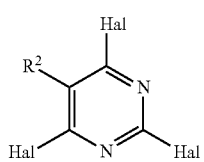

wherein
$R^2$ is as defined for a compound of formula 5,
Hal represents halogen, with a compound of the formula 2 or a mixture of different compounds of formula 2

$$H\!-\!R^1 \qquad 2$$

wherein $R^1$ is a substituted or unsubstituted heterocyclyl or a mixture thereof, under biphasic conditions, optionally in the presence of a reaction aid, optionally in the presence of a diluent, optionally followed by work-up and/or isolation steps.

The invention also relates to a process according to process step a) wherein $R^1$ represents substituted or unsubstituted heterocyclyl.

Advantageously, process step a) may be performed under biphasic conditions. This term denotes reaction conditions where a first and a second liquid phase are present. Said first phase contains water (the "aqueous phase") said second phase contains an organic solvent/diluent (the "organic phase"). Such biphasic systems are known in the art, preferred are water/toluene. It is understood that starting materials, intermediates, product, by-products are present in both phases according to their distribution coefficient. It was found that these biphasic conditions provide higher yields, higher selectivities and improved isolation when compared to non-biphasic conditions.

In an advantageous embodiment, the invention relates to a process according to process step a) wherein $R^2$ represents hydrogen.

In a further advantageous embodiment, the invention relates to a process according to process step a) wherein $R^1$ represents morpholinyl. Thus, a preferred compound of formula 2 is morpholine.

In a further advantageous embodiment, the invention relates to a process according to process step a) wherein Hal represents chloro.

Advantageously, 2 is added in excess, preferably at least 4 equivalents when compared to 1.

In an alternative embodiment, it is also possible to use as starting material 2 a mixture of two components 2-1 and 2-2 wherein 2-1 represents morpholinyl and 2-2 represents a substituted or unsubstituted heterocyclyl, preferably a substituted or unsubstituted 5- or 6-membered ring containing from one to three heteroatoms selected from the group consisting of nitrogen, oxygen, or sulfur; wherein the 5-membered ring has 0-1 double bonds and the 6-membered ring has 0-2 double bonds. In this case, typically mixed substituted derivatives of formula 3 are obtained which may be separated according to known procedures, e.g., chromatography or crystallization. Due to the work up procedures required, this process is less preferred.

Typical reaction times are in the range of 1 min to 2 days, preferably 10 min to 10 hrs, particular preferably 1 to 3 hrs.

Typical reaction temperatures are in the range of 0° C. to 100° C., preferably 20° C. to reflux. particular preferably 80-85° C.

The material obtained in this step may be directly used in a further reaction, e.g., in process step b) as described herein. Alternatively, the material may be purified and isolated e.g., by conversion to a water soluble salt, such as the hydrochloride, followed by precipitation after addition of a base, such as an aqueous solution of NaOH.

The starting materials and reaction aids used in this process step are known and commercially available or obtainable in analogy to known processes.

In still another aspect, the invention relates to a compound of formula 4

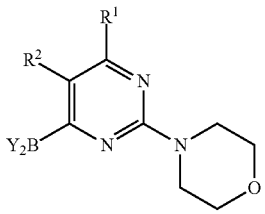

or a stereoisomer, tautomer, or a salt thereof, wherein
R[1] is selected from the group consisting of (1) hydrogen, (2) cyano, (3) nitro, (4) halogen, (5) substituted and unsubstituted alkyl, (6) substituted and unsubstituted alkenyl, (7) substituted and unsubstituted alkynyl, (8) substituted and unsubstituted aryl, (9) substituted and unsubstituted heteroaryl, (10) substituted and unsubstituted heterocyclyl, (11) substituted and unsubstituted cycloalkyl, (12) —$COR_{1a}$, (13) —$CO_2R_{1a}$, (14) —$CONR_{1a}R_{1b}$, (15) —$NR_{1a}R_{1b}$ (17) —$NR_{1a}SO_2R_{1b}$, (18) —$OCOR_{1a}$, (19) —$OR_{1a}$, (21) —$SOR_{1a}$, wherein $R_{1a}$ and $R_{1b}$ are independently selected from the group consisting of (a) hydrogen, (b) substituted or unsubstituted alkyl, (c) substituted and unsubstituted aryl, (d) substituted and unsubstituted heteroaryl, (e) substituted and unsubstituted heterocyclyl, and (f) substituted and unsubstituted cycloalkyl;
R[2] is selected from the group consisting (1) hydrogen, (2) cyano, (3) nitro, (4) halogen, (5) hydroxy, (6) amino, (7) substituted and unsubstituted alkyl, (8) —$COR_{2a}$, and (9) —$NR_{2a}COR_{2b}$, wherein $R_{2a}$ and $R_{2b}$ are independently selected from the group consisting of (a) hydrogen, and (b) substituted or unsubstituted alkyl;
$Y_2B$ represents a boronic ester;
In a preferred embodiment, the preferred definitions for a compound of formula 4 are provided as follows:
R[1] preferably represents substituted and unsubstituted heterocyclyl.
R[1] particular preferably represents N-morpholinyl.
R[2] preferably represents hydrogen;
$Y_2B$ preferably represents a cyclic boronic ester.
$Y_2B$ particular preferably represents 4,4,5,5-Tetramethyl-1,3,2-dioxaborolan-2-yl.
These compounds are, for example, useful in the synthesis of PI3K inhibitors of formula 5. Thus, the invention also relates to the use of compounds of formula 4 for the manufacture of a compound of formula 5. The invention further relates to a compound of formula 4 as defined herein as intermediate.
In another aspect, the invention relates to salt-forming reactions for manufacturing a compound of formula 5a:

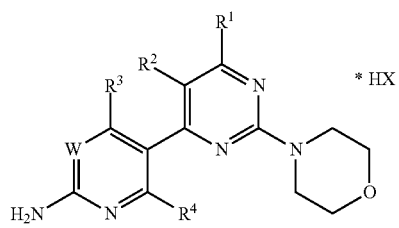

wherein
W, R[1], R[2], R[3] and R[4] are as defined for a compound of formula 5, and HX is an acidic compound for formation of an acid addition salt.

This process ("process step d") for the synthesis of compounds of formula 5a may be depicted by the following scheme:

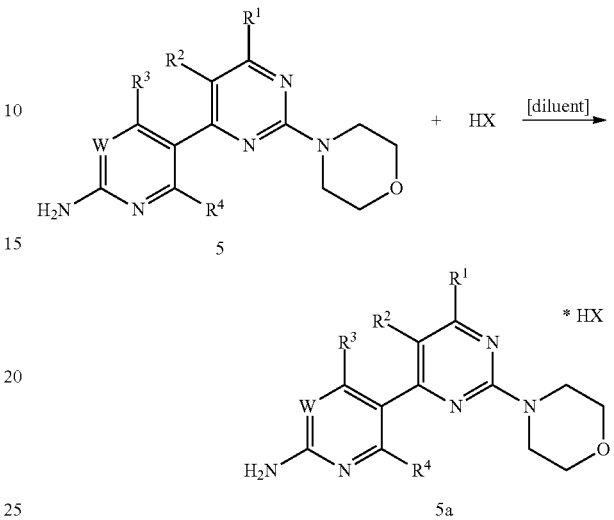

The conversion of free compounds into their corresponding salts is well known in organic chemistry. Basic compounds, as in the present invention, may be converted to the respective salts by addition of acidic compounds (HX), e.g., dissolved in organic or aqueous medium, as gas or in substance. This reaction was not yet applied using the particular starting materials/reaction conditions as described herein where it thus forms a new and inventive process.

This step is preferably used to produce pharmaceutically acceptable acid addition salts from a compound of formula 5. Preferred pharmaceutically acceptable acid addition salts include i) inorganic acids, in particular selected from the group consisting of hydrochloric acid, hydroboric acid, nitric acid, sulfuric acid and phosphoric acid ii) organic acids in particular selected from the group consisting of formic acid, acetic acid, trifluoroacetic acid, fumaric acid, tartaric acid, oxalic acid, maleic acid, methanesulfonic acid, succinic acid, malic acid, methanesulfonic acid, benzenesulfonic acid, and p-toluenesulfonic acid, citric acid, and iii) acidic amino acids such in particular selected from the group consisting of aspartic acid and glutamic acid. A particular preferred acid is hydrochloric acid.

The starting materials, reaction aids used in this process step are known or obtainable in analogy to known processes. Advantageously, the starting materials are obtained as described herein.

The invention provides still another process for manufacturing a compound of formula 5,

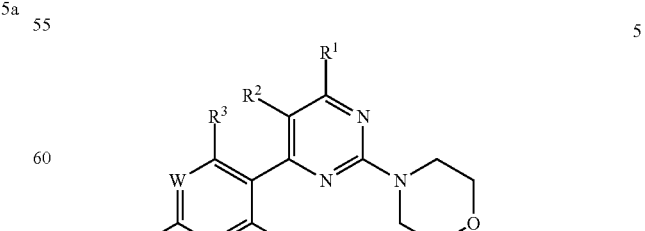

or a stereoisomer, tautomer, or a salt thereof, wherein W, R[1], R[2], R[3] and R[4] are as defined above for a compound of formula 5; comprising the step of reacting a compound of formula 3

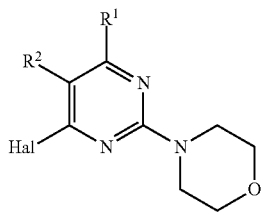

wherein Hal represents halogen and $R^1$ and $R^2$ are as defined for a compound of formula 5; with a compound of formula B3

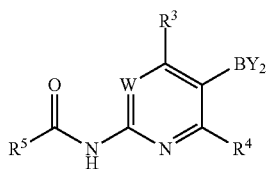

wherein —$BY_2$ represents a boronic acid, an acyclic boronic ester, a cyclic boronic ester, or a trifluoroborate salt, and W, $R^3$ and $R^4$ are as defined for a compound of formula 5; and wherein $R^5$ is selected from the group consisting of (1) hydrogen, (2) substituted or unsubstituted alkyl, (3) substituted or unsubstituted alkyloxy, (4) substituted or unsubstituted aryl, (5) substituted or unsubstituted aryloxy, (6) substituted or unsubstituted arylalkyloxy; under Suzuki conditions, and followed by removal of the $R^5C(O)$— moiety, to obtain a compound of formula 5; optionally followed by a salt forming reaction.

In a particular embodiment, the trifluoroborate salt is a potassium salt.

The Suzuki reaction, which is utilized in many of the reactions described above, is, in principle, a known reaction in organic chemistry and denotes the palladium catalysed coupling of two reactants, wherein one of the reactants contains a reactive halide moiety and the other reactant contains a reactive boronic ester or boronic acid moiety. Suitable conditions for this reaction ("Suzuki conditions") are known to those of skill in the art and relate particularly to the choice of catalyst, of diluent, of further reaction aids, of reaction times and of reaction temperatures. This reaction was not yet applied using the particular starting materials as described herein, where it thus forms a new and inventive process. In a particular embodiment of the process, the Pd-catalyst is $Pd(PPh_3)_4$.

In one embodiment of the process, B3 is prepared by reacting a compound of formula B1

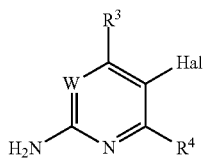

with an acid anhydride $(R^5C=O)_2O$, such that a compound of formula B2 is produced

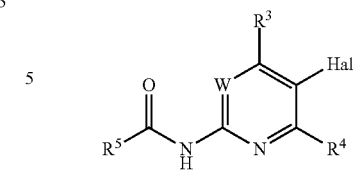

reacting a compound of formula B2 with a reaction mixture comprising a first solvent, a first base and optionally an alcohol additive; reacting the resulting mixture with a second solvent and a second base; reacting the mixture so formed with a boric acid derivative; optionally reacting the mixture so formed with a third solvent and a third base, followed by a boric acid derivative; and optionally reacting the mixture so formed with water and acid, such that a compound of formula B3 is produced.

Non-limiting examples of suitable boric acid derivatives include boric acid esters, such as triisopropyl borate.

In another embodiment, the process for preparing B3 comprises the additional step of converting the boronic acid or borate ester moiety of B3 into a trifluoroborate salt.

In another embodiment, B1 is reacted with a carboxylic acid derivative $(R^5C=O)$—Z, wherein Z is selected from Hal and $O(C=OR^5)$.

In yet another embodiment, of this process, W represents $CR_w$; $R^1$ represents substituted or unsubstituted heterocyclyl; $R^2$ represents hydrogen; $R^3$ represents substituted or unsubstituted alkyl; $R^4$ represents hydrogen; and $R^5$ represents substituted or unsubstituted alkyl, or substituted or unsubstituted alkyloxy. In still another embodiment, W represents CH; $R^1$ represents N-morpholinyl; $R^2$ represents hydrogen; $R^3$ represents trifluoromethyl; $R^4$ represents hydrogen; and $R^5$ represents methyl. In a particular embodiment, —$BY_2$ represents a boronic acid.

In certain embodiments, Hal represents chloro or bromo. In a particular embodiment, Hal represents chloro.

In another aspect, the invention also provides a compound of formula B3

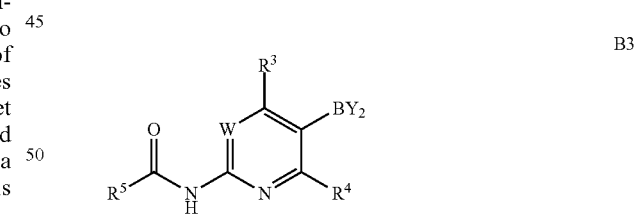

or a stereoisomer, tautomer, or a salt thereof, wherein W, $R^3$, $R^4$, and $R^5$ are as defined above and $BY_2$ represents a boronic acid, an acyclic boronic ester, a cyclic boronic ester, or a trifluoroborate salt.

In one embodiment, W represents $CR_w$; $R^1$ represents substituted or unsubstituted heterocyclyl; $R^2$ represents hydrogen; $R^3$ represents substituted or unsubstituted alkyl; $R^4$ represents hydrogen; and $R^5$ represents substituted or unsubstituted alkyl, or substituted or unsubstituted alkyloxy. In another embodiment, W represents CH; $R^1$ represents N-morpholinyl; $R^2$ represents hydrogen; $R^3$ represents trifluoromethyl; $R^4$ represents hydrogen; $R^5$ represents methyl, and —$BY_2$ represents a boronic acid.

The invention also provides the following process for manufacturing a compound of formula 5,

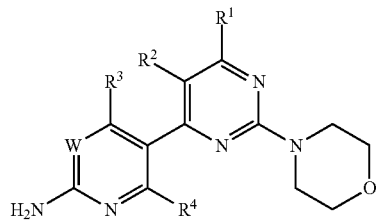

or a stereoisomer, tautomer, or a salt thereof, comprising one or more of the following steps:

Step A: contacting a compound of formula B1

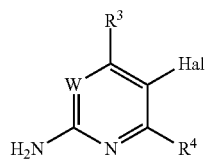

with a reaction mixture comprising a solvent and an acid anhydride $(R^5C=O)_2O$, such that a compound of formula B2 is produced

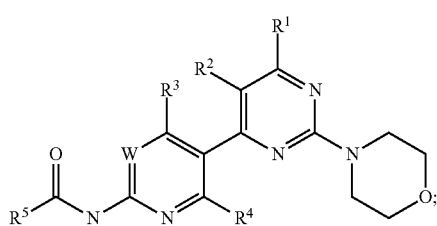

Step B: i) contacting a compound of formula B2 with a reaction mixture comprising a first solvent, a first base and optionally an alcohol additive, ii) contacting the mixture of step (i) with a second solvent and a second base, iii) contacting the mixture of step (ii) with a boric acid derivative, iv) optionally contacting the mixture of step (iii) with a third solvent and a third base and then contacting the resulting mixture with a boric acid derivative, and v) optionally contacting the mixture of step (iii) or step (iv) with water and acid, such that a compound of formula B3 is produced:

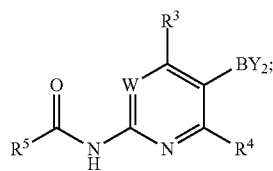

Step C: contacting a compound of formula B3 with a reaction mixture comprising a solvent, a base, a catalyst, and a compound of formula 3

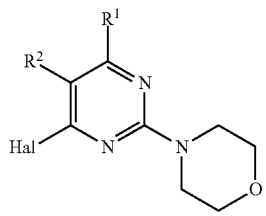

such that a compound of B5 is produced:

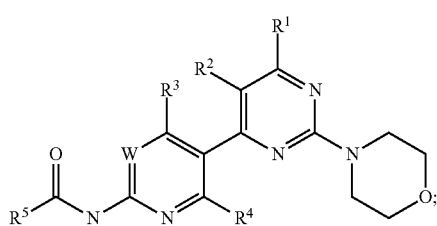

Step D: contacting a compound of formula B5 with a reaction mixture comprising a solvent and a reagent for the removal of the $R^5C(=O)$— moiety, such that a compound of formula 5 is produced; optionally followed by a salt forming reaction; wherein W, $R^1$, $R^2$, $R^3$, $R^4$ are as defined above for the compound of formula 5; wherein Hal represents halogen; and wherein —$BY_2$ represents a boronic acid, an acyclic boronic ester, a cyclic boronic ester, or a trifluoroborate salt.

In one embodiment of Step A, $R_5$ is substituted or unsubstituted $C_{1-6}$ alkyl, substituted or unsubstituted $C_{1-6}$ alkyloxy, substituted or unsubstituted benzyloxy or substituted or unsubstituted phenyl. In another embodiment, $R^5$ is methyl. In an alternative embodiment of Step A, B1 is reacted with a carboxylic acid derivative $(R^5C=O)$—Z, wherein Z is selected from Hal and $O(O=C\ R^5)$.

In another embodiment, the solvents of Steps A and B independently comprises one or more solvents selected from aromatic solvents, aliphatic solvents, halogenated solvents, polar aprotic solvents, and ethereal solvents.

In still another embodiment, the solvent of Step A comprises one or more solvents selected from aromatic solvents, aliphatic solvents, halogenated solvents, polar aprotic solvents, ester solvents and ethereal solvents. In another embodiment, the solvent of Step A comprises one or more solvents selected from ethyl acetate and heptane.

In yet another embodiment of Step A, the reaction mixture comprises dimethylamino pyridine (DMAP).

In one embodiment, the solvent of Step B comprises one or more solvents selected from aromatic solvents, aliphatic solvents, polar aprotic solvents, and ethereal solvents. In another embodiment, the first and second solvents of Step B independently comprise one or more solvents selected from THF and hexane. In yet another embodiment, the first, second and third solvents of Step B, if present, independently comprise one or more solvents selected from THF and hexane.

In a particular embodiment, the first solvent of Step B is THF. In still another particular embodiment, the second solvent of Step B is hexane. In yet another particular embodiment, the third solvent of Step B is hexane.

In another embodiment, the first base of Step B is selected from conjugate bases of hydrocarbons, ammonia, amines, alcohols, and dihydrogen. Non-limiting examples of such bases include n-butyllithium, n-hexyllithium, sodium hydride, tertiary butyl magnesium chloride, lithium amide, lithium isopropoxide and lithium diisopropylamide. Other such bases are known to those skilled in the art. In a particular embodiment, the first base of Step B comprises one or more bases selected from lithium amide, lithium dialkylamides, lithium alkoxides and isomers of butyllithium. In another particular embodiment, the first base of Step B comprises lithium amide. In yet another particular embodiment, the first base of Step B comprises lithium amide and lithium isopropoxide.

In still another embodiment, the second and third bases of Step B are selected from conjugate bases of hydrocarbons. Non-limiting examples of such bases include n-butyllithium, n-hexyllithium and tertiary butyl magnesium chloride. Other such bases are known to those skilled in the art. In certain embodiments, the second and third bases of Step B, if present, are selected from isomers of butyllithium and Grignard reagents. Non-limiting examples of Grignard reagents include tertiary butyl magnesium chloride. In a particular embodiment, the second and third bases of Step B, if present, are n-butyllithium.

It will be understood that the second and third bases of Step B are organometallic reagents that promote the exchange of the halogen atom of B2 with the metal atom of the organometallic reagent.

In a particular embodiment, the first base of Step B comprises lithium amide and lithium isopropoxide, the second base of Step B is n-butyllithium, and the third base of Step B is n-butyllithium. In a preferred embodiment, the additions of n-butyllithium are carried out at a temperature that is lower than −75° C.

In yet another embodiment, the boric acid derivative of Step B is triisopropylborate.

In still another embodiment, the alcohol additive of Step B is selected from methanol, ethanol, 1-propanol, 2-propanol, n-butanol, 2-butanol and t-butanol. In a particular embodiment, the alcohol additive is 2-propanol.

In a preferred embodiment, the first solvent of Step B comprises tetrahydrofuran, the first base of Step B comprises lithium amide, the second and third solvents of Step B are hexane and the second and third bases of step B are n-butyllithium. Advantageously, the sequential addition of n-butyllithium, triisopropylborate, n-butyllithium, and triisopropylborate results in reduced amounts of side-products.

In another embodiment of Step B, the process for preparing B3 comprises the additional step of converting the boronic acid or borate ester moiety of B3 into a trifluoroborate salt.

In one embodiment, the solvent of Step C comprises one or more solvents selected from aromatic solvents, aliphatic solvents, halogenated solvents, polar aprotic solvents, ester solvents, ethereal solvents and water. In another embodiment, the solvent of Step C comprises one or more solvents selected from dimethoxyethane, tetrahydrofuran, 1,4-dioxane, 2-methyl-tetrahydrofuran and water. In a particular embodiment, the solvent of Step C comprises dimethoxyethane and water.

In another embodiment, the base of Step C is selected from acetates, phosphates and carbonates. In a particular embodiment, the base of Step C is potassium carbonate.

In yet another embodiment, the catalyst of Step C comprises palladium. In certain embodiments, the catalyst of Step C is selected from tetrakis(triphenylphosphine)palladium (0) and bis(triphenylphosphine)palladium (II) dichloride. In other embodiments, the palladium catalyst of Step C is formed by combining Pd(OAc)$_2$ with a phosphine ligand. Suitable phosphine ligands are known to those of skill in the art; non-limiting examples include triphenylphosphine and tris(4-methoxy-3,5-dimethylphenyl)phosphine. In a particular embodiment, the catalyst of Step C is tetrakis(triphenylphosphine)palladium (0).

In still another embodiment of Step C, the compound of formula B3 is added constantly to the reaction mixture over the course of the reaction.

In one embodiment, the solvent of Step D comprises one or more solvents selected from aromatic solvents, aliphatic solvents, halogenated solvents, polar aprotic solvents, ester solvents, ethereal solvents and water. In a particular embodiment, the solvent of Step D is water. In another particular embodiment, the solvent of Step D is dioxane.

In Step D, removal of the $R^5C(=O)$— moiety also entails replacement of this moiety with a hydrogen atom. Removal of the $R^5C(=O)$— moiety can be performed by methods known to those of skill in the art. Non-limiting examples of such methods include acid-, base- and metal-mediated reactions. A particular example of such methods is acid-mediated hydrolysis. In one embodiment of Step D, the reagent for the removal of the $R^5C(=O)$— moiety is selected from acids, bases and metal catalysts. In a particular embodiment of Step D, the reagent for the removal of the $R^5C(=O)$— moiety is hydrochloric acid. In another particular embodiment of Step D, the reagent for the removal of the $R^5C(=O)$— moiety is sulfuric acid.

In certain embodiments, Steps A-D independently comprise additional steps or procedures (e.g., to remove reaction byproducts, or to workup, isolate or purify reaction products) as detailed in the examples herein.

In certain embodiments, Steps A-D may be followed by process step d).

The skilled practitioner will recognize several parameters of the foregoing processes that may be varied advantageously in order to obtain a desirable outcome. These parameters include, for example, the methods and means of purification of reaction components and solvents; the order of addition of said reaction components and solvents to the reaction mixture; the duration of reaction of said reaction components and solvents; and the temperature and rate of stirring, mixing or agitation of the reaction components and solvents during said reaction.

It was found that the process embodied by Steps A-D (also including the particular process steps) fulfills one or more of the following criteria: safer; simpler; higher yielding and more economical when compared to known processes for manufacturing compounds of formula 5. Further, the process as described herein is considered scalable, making it suitable for commercial production.

Solid Forms of 5-(2,6-Di-4-morpholinyl-4-pyrimidinyl)-4-trifluoromethylpyridin-2-amine In still other aspects, the invention relates to specific solid, preferably crystalline, forms of the pyrimidine derivative 5-(2,6-Di-4-morpholinyl-4-pyrimidinyl)-4-trifluoromethylpyridin-2-amine ("Compound A" or "the compound of formula A")

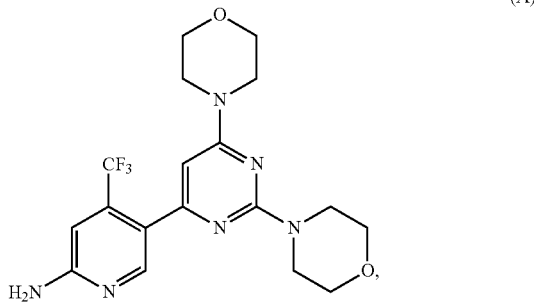

(A)

its hydrates, its salts and hydrates and solvates of its salts, and to a process for the formation of such specific solid, preferably crystalline, forms.

It has been found that the solid forms of the compound of Formula A and its salts surprisingly possess particularly beneficial pharmacokinetic properties that make them particularly suitable for the preparation of pharmaceutical compositions comprising the compound of Formula A and salts thereof. Distinct crystal forms have different physical properties such as melting points, hygroscopicities, solubilities, flow properties or thermodynamic stabilities, and, hence, distinct crystal forms allow the choice of the most suitable form for a certain use or aspect, e.g., the use as an intermediate in the process of drug manufacture or in distinct administration forms like tablets, capsules, ointments or solutions.

Compound A was originally described in WO2007/084786, the contents of which are incorporated herein by reference. Compound A is an inhibitor of PI3K (phosphatidylinositol 3-kinase) and modulates phosphorylation of AKT in biochemical, as well as cellular assays. Accordingly, Compound A and its pharmaceutically acceptable salts, and pharmaceutical compositions comprising Compound A or its pharmaceutically acceptable salt, can be used for the prevention, amelioration or treatment of diseases depending on PI3K. As described herein, the free base of Compound A can be a solid form that exists as one or more polymorph forms, including anhydrous and hydrates. The monohydrochloride salt of Compound A can be a solid form that exists as one or more polymorph forms, including anhydrous, hydrates and solvates. These polymorph forms (alternatively known in the art as polymorphic forms or crystal forms) differ with respect to their X-ray powder diffraction patterns, spectroscopic, physiochemical and pharmacokinetic properties, as well as their thermodynamic stability.

It has now been surprisingly found that under certain conditions new particular solid forms of Compound A, its hydrates, its salts and the hydrates or solvates of its salts may be found, which are described hereinafter, and which have advantageous utilities and properties. It is desirable to have access to different polymorph forms of solid Compound A, its hydrates, its salts and hydrates or solvates of its salts for several reasons. For example, distinct polymorph forms may incorporate distinct impurities upon crystallization, i.e., an impurity incorporated in the hemihydrate form of Compound A is not necessarily incorporated into the anhydrous polymorph form A of Compound. An impurity incorporated into polymorph Form A or B of the monohydrochloride salt of Compound A is not necessarily also incorporated in the polymorph Forms $S_A$, $S_B$, $S_C$, $S_D$ or $S_E$. Thus, the iterative preparation of distinct polymorph forms of Compound A may be used to increase the purity of the finally obtained form. In addition, distinct polymorph forms may exhibit different physical properties such as melting point, hygroscopicity, solubility, flow properties or thermodynamic stability, and therefore, distinct polymorph forms allow the choice of the most suitable form for a given use or aspect, e.g., the use as an intermediate in the process of drug manufacture, in distinct administration forms such as tablets, capsules, ointments, suspensions or solutions, or in the manufacture of a drug form having optimum pharmacokinetic properties.

Thus, in one aspect, provided herein is a solid, preferably crystalline, form of the compound of formula A, or a hydrate of the compound of formula A, or a salt of compound of formula A, or a hydrate or solvate of a salt of compound of formula A.

In one embodiment, the compound of formula A is polymorph Form $H_A$ of Compound A. Polymorph Form $H_A$ is a hemihydrate and can be defined by reference to one or more characteristic signals that result from analytical measurements including, but not necessarily limited to, the X-ray powder diffraction pattern of FIG. 4. Polymorph Form $H_A$ can also be defined by reference to one or more of the following characteristic signals:

In one embodiment, the polymorph Form $H_A$ exhibits an X-ray powder diffraction pattern having characteristic peaks expressed in degrees 2-Theta at angles of 19.2°+/−0.3° and 18.7°+/−0.3°. In another embodiment, polymorph Form $H_A$ exhibits an X-ray powder diffraction pattern having characteristic peaks expressed in degrees 2-Theta at angles of 15.5°+/−0.3° and 16.7°+/−0.3°. In yet another embodiment, Form $H_A$ exhibits an X-ray powder diffraction pattern having characteristic peaks expressed in degrees 2-Theta at angles of 7.7°+/−0.3, 22.0°+/−0.3°, and 22.0°+/−0.3°. In still another embodiment, polymorph Form $H_A$ exhibits an X-ray powder diffraction pattern having characteristic peaks expressed in degrees 2-Theta at angles of 19.2°+/−0.3° and 18.7°+/−0.3°, 15.5°+/−0.3° and 16.7°+/−0.3°, and 7.7°+/−0.3, 22.0°+/−0.3°, and 22.0°+/−0.3°. In a further embodiment, polymorph Form $H_A$ exhibits an X-ray powder diffraction pattern substantially in accordance with FIG. 4 and Table 1.

It has been discovered that polymorph Form A of the monohydrochloride salt of the compound of Formula A exhibits lower moisture uptake than either the free base or monohydrochloride monohydrate. In experiments, polymorph Form A of the monohydrochloride salt of the compound of Formula A exhibited a maximum moisture uptake of less than 0.1% at 25° C. and up to 92% relative humidity. The hemi-hydrate polymorph Form $H_A$ of the compound of Formula A exhibited moisture uptake of 1.9% at 25% relative humidity, the polymorph Form A anhydrous of the compound of Formula A exhibited moisture uptake of 8.9% at 85% relative humidity, and the monohydrochloride monohydrate of the compound of Formula A exhibited moisture uptake of 4.4% at 75% relative humidity and 4.9% at 95% relative humidity. Polymorph Form A of the monohydrochloride salt of the compound of Formula A is surprisingly only slightly hydroscopic, thus providing stable formulations while minimizing the risk of intrinsic chemical breakdown.

In one embodiment, the compound of formula A is polymorph Form A anhydrous of Compound A. Polymorph Form A anhydrous can be defined by reference to one or more characteristic signals that result from analytical measurements including, but not necessarily limited to, the X-ray powder diffraction pattern of FIG. 5. Polymorph Form A anhydrous can also be defined by reference to one or more of the following characteristic signals:

In one embodiment, the polymorph Form A anhydrous exhibits an X-ray powder diffraction pattern having characteristic peaks expressed in degrees 2-Theta at angles of 14.8°+/−0.3° and 10.2°+/−0.3°. In another embodiment, the polymorph Form A anhydrous exhibits an X-ray powder diffraction pattern having characteristic peaks expressed in degrees 2-Theta at angles of 17.4°+/−0.3 and 21.8°+/−0.3°. In yet another embodiment, the polymorph Form A anhydrous exhibits an X-ray powder diffraction pattern having characteristic peaks expressed in degrees 2-Theta at angles of 14.8°+/−0.3° and 10.2°+/−0.3° and 17.4°+/−0.3 and 21.8°+/−0.3°. In still another embodiment, the polymorph Form A anhydrous exhibits an X-ray powder diffraction pattern substantially in accordance with FIG. 5 and Table 2.

In one embodiment, the monohydrochloride monohydrate of the compound of formula A has the polymorph Form Ha. Polymorph Form Ha can be defined by reference to one or more characteristic signals that result from analytical measurements including, but not necessarily limited to, the X-ray powder diffraction pattern of FIG. 6. Polymorph Form Ha can also be defined by reference to one or more of the following characteristic signals:

In one embodiment, polymorph Form Ha exhibits an X-ray powder diffraction pattern having characteristic peaks expressed in degrees 2-Theta at angles of 9.3°+/−0.3° and 15.8°+/−0.3°. In another embodiment, polymorph Form Ha exhibits an X-ray powder diffraction pattern having characteristic peaks expressed in degrees 2-Theta at angles of 7.2°+/−0.3 and 18.6°+/−0.3°. In yet another embodiment, polymorph Form Ha exhibits an X-ray powder diffraction pattern having characteristic peaks expressed in degrees 2-Theta at angles of 9.3°+/−0.3° and 15.8°+/−0.3° and 7.2°+/−0.3 and 18.6°+/−0.3°. In still another embodiment, polymorph Form Ha exhibits an X-ray powder diffraction pattern substantially in accordance with FIG. 6 and Table 3.

In one embodiment, the monohydrochloride of the compound of formula A has the polymorph Form A. The polymorph Form A of the monohydrochloride of the compound of formula A is anhydrous and can be defined by reference to one or more characteristic signals that result from analytical measurements including, but not necessarily limited to, the X-ray powder diffraction pattern of FIG. 7. Polymorph Form A of the monohydrochloride of the compound of formula A can also be defined by reference to one or more of the following characteristic signals:

In one embodiment, polymorph Form A of the monohydrochloride of the compound of formula A exhibits an X-ray powder diffraction pattern having characteristic peaks expressed in degrees 2-Theta at angles of 9.9°+/−0.3° and 20.0°+/−0.3°. In another embodiment, polymorph Form A of the monohydrochloride of the compound of formula A exhibits an X-ray powder diffraction pattern having characteristic peaks expressed in degrees 2-Theta at angles of 18.0°+/−0.3 and 20.7°+/−0.3°. In yet another embodiment, polymorph Form A of the monohydrochloride of the compound of formula A exhibits an X-ray powder diffraction pattern having characteristic peaks expressed in degrees 2-Theta at angles of 8.8°+/−0.3 and 25.0°+/−0.3°. In still another embodiment, polymorph Form A of the monohydrochloride of the compound of formula A exhibits an X-ray powder diffraction pattern having characteristic peaks expressed in degrees 2-Theta at angles of 9.9°+/−0.3° and 20.0°+/−0.3°, 18.0°+/−0.3 and 20.7°+/−0.3°, and 8.8°+/−0.3 and 25.0°+/−0.3°. In a further embodiment, polymorph Form A of the monohydrochloride of the compound of formula A exhibits an X-ray powder diffraction pattern substantially in accordance with FIG. 7 and Table 4.

In one embodiment, the monohydrochloride of the compound of formula A has the polymorph form B. The polymorph Form B of the monohydrochloride of the compound of formula A is anhydrous and can be defined by reference to one or more characteristic signals that result from analytical measurements including, but not necessarily limited to, the X-ray powder diffraction pattern of FIG. 8. Polymorph Form B of the monohydrochloride of the compound of formula A can also be defined by reference to one or more of the following characteristic signals:

In one embodiment, polymorph Form B of the monohydrochloride of the compound of formula A exhibits an X-ray powder diffraction pattern having characteristic peaks expressed in degrees 2-Theta at angles of 18.7°+/−0.3° and 21.8+/−0.3°. In another embodiment, polymorph Form B of the monohydrochloride of the compound of formula A exhibits an X-ray powder diffraction pattern having characteristic peaks expressed in degrees 2-Theta at angles of 18.3°+/−0.3 and 20.1°+/−0.3°. In yet embodiment, polymorph Form B of the monohydrochloride of the compound of formula A exhibits an X-ray powder diffraction pattern having characteristic peaks expressed in degrees 2-Theta at angles of 16.7°+/−0.3 and 26.8°+/−0.3°. In still another embodiment, polymorph Form B of the monohydrochloride of the compound of formula A exhibits an X-ray powder diffraction pattern having characteristic peaks expressed in degrees 2-Theta at angles of 18.7°+/−0.3° and 21.8°+/−0.3°, 18.3°+/−0.3 and 20.1°+/−0.3°, and 16.7°+/−0.3 and 26.8°+/−0.3°. In a further embodiment, polymorph Form B of the monohydrochloride of the compound of formula A exhibits an X-ray powder diffraction pattern substantially in accordance with FIG. 8 and Table 5.

In one embodiment, the monohydrochloride of the compound of formula A has the polymorph form $S_A$. Polymorph form $S_A$ is a solvate and can be defined by reference to one or more characteristic signals that result from analytical measurements including, but not necessarily limited to, the X-ray powder diffraction pattern of FIG. 9. Polymorph form $S_A$ can also be defined by reference to one or more of the following characteristic signals:

In one embodiment, polymorph form $S_A$ exhibits an X-ray powder diffraction pattern having characteristic peaks expressed in degrees 2-Theta at angles of 16.6°+/−0.3° and 28.4°+/−0.3°. In another embodiment, polymorph form $S_A$ exhibits an X-ray powder diffraction pattern having characteristic peaks expressed in degrees 2-Theta at angles of 15.2°+/−0.3 and 22.4°+/−0.3°. In yet embodiment, polymorph form $S_A$ exhibits an X-ray powder diffraction pattern having characteristic peaks expressed in degrees 2-Theta at angles of 14.8°+/−0.3 and 23.8°+/−0.3°. In still another embodiment, polymorph form $S_A$ exhibits an X-ray powder diffraction pattern having characteristic peaks expressed in degrees 2-Theta at angles of 16.6°+/−0.3° and 28.4°+/−0.3°, 15.2°+/−0.3 and 22.4°+/−0.3°, and 14.8°+/−0.3 and 23.8°+/−0.3°. In a further embodiment, polymorph form $S_A$ exhibits an X-ray powder diffraction pattern substantially in accordance with FIG. 9 and Table 6.

In one embodiment, the monohydrochloride of the compound of formula A has the polymorph form $S_B$. Polymorph form $S_B$ is a solvate and can be defined by reference to one or more characteristic signals that result from analytical measurements including, but not necessarily limited to, the X-ray powder diffraction pattern of FIG. 10. Polymorph form $S_B$ can also be defined by reference to one or more of the following characteristic signals:

In one embodiment, polymorph form $S_B$ exhibits an X-ray powder diffraction pattern having characteristic peaks expressed in degrees 2-Theta at angles of 19.8°+/−0.3° and 17.5°+/−0.3°. In another embodiment, polymorph form $S_B$ exhibits an X-ray powder diffraction pattern having characteristic peaks expressed in degrees 2-Theta at angles of 14.8°+/−0.3 and 23.5°+/−0.3°. In yet another embodiment, polymorph form $S_B$ exhibits an X-ray powder diffraction pattern having characteristic peaks expressed in degrees 2-Theta at angles of 19.8°+/−0.3° and 17.5°+/−0.3° and 14.8°+/−0.3 and 23.5°+/−0.3°. In still another embodiment, polymorph form $S_B$ exhibits an X-ray powder diffraction pattern substantially in accordance with FIG. 10 and Table 7.

In one embodiment, the monohydrochloride of the compound of formula A has the polymorph form $S_C$. Polymorph form $S_C$ is a solvate and can be defined by reference to one or more characteristic signals that result from analytical measurements including, but not necessarily limited to, the X-ray powder diffraction pattern of FIG. 11. Polymorph form $S_C$ can also be defined by reference to one or more of the following characteristic signals:

In one embodiment, polymorph form $S_C$ exhibits an X-ray powder diffraction pattern having characteristic peaks expressed in degrees 2-Theta at angles of 9.9°+/−0.3° and 20.0°+/−0.3°. In another embodiment, polymorph form $S_C$ exhibits an X-ray powder diffraction pattern substantially in accordance with FIG. 11 and Table 8.

In one embodiment, the monohydrochloride of the compound of formula A has the polymorph form $S_D$. Polymorph form $S_D$ is a solvate and can be defined by reference to one or more characteristic signals that result from analytical measurements including, but not necessarily limited to, the X-ray powder diffraction pattern of FIG. 12. Polymorph form $S_D$ can also be defined by reference to one or more of the following characteristic signals:

In one embodiment, polymorph form $S_D$ exhibits an X-ray powder diffraction pattern having characteristic peaks expressed in degrees 2-Theta at angles of 9.9°+/−0.3° and 23.5°+/−0.3°. In another embodiment, polymorph form $S_D$ exhibits an X-ray powder diffraction pattern having characteristic peaks expressed in degrees 2-Theta at angles of 8.1°+/−0.3 and 17.6°+/−0.3°. In yet another embodiment, polymorph form $S_D$ exhibits an X-ray powder diffraction pattern having characteristic peaks expressed in degrees 2-Theta at angles of 9.9°+/−0.3° and 23.5°+/−0.3°, and 8.1°+/−0.3 and 17.6°+/−0.3°. In another embodiment, polymorph form $S_D$ exhibits an X-ray powder diffraction pattern substantially in accordance with FIG. 12 and Table 9.

In one embodiment, the monohydrochloride of the compound of formula A has the polymorph form $S_E$. Polymorph form $S_E$ is a solvate and can be defined by reference to one or more characteristic signals that result from analytical measurements including, but not necessarily limited to, the X-ray powder diffraction pattern of FIG. 13. Polymorph form $S_E$ can also be defined by reference to one or more of the following characteristic signals:

In one embodiment, polymorph form $S_E$ exhibits an X-ray powder diffraction pattern having characteristic peaks expressed in degrees 2-Theta at angles of 4.3°+/−0.3° and 17.6°+/−0.3°. In another embodiment, polymorph form $S_E$ exhibits an X-ray powder diffraction pattern having characteristic peaks expressed in degrees 2-Theta at angles of 7.3°+/−0.3 and 9.9°+/−0.3°. In yet another embodiment, polymorph form $S_E$ exhibits an X-ray powder diffraction pattern having characteristic peaks expressed in degrees 2-Theta at angles of 4.3°+/−0.3° and 17.6°+/−0.3°, and 8.3°+/−0.3 and 9.9°+/−0.3°. In another embodiment, polymorph form $S_D$ exhibits an X-ray powder diffraction pattern substantially in accordance with FIG. 13 and Table 10.

In one embodiment, the polymorph form A contains less than 1% by weight total impurities. In another embodiment, the polymorph form A contains less than 0.5% by weight total impurities. In yet another embodiment, the polymorph form A contains less than 0.1% by weight total impurities.

The term "essentially pure" is understood in the context of the present invention to mean especially that at least 90, preferably at least 95, and most preferably at least 99 percent by weight of the crystals of the compound of formula A, its hydrates, its salts or hydrates or solvates of its salts are present in the specified crystal form according to the invention.

In the context with stating that a crystal form of the compound of formula A, its hydrates, its salts or the hydrates or solvates of its salts exhibits an X-ray diffraction diagram essentially as outlined in one of the Figures, the term "substantially" means that at least the major lines of the diagram depicted in said Figure, i.e., those having a relative line intensity of more than 20%, especially more than 30%, as compared to the most intense line in the diagram, have to be present.

In one preferred embodiment, the crystal form of the compound of formula A, its hydrates, its salts or its hydrates or solvates of its salts exhibits an X-ray diffraction diagram substantially as outlined in one of the Figures.

Of particularly high preference are solid, preferably crystalline, form of the compound of formula A, or hydrates, its salts or the hydrates or solvates of its salts obtainable as described in the Examples. The term "solid form" according to the present invention includes crystalline forms. Preferred solid forms are crystalline forms.

The present invention relates also to a process for the preparation of specific solid, preferably crystalline, forms of the compound of formula A, its hydrates, its salts and hydrates or solvates of its salts. The precise conditions under which such specific solid forms are formed may now be empirically determined and a number of methods are suitable in practice, including the process for manufacturing a compound of formula 5 as described herein and with the additional conditions described in Examples 4 to 12 herein.

In another aspect, the invention also provides a method of treating conditions, disorders or diseases mediated by the activation of PI3K, such as indicated above, in a subject in need of such treatment, which method comprises administering to said subject an effective amount of a solid form, preferably crystalline, form of the compound of formula A or its monohydrochloride salt. The solid form of the compound of formula A or its monohydrochloride salt that can be used for such treatment includes those described herein, including but not limited to polymorphs Form $H_A$ and Form A anhydrous of the compound of Formula A and polymorph Form Ha, Form A, Form B, Form $S_A$, Form $S_A$, Form $S_B$, Form $S_C$, Form $S_D$, and Form $S_E$ of the monohydrochloride salt of the compound of Formula A. Preferred is polymorphs Form $H_A$ and Form A anhydrous of the compound of Formula A and polymorph Form Ha, Form A, and Form B $S_E$ of the monohydrochloride salt of the compound of Formula A. Most preferred is Form A of the monohydrochloride salt of the compound of Formula A.

The solid, preferably crystalline, forms of the compound of formula A, its hydrates, its salts and hydrates or solvates of its salts may preferably be used in the treatment of cellular proliferative diseases such as tumor and/or cancerous cell growth mediated by PI3K. In particular, the compounds of formula A, its hydrates, its salts and hydrates or solvates of its salts are useful in the treatment of human or animal (e.g., murine) cancers, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

In one embodiment, the invention relates to the use of polymorph Form A of 5-(2,6-Di-4-morpholinyl-4-pyrimidinyl)-4-trifluoromethylpyridin-2-amine monohydrochloride in the treatment of cancer.

The invention relates especially to polymorph Form A of 5-(2,6-Di-4-morpholinyl-4-pyrimidinyl)-4-trifluoromethylpyridin-2-amine monohydrochloride in the treatment of one of the said diseases mentioned herein or in the preparation of a pharmaceutical composition for the treatment thereof in a subject in need of such treatment.

In one embodiment, the invention relates to the use of a crystalline compound of formula A or its monohydrochloride salt, especially Form A of the monohydrochloride salt, for the preparation of a medicament for the treatment of disorders mediated by PI3K. In one embodiment of the use, the disorder is a cellular proliferative disease, such as the disorders listed above.

In another embodiment, the invention relates to the use of a crystalline compound of formula A or its monohydrochloride salt, especially Form A of the monohydrochloride salt, and a pharmaceutically acceptable carrier or diluent, for use in the treatment of cancer.

The invention relates also to a method for the treatment of warm-blooded animals, including humans, suffering from said diseases, wherein a quantity of the solid, preferably crystalline, form of the compound of formula A, its hydrates, its salts or hydrates or solvates of its salts which is effective against the disease concerned, especially a quantity with antiproliferative efficacy, is administered to warm-blooded animals in need of such treatment.

"Treating" within the context of the present invention, means an alleviation of symptoms associated with a disorder or disease, or halt of further progression or worsening of those symptoms, or prevention or prophylaxis of the disease or disorder. For example, within the context of treating patients in need of an inhibitor of PI3K, successful treatment may include a reduction in the proliferation of capillaries feeding a tumor or diseased tissue, an alleviation of symptoms related to a cancerous growth or tumor, proliferation of capillaries, or diseased tissue, a halting in capillary proliferation, or a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. The compounds of the invention can also be administered in conjunction with other anti-cancer drugs including those used in antisense and gene therapy.

As used herein, "treat" and "treatment" are interchangeable terms as are "limiting" and "treating" and, as used herein, include preventative (e.g., prophylactic) and palliative treatment or the act of providing preventative or palliative treatment.

The terms "PI3K-mediated disorder" and "disorder mediated by PI3K" refer to a disorder that can be beneficially treated by the inhibition of PI3K.

The term "cellular proliferative diseases" refers to diseases including, for example, cancer, tumor, hyperplasia, restenosis, cardiac hypertrophy, immune disorder and inflammation.

The term "cancer" refers to cancer diseases that can be beneficially treated by the inhibition of PI3K, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

The solid, preferably crystalline, forms of the compound of formula A, its hydrates, its salts or hydrates or solvates of its salts described herein can be utilized to prepare stable pharmaceutical dosage forms. Hence, the invention relates also to pharmaceutical compositions which contain an amount, especially a therapeutically effective amount for the treatment of one of the diseases mentioned herein, of the solid, preferably crystalline, form of the compound of formula A, its hydrate, its salts, or the hydrate or solvate of its salts, along with other pharmaceutically acceptable excipients, carriers, fillers, diluents and the like.

As used herein, the language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1% to 99.9% (more preferably, 0.5 to 90%) of active ingredient in combination with a pharmaceutically acceptable carrier.

The compounds may be used alone or in compositions together with a pharmaceutically acceptable carrier or excipient. Pharmaceutical compositions of the present invention comprise a therapeutically effective amount of a phosphatidylinositol 3-kinase inhibitor compound described herein formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

The compounds of the present invention may be administered to humans and other animals orally, parenterally, sublingually, by aerosolization or inhalation spray, rectally, intracisternally, intravaginally, intraperitoneally, bucally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Methods of formulation are well known in the art and are disclosed, for example, in *Remington: The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-propanediol or 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled.

Examples of other biodegradable polymers include poly(orthoesters) and poly(anhydrides). Depot injectable formulations may also be prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5 µm. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 µm. Predominantly in this application means that at least 70% but preferably more than 90% of all generated aerosol particles are within 1-5 µm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, Calif.), SIDESTREAM nebulizers (Medic-Aid Ltd., West Sussex, England), PARI LC and PARI LC STAR jet nebulizers (Pari Respiratory Equipment, Inc., Richmond, Va.), and AEROSONIC (DeVilbiss Medizinische Produkte (Deutschland) GmbH, Heiden, Germany) and ULTRAAIRE (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq Effective amounts of the compounds of the invention generally include any amount sufficient to detectably inhibit PI3K activity by any of the assays described herein, by other PI3K activity assays known to those having ordinary skill in the art, or by detecting an inhibition or alleviation of symptoms of cancer. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

According to the methods of treatment of the present invention, tumor growth is reduced or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat tumor growth, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose. In general, treatment regimens according to the present invention comprise administration to a patient in need of such treatment from about 10 mg to about 2000 mg of the compound(s) of this invention per day in single or multiple doses.

The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

The present pharmaceutical preparations which, if so desired, may contain further pharmacologically active substances, are prepared in a manner known per se, for example by means of conventional mixing, granulating, coating, dissolving or lyophilising processes, and contain from about 1% to 100%, especially from about 1% to about 20%, of the active substance or substances.

The present invention relates also to a process for the preparation of a pharmaceutical composition which comprises mixing a solid, preferably crystalline, form of the compound of formula A, its hydrates or solvates, its salts or hydrates or solvates of its salts of the invention together with at least one pharmaceutically acceptable carrier or diluent.

In another aspect of the invention, kits that include one or more compounds of the invention are provided. Representative kits include a PI3K inhibitor compound of the invention (e.g., a compound of formula 5) and a package insert or other labeling including directions for treating a cellular proliferative disease by administering a PI3K inhibitory amount of the compound.

The term "kit" as used herein comprises a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

The kits of the present invention may also comprise, in addition to a PI3K inhibitor, one or more additional pharmaceutically active compounds. Preferably, the additional compound is another PI3K inhibitor or another compound useful to treat cancer, angiogenesis, or tumor growth. The additional compounds may be administered in the same dosage form as the PI3K inhibitor or in different dosage forms. Likewise, the additional compounds can be administered at the same time as the PI3K inhibitor or at different times.

EXAMPLES

The following examples illustrate the invention without limiting the scope thereof. It is understood that the invention is not limited to the embodiments set forth herein, but embraces all such forms thereof as come within the scope of the disclosure.

Example 1

4,4'-(6-Chloropyrimidine-2,4-diyl)di[morpholine] (3)

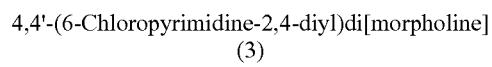

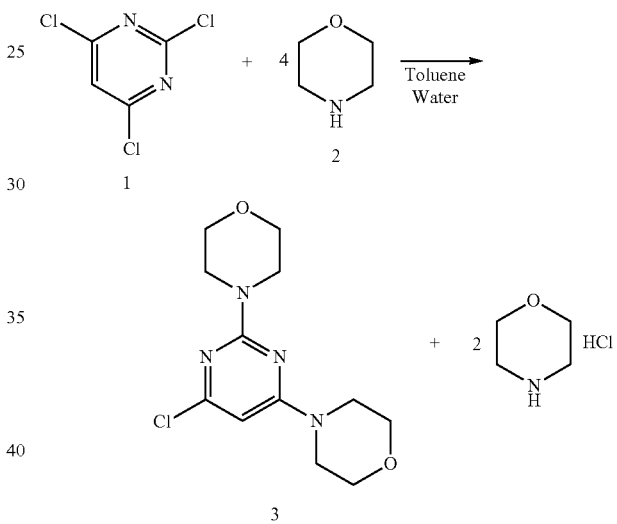

Prepare a solution of 22 g (0.12 mol) of 2,4,6-trichloropyrimidine 1, in 95.2 g (110 mL) of toluene and charge it to the 125 mL addition funnel. Charge a nitrogen-flushed 500 mL round bottom 4-neck flask that equipped with a condenser, heating mantle, thermocouple, 125 mL addition funnel, mechanical stirrer and nitrogen inlet/outlet with 62.7 g (63 mL, 0.72 mol) of morpholine 2, 95.2 g (110 mL) of toluene and 44 g (44 mL) of water. Add the toluene solution of 1 over 10 minutes. Heat the reaction mixture to 83±3° C. Stir at 83±3° C. for 2 h. Check the progress of the reaction. Cool to 30±3° C. Transfer the 2-phase mixture to a 1 L separatory funnel. Separate the phases. Wash the organic phase (top) twice with 200 mL (2×100 mL) of warm (30° C.) water. Separate the phases after each wash. Transfer the organic (top) phase back to the 500 mL reaction flask that equipped with a condenser, heating mantle, thermocouple, 125 mL addition funnel, mechanical stirrer and nitrogen inlet/outlet. Stir and add 50.0 mL of 10.0 N aqueous hydrochloric acid solution. Heat the solution to 53±3° C. and stir for 12-18 h. Check the progress of the reaction. Cool to 22±3° C. Transfer the 2-phase mixture to a 1 L separatory funnel. Separate the phases. Transfer the aqueous (bottom) phase to a 500 mL round bottom 4-neck flask equipped with a cooling bath,

Example 2

4,4'-[6-(4,4,5,5-Tetramethyl-1,3,2-dioxaborolan-2-yl)pyrimidine-2,4-diyl]di[morpholine] (4)

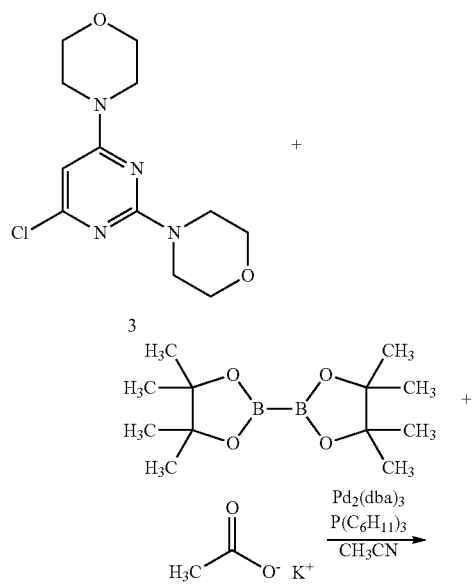

Charge a nitrogen-flushed 2 L round bottom 4-neck flask that equipped with a condenser, heating mantle, thermocouple, rubber septum, mechanical stirrer and nitrogen inlet/outlet with 100.0 g (0.351 mol) of 4,4'-(6-chloropyrimidine-2,4-diyl)di[morpholine] 3 and 943 g (1200 mL) of acetonitrile. Stir and heat to 60±3° C. Hold this solution at 60±3° C. for charge to batch. Charge a nitrogen-flushed 3 L reactor that equipped with an overhead stirrer, condenser, nitrogen inlet/outlet and rubber septum with 115.9 g (0.457 mol) of bis(pinacolato)-diboron, 51.7 g (0.527 mol) of potassium acetate, 12.9 g (0.014 mol) of tris(dibenzylideneacetone)-dipalladium(0), 7.9 g (0.029 mol) of tricyclohexylphosphine and 393 g (500 mL) of acetonitrile. Stir and heat the slurry to 84±3° C. (reflux). Collect 100 mL of distillate. Transfer the warm 3 acetonitrile solution via peristaltic pump to the 3 L reactor containing the reaction mixture over 30 minutes and continue collecting distillate. Wash the 2 L flask and transfer lines with 79 g (100 mL) of acetonitrile and transfer the wash to the batch. Maintain distillation at 84±3° C. and collect an additional 900 mL of distillate (batch volume ~1100 mL). Check the progress of the reaction 2 h from the start of the addition of 3. Cool the reaction mixture to 70±3° C. and charge 693 g (800 mL) of toluene over 1-2 min. The batch will cool upon the addition of the toluene. Further cool the reaction mixture to 50±3° C. Charge to a clean 1 L flask, 347 g (400 mL) of toluene and warm it to 50° C. This will be used as the cake wash. Filter the reaction mixture through a 15 g pad of Celite 545. Wash the filter cake with the warm (50° C.) toluene (400 mL) and collect this wash separately from the batch. This wash will be charged to the distillation residue later in the process. Transfer the filtrate back to the 3 L reactor. Concentrate the batch (25° C. to 40° C. internal temperature, 50 mbar) until a batch volume of 250 mL is reached. Charge toluene cake wash held in reserve (~400 mL) and continue to concentrate the batch (37° C. to 43° C. internal temperature, 50 mbar) until a batch volume of 250 mL is reached. Check for complete removal of acetonitrile using the described Process Steering Control. Warm to 50° C. and stir for 15 min. Add 164 g (240 mL) of heptane over 30 minutes maintaining 50° C. throughout the addition. Stir the resulting suspension for 1 h. Cool the slurry to 23±3° C. over 1 h and hold at this temperature for at least 1 h. Blanket the filtering funnel used for isolation of the product with nitrogen (to avoid moisture) and quickly filter the solids. Wash the filter cake twice with a mixture of 22 g (25 mL) of toluene and 51 g (75 mL) of heptane. Dry the solids at 50° C., 35 mbar for 16 h to afford 114.4 g (72.7% corrected yield) of 4 as a sandy, beige solid.

Example 3

5-Bromo-4-(trifluoromethyl)pyridin-2-amine (4a)

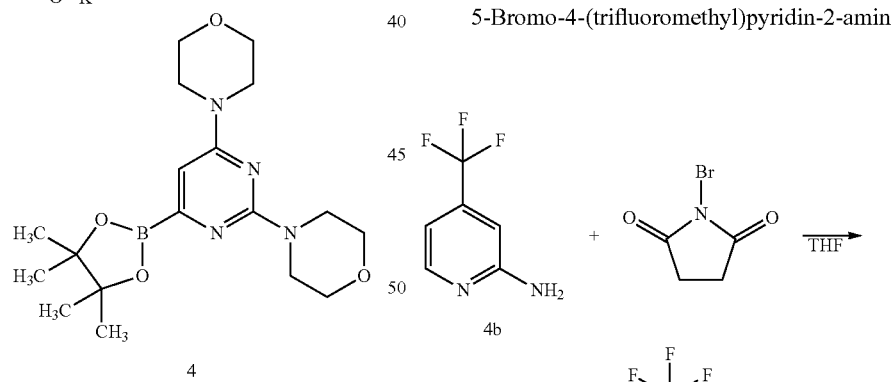

Charge a nitrogen-flushed 3 L reactor that equipped with an overhead stirrer, condenser, nitrogen inlet/outlet and rubber septum with 112.14 g (0.63 mol) of N-bromosuccinimide (NBS) and 645 g (725 mL) of tetrahydrofuran. Stir and cool the slurry to −5±3° C. Charge a nitrogen-flushed 1 L round bottom 4-neck flask that equipped with a thermocouple, mechanical stirrer and nitrogen inlet/outlet with 97.26 g (0.6 mol) of 2-amino-4-(trifluoromethyl)pyridine, 4b and 511 g (575 mL) of tetrahydrofuran. Stir to dissolve the 4b. Transfer the 4b solution to the addition funnel on the reactor and add the solution to the NBS slurry over 2 h maintaining an internal temperature of 0±3° C. throughout the addition. Rinse the 1 L flask and addition funnel with 44 g (50 mL) of tetrahydrofuran and add the wash to the reaction mixture. Warm the solution to 20±3° C. over 30 minutes. Check for completeness of the reaction. Quench by charging a solution of 24.6 g of sodium thiosulfate pentahydrate dissolved in 475 mL of water over 10 minutes, maintaining a batch temperature of 20±3° C. throughout the addition. Stir for 1 h after the quench. Concentrate (internal temp=25° C., 50 mbar) to remove tetrahydrofuran. Add 379 g (500 mL) of tert-butyl methyl ether. Stir and warm the resulting solution/suspension to 30±3° C. and stir for 15 minutes. Separate the phases. Wash the extract four times with a solution of 32 g of sodium chloride dissolved in 768 g (768 mL) of water (4×200 mL per wash), separating the phases after each wash. Finally, wash the extract with 150 g (150 mL) of water. Separate the phases. Charge 152 g (200 mL) of tert-butyl methyl ether. Partially concentrate (57±3° C.) to a volume of 350 mL. Cool to 50° C. and add 265 g (350 mL) of tert-butyl methyl ether. Resume the concentration (57±3° C.) until a batch volume of 350 mL is reached. Cool to 50° C. and add 265 g (350 mL) of tert-butyl methyl ether. Again, resume the concentration (57±3° C.) until a batch volume of 350 mL is reached. Cool to 50° C. and add 103 g (150 mL) of tert-butyl methyl ether to raise the batch volume to 500 mL. Charge 1026 g (1500 mL) of heptane over 15 minutes maintaining 45±3° C. throughout the addition. Slowly increase the vacuum and concentrate (internal temp=40° C. to 50° C.) to a batch volume of 1000 mL. Release the vacuum and seed the batch. Resume the distillation, further increase the vacuum (slowly) and concentrate (internal temp=25° C. to 40° C.) to a batch volume of 500 mL. Stir the resulting suspension at 0° C. for 30 min. Filter the solids. Wash the filter cake with 68 g (100 mL) of cold (0° C.) heptane (containing 30 ppm Octastat). Dry the solids (40° C., 50 mbar) for 16 h to afford 109.8 g (78.0% yield) 4a as an orange solid.

Example 4

5-(2,6-Di-4-morpholinyl-4-pyrimidinyl)-4-trifluoromethylpyridin-2-amine (5)

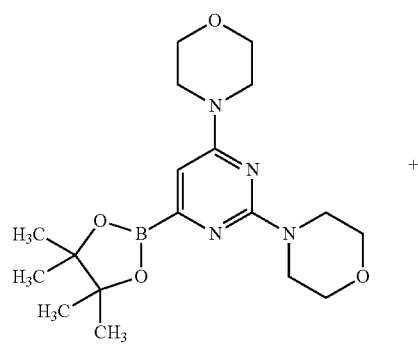

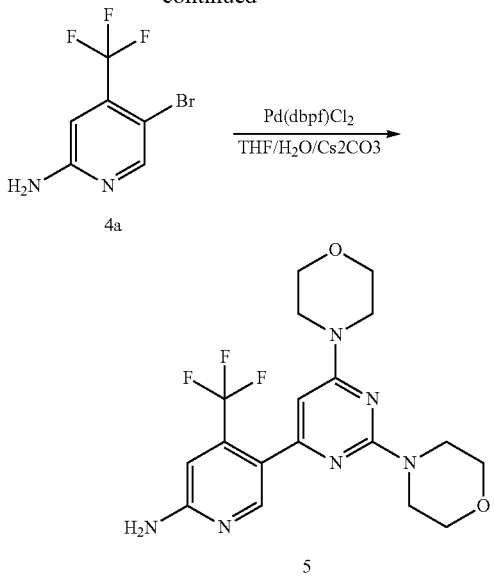

Charge a 500 mL round bottom 3-neck flask that equipped with a thermocouple, mechanical stirrer, nitrogen inlet/outlet and cooling bath with 202.8 g (0.622 mol) of cesium carbonate and 260 g (260 mL) of water. Stir and cool the resulting solution to 22±3° C. Transfer the solution to the addition funnel. Charge a nitrogen-flushed 3 L reactor that equipped with an overhead stirrer, condenser, pH probe, nitrogen inlet/outlet and 500 mL addition funnel with 50.0 g (0.207 mol) of 5-bromo-4-(trifluoromethyl) pyridin-2-amine 4a, 190.9 g (0.456 mol) of 4,4'-[6-(4,4,5,5-tetramethyl-1,3,2-dioxaborolan-2-yl)pyrimidine-2,4-diyl]di[morpholine]-4, 6.75 g (0.0103 mol) of 1,1'-bis(di-tert-butylphosphino) ferrocene palladium dichloride and 556 g (625 mL) of thf. Stir the slurry at 22±3° C. Add the aqueous cesium carbonate solution via the addition funnel to the slurry over 1-2 min. Stir rapidly (to ensure good mixing), heat to 45±3° C. over 15 min and hold at this temperature for at least 30 minutes. Check for completeness of the reaction. Cool to 22±3° C. Separate the phases. Partially concentrate the THF (25° C., 90 mbar) to a volume of 400 mL. Add 654 g (750 mL) of isopropyl acetate, resume the vacuum distillation and concentrate to a volume of 400 mL. Add 610 g (700 mL) of isopropyl acetate, stir and filter the hazy solution through a 25 g pad of Celite. Wash the reactor and filter cake with 87 g (100 mL) of isopropyl acetate and add the wash to the batch. Add 1 L of 0.125N aqueous N-acetyl-L-cysteine solution and stir at 60±3° C. for 1 h. Cool to 22±3° C. and drain the aqueous wash. Add 1 L of 0.25N aqueous N-acetyl-L-cysteine pH=7 solution and stir at 60±3° C. for 1 h. Cool to 22±3° C. and drain the aqueous wash. Again, add 1 L of 0.25N aqueous N-acetyl-L-cysteine pH=7 solution and stir at 60±3° C. for 1 h. Cool to 22±3° C. and drain the aqueous wash. Charge 34.5 g of Si-Thiol functionalized silica gel and stir the suspension at 60±3° C. for 1 h. Cool to 22±3° C. and filter to remove the silica gel. Add 1 L of 1N aqueous hydrochloric acid solution and stir for 15 minutes. Separate the phases and retain the aqueous phase which now contains product. Extract the organic phase again by adding 500 mL of 1N aqueous HCl solution and stirring for 15 minutes. Separate the phases and combine the aqueous extracts. Adjust the pH to 2.3±0.2 by the addition of ~280 mL of 4N aqueous sodium hydroxide solution. Charge 17.2 g of Si-Thiol functionalized silica gel and stir the suspension at 50±3° C. for 1 h. Cool to 22±3° C. and filter to remove the silica gel. Adjust the pH to 5.0±0.2 by the slow addition of ~75 mL of 4N aqueous sodium hydroxide solution maintaining a batch temperature of 15±3° C. Stir the slurry for at least 16 h at 22±3° C. to allow the product to completely solidify. Filter the solids and wash the filter cake once with 250 g (250 mL) of water. Dry the solids (50° C., 35 mbar) for 16 h to obtain 75 g (89% yield) of 5 as a tan solid. Following this procedure, Compound 5 is the hemihydrate polymorph form $H_A$ of the Compound of Formula A.

Alternative Procedure:

Charge a 500 mL round bottom 3-neck flask that equipped with a thermocouple, mechanical stirrer, nitrogen inlet/outlet and cooling bath with 202.8 g (0.622 mol) of cesium carbonate and 260 g (260 mL) of water. Stir and cool the resulting solution to 22±3° C. Transfer the solution to the addition funnel. Charge a nitrogen-flushed 3 L reactor that equipped with an overhead stirrer, condenser, pH probe, nitrogen inlet/outlet and 500 mL addition funnel with 50.0 g (0.207 mol) of 5-bromo-4-(trifluoromethyl) pyridin-2-amine 4a, 190.9 g (0.456 mol) of 4,4'[6(4,4,5,5tetramethyl-1,3,2dioxaborolan2-yl)pyrimidine-2,4-diyl]di[morpholine]-4, 6.75 g (0.0103 mol) of 1,1'-bis(di-tert-butylphosphino) ferrocene palladium dichloride and 556 g (625 mL) of tetrahydrofuran. Stir the slurry at 22±3° C. Add the aqueous cesium carbonate solution via the addition funnel to the slurry over 1-2 min. Stir rapidly (to ensure good mixing), heat to 45±3° C. over 15 min and hold at this temperature for at least 30 minutes. Check for completeness of the reaction. Cool to 22±3° C. Separate the phases. Partially concentrate the THF (25 C, 90 mbar) to a volume of 400 mL. Add 654 g (750 mL) of isopropyl acetate, resume the vacuum distillation and concentrate to a volume of 400 mL. Add 610 g (700 mL) of isopropyl acetate, stir and filter the hazy solution through a 25 g pad of Celite. Wash the reactor and filter cake with 87 g (100 mL) of isopropyl acetate and add the wash to the batch. Add 1 L of 0.125N aqueous N-acetyl-L-cysteine solution and stir at 60±3° C. for 1 h. Cool to 22±3° C. C and drain the aqueous wash. Add 1 L of 0.25N aqueous N-acetyl-L-cysteine pH=7 solution and stir at 60±3° C. for 1 h. Cool to 22±3° C. and drain the aqueous wash. Again, add 1 L of 0.25N aqueous N-acetyl-L-cysteine pH=7 solution and stir at 60±3° C. for 1 h. Cool to 22±3° C. and drain the aqueous wash. Charge 34.5 g of Si-Thiol functionalized silica gel and stir the suspension at 60±3° C. for 1 h. Cool to 22±3° C. and filter to remove the silica gel. Add 1 L of 1N aqueous hydrochloric acid solution and stir for 15 minutes. Separate the phases and retain the aqueous phase which now contains product. Extract the organic phase again by adding 500 mL of 1N aqueous hydrochloric acid solution and stirring for 15 minutes. Separate the phases and combine the aqueous extracts. Adjust the pH to 2.3±0.2 by the addition of ~280 mL of 4N aqueous sodium hydroxide solution. Charge 17.2 g of Si-Thiol functionalized silica gel and stir the suspension at 50±3° C. for 1 h. Cool to 22±3° C. and filter to remove the silica gel. Adjust the pH to 5.0±0.2 by the slow addition of ~75 mL of 4N aqueous sodium hydroxide solution maintaining a batch temperature of 15±3° C. Stir the slurry for at least 16 h at 22±3° C. to allow the product to completely solidify. Filter the solids and wash the filter cake once with 250 g (250 mL) of water. Dry the solids (50° C., 35 mbar) for 16 h to obtain 75 g (89% yield) of 5 as a tan solid. Following this procedure, Compound 5 is the hemihydrate polymorph form $H_A$ of the Compound of Formula A.

Example 5

5-(2,6-Di-4-morpholinyl-4-pyrimidinyl)-4-(trifluoromethyl)pyridin-2-amine monohydrochloride (6)

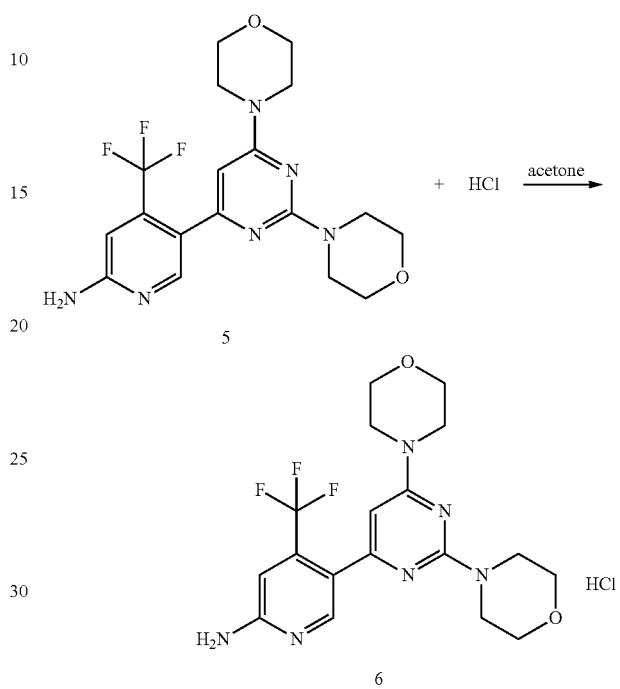

Charge a nitrogen-flushed 3 L reactor that equipped with an overhead stirrer, condenser, nitrogen inlet/outlet and 500 mL addition funnel with 51.3 g (0.125 mol, 1 eq.) of 5 and 247 g (312 mL) of acetone. Stir the slurry at 25° C. for 15 minutes. Filter through Celite (2-5 g). Wash the reactor and filter cake with 30 g (37 mL) of acetone and combine the wash with the filtrate. Rinse the reactor with methanol and dry it with heat and vacuum. Cool the reactor and re-charge the filtrate. Warm the solution to 50° C. Add a solution of 25.7 mL (0.125 mol, 1.03 eq.) of 5 N hydrogen chloride in isopropanol and 198 g (250 mL) of acetone over 2 h. Seed after the first 5% of the acid solution has been added (about 25 mL). Maintain temperature for 15 min. Cool to 10° C. and filter the solids. Wash the filter cake with 47 g (60 mL) of acetone and dry the solids at 50° C., 35 mbar for 16 h to afford 49.4 g (88.1% yield) of 6 as a yellow, crystalline solid. Following this procedure, Compound 6 is polymorph Form A of the monohydrochloride salt of the Compound of Formula A.

Example 6

5-(2,6-Di-4-morpholinyl-4-pyrimidinyl)-4-(trifluoromethyl)pyridin-2-amine monohydrate monohydrochloride Charge a nitrogen-flushed 2 L reactor that equipped with an overhead stirrer, condenser, nitrogen inlet/outlet and 500 mL addition funnel with 82.08 g (0.20 mol, 1 eq.) of 5 and 792 g (1.0 L) of acetone. Stir the slurry at 25° C. for 15 minutes. Add a solution of 34.3 mL (0.206 mol, 1.03 eq.) of 6 N hydrogen chloride in water. Add 3 mg of seed. Solids formed. Add 20 mL of water. Heat the batch to reflux (55-56° C.) and maintain at reflux for 15 minutes. Cool to 20° C. over 1.5 h. Cool to 5° C. over 1 h and filter the solids. Wash the filter cake with 80 mL of 5° C. acetone and dry the solids at 40° C., 35 mbar for 16 h to afford 70.4 g (75.7% yield) of the title compound as a yellow, crystalline solid. Following this procedure, the resulting compound is the monohydrate of the monohydrochloride salt (Polymorph Form IIa) of the Compound of Formula A.

Comparative Data

Manufacture of 4,4'(6-Chloropyrimidine-2,4-diyl)di [morpholine]

|  | this invention | WO2007/0084786 |
|---|---|---|
| yield/selectivity | 91%/93% | 85%/87% |
| ease of isolation | simple | Chromatography |

Manufacture of 5-(2,6-Di-4-morpholinyl-4-pyrimidinyl)-4-(trifluoromethyl)pyridine-2-amine monohydrochloride

Figure 2:
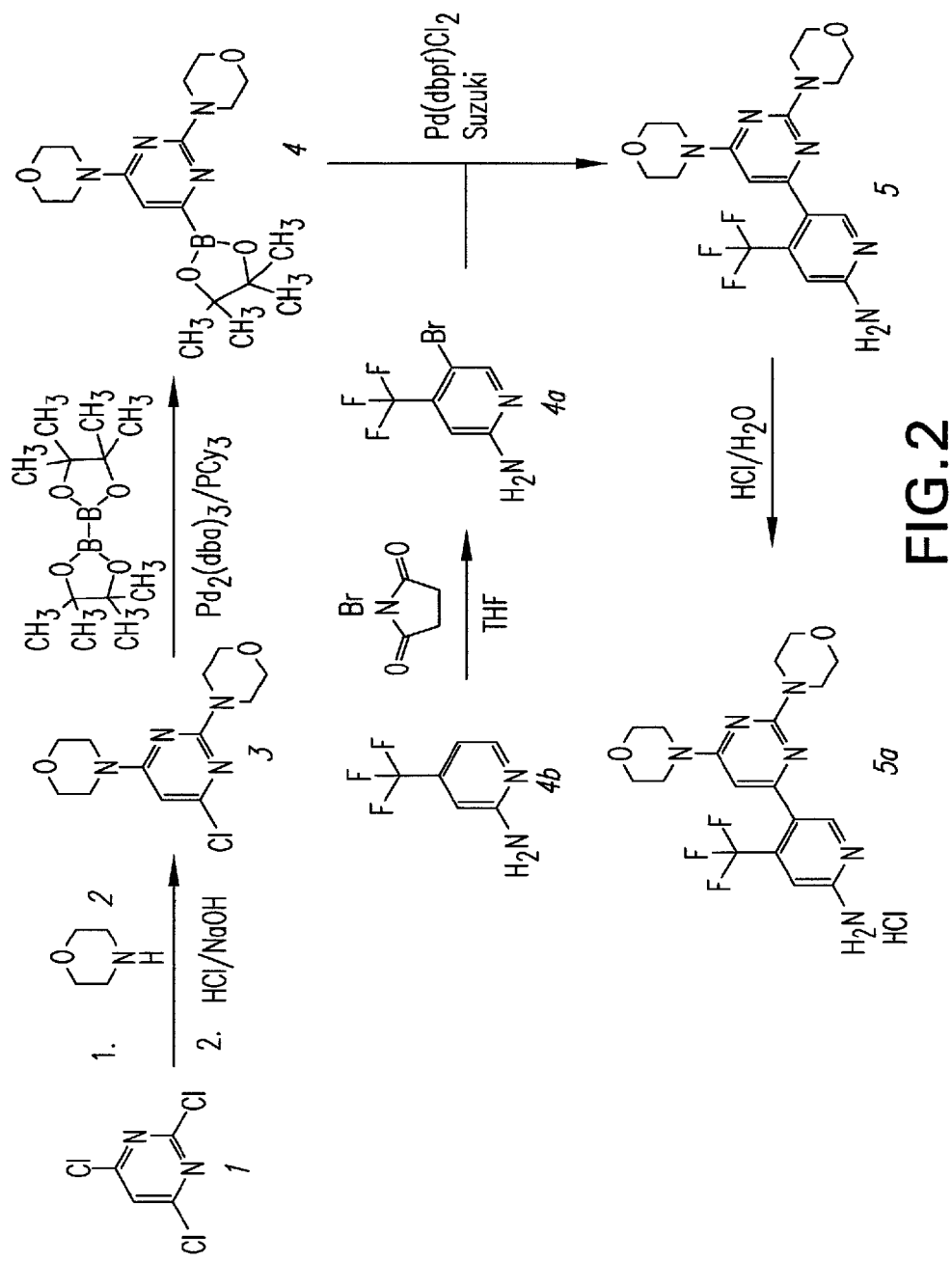
FIG. 2 shows a process according to the invention for the specific compound 5-(2,6-Di-4-morpholinyl-4-pyrimidinyl)-4-trifluoromethylpyridin-2-amine.
Figure 3:
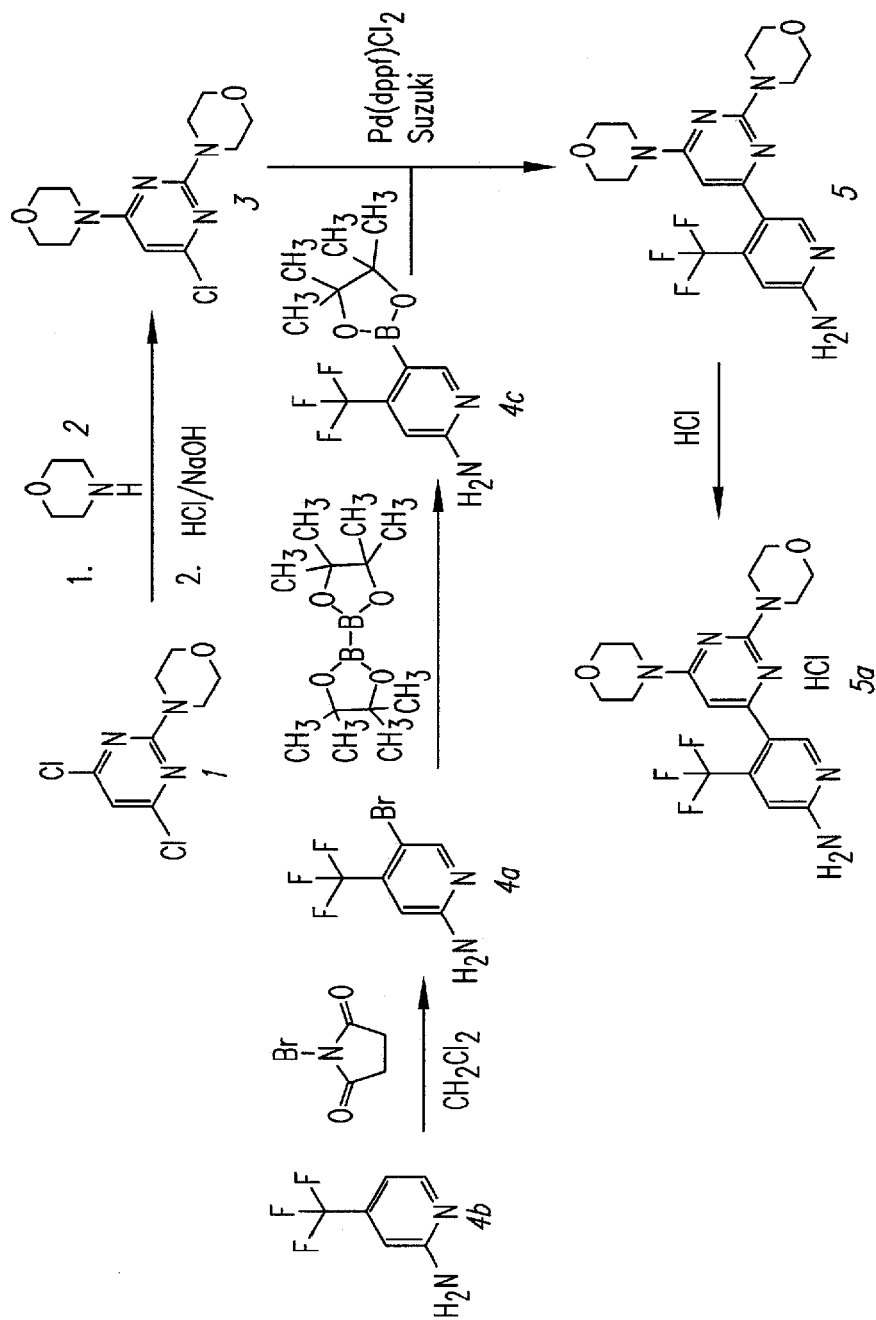
FIG. 3 shows a known process for the same compound 5-(2,6-Di-4-morpholinyl-4-pyrimidinyl)-4-trifluoromethyl-pyridin-2-amine.

|  | this invention | WO2007/0084786 |
|---|---|---|
| process | according to FIG. 2 | according to FIG. 3 |
| yield | 39% | 4.5% |
| ease of isolation | simple, no chromatographic purification, direct precipitation | difficult, contains chromatographic purification steps |
| costs | inexpensive starting material | expensive starting material |

Example 7

Preparation of N-(5-bromo-4-(trifluoromethyl)pyridin-2-yl)acetamide (B2)

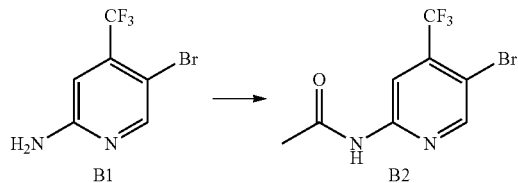

Version A

A dry vessel under nitrogen at room temperature was charged with 5-bromo-4-(trifluoromethyl)pyridin-2-amine B1 (200 g, 830 mmol) and ethyl acetate (200 ml). The reaction mixture was cooled to 0° C. To the solution was added N,N-dimethylpyridin-4-amine (1.01 g, 8.29 mmol). Heptane (400 ml) was added and the mixture was cooled to 0° C. Acetic anhydride (109.6 ml, 1162 mmol) was added over a period of 60 min. The reaction mixture was warmed to 50° C. within 60 min. The reaction mixture was stirred at 50° C. for 18 h. Solvent (330 g) was removed by distillation (540-250 mbar, 50° C.) until a residue of ~300 ml was obtained. The reaction mixture was allowed to cool to 20° C. Heptane (800 ml) was added and the mixture was stirred for 30 min. The precipitate was collected by filtration. The filter cake was washed with heptane (100 ml). The product was dried in a tray dryer for 16 h at 40° C., <20 mbar to yield 212 g (90%) B2 as slightly brown solid.

Version B

A reactor was charged with 5-bromo-4-(trifluoromethyl)pyridin-2-amine (197.04 g, 817.564 mmol) and N,N-dimethylpyridin-4-amine (0.999 g, 8.176 mmol). Ethyl acetate (200 ml) was added and the mixture was stirred for 10 min. Heptan (400 ml) was added. The mixture was warmed to 80° C. within 20 min. Acetic anhydride (107.994 ml, 1144.590 mmol) was continuously added within 4 h. The reaction mixture was stirred at 80° C. until starting material was not detected anymore. Solvent was removed by distillation (80° C., 700-450 mbar) until a residual volume of 300 ml was obtained. The mixture was cooled to 0° C. Heptane (800 ml) was added and the mixture was stirred at 0° C. over night. The product was collected by filtration. The residue was washed with heptane (100 ml) and dried in a tray dryer for 16 h at 40° C., <20 mbar to yield 215 g (92%) B2 as slightly brown solid.

Example 8

Preparation of 6-acetamido-4-(trifluoromethyl)pyridin-3-ylboronic acid (B3)

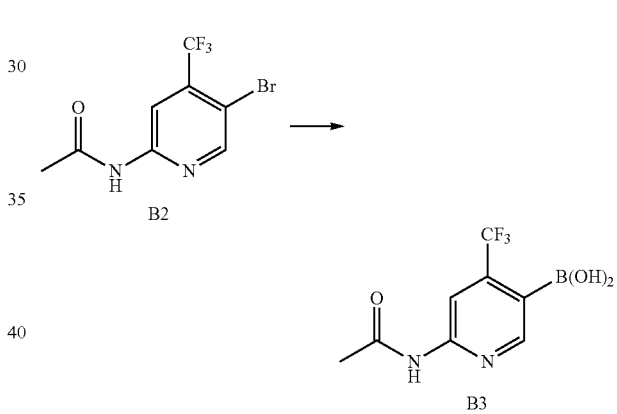

Process Version A

A reactor was charged with 25.6 g Lithium amide and 60 ml THF at 20° C. A solution of 60.0 g N-(5-bromo-4-(trifluoromethyl)pyridin-2-yl)acetamide B2 in 280 ml THF was added within 30 min at 0° C. The suspension was stirred at 20° C. for 4.5 h. The residual Lithium amide was removed by filtration. The filter cake was washed with 240 ml THF. The solvent was removed by distillation (30° C., 250-85 mbar) to a residual volume of 290 mL. 360 ml THF were added. The solvent was removed by distillation (30° C., 180-85 mbar) to a residual volume of 200 mL. 160 ml THF were added. The reaction mixture was cooled to −78° C. and 93.3 ml nBuLi (2.5 M in Hexane) were added within 4 h at −78≤T≤−75° C. A solution of 87.7 g Triisopropylborate in 30 ml THF was added within 30 min at −78≤T≤−75° C. ° C. The reaction mixture was stirred at −78° C. for 30 min. The reaction mixture was warmed to 20° C. within 4 h and stirred at 20° C. for 30 min. 15.3 g water were added within 30 min at 20° C. 45.4 ml HCl (5-6 N in iPrOH) were added within 15 min at 20° C. The reaction mixture was stirred for 15 min at 20° C. 480 ml Toluene were added. The solvent was removed by distillation (30° C., 150-60 mbar) until a remaining volume of 360 ml remained. 480 ml Toluene were added. The solvent was removed by distillation (30° C., 150-60 mbar) until a remaining volume of 360 ml remained. 480 ml Toluene were added. The solvent was removed by distillation (30° C., 150-60 mbar) until a remaining volume of 360 ml remained.

600 ml 2-Butanone were added within 10 min at 30° C. The reaction mixture was stirred at 30° C. for 60 min. The reaction mixture was cooled within 20 min to 20° C. 12.0 g diatomaceous earth (also known as kieselgur) ("HYO") were added. The reaction mixture was stirred at 20° C. for 20 min. The reaction mixture was cooled to 0° C. within 60 min. The reaction mixture was stirred at 0° C. for 60 min. The crude product was collected by filtration. The crude product was washed with 120 ml cold (0° C.) 2-butanone. The crude product was dried in vacuo (30° C., 30-35 mbar) until constant weight was obtained. The crude product was mechanically crushed. The reactor was charged with crude product. 600 ml water was added as fast as possible. The reaction mixture was stirred for 30 min. The pH is >8.5. The side precipitate was removed by filtration.

The precipitate was washed with 120 ml water. The pH of the filtrate is adjusted to pH 3 by addition of 202 g 1N HCl within 10 min. The reaction mixture is cooled to 0° C. within 20 min. The reaction mixture is stirred at 0° C. for 60 min. The product is collected by filtration. The product is washed with 60 ml cold (5° C.) water, The product is dried in vacuo (30° C., 45≤p≤30 mbar) until constant weight is obtained. 31.5 g (59.9%) 6-acetamido-4-(trifluoromethyl)pyridin-3-ylboronic acid B3 were obtained.

Process Version B

To a suspension of Lithium amide (5.6 g, 233.2 mmol) in 140 ml THF was added at room temperature 2-propanol (1.3 g, 21.2 mmol). The reaction mixture was cooled to IT=2° C. A solution of B2 (60.0 g, 212 mmol) in 280 ml THF was added while keeping the temperature at IT 2° C. The reaction mixture was stirred at IT=2° C. for 90 min. THF (240 ml) was added and solvent (~380 ml) was removed by distillation. THF (360 ml) was added and solvent (~380 ml) was removed by distillation. THF (200 ml) was added and the reaction mixture was cooled to IT=−85° C. A solution (76 ml, 190 mmol) nBuLi, 2.5 M in hexane was added at −85° C. followed by addition of a solution of triisopropylborate (31.9 g, 170 mmol) in THF (17 ml). A solution (17.3 ml, 43.3 mmol) n BuLi, 2.5 M in hexane was added at −85° C. followed by addition of a solution of triisopropylborate (23.9 g, 127 mmol) in THF (13 ml). The reaction mixture was allowed to warm to RT and was stirred over night at RT. Water (15.3 g) and HCl in 2-propanol, 5-6 M (36.7 g) was added at RT. Isopropylacetate (480 ml) was added and solvent was removed by distillation until a volume of ~360 ml was obtained. Isopropylacetate (480 ml) was added and solvent was removed by distillation until a volume of ~360 ml was obtained. Isopropylacetate (480 ml) was added and the mixture was cooled to 11=0° C. Water (480 g) was added and by addition of 1N NaOH the pH was adjusted at IT=0° C. to pH 11. The precipitate was removed by filtration. The aquoeus layer was separated at IT=0° C. Water was added and the aquoeus layer was separated at IT=0° C. The combined aquoues layers were cooled to IT=0° C. and the pH was adjusted by addition of 1N HCl to pH 3. The precipitate was collected and the dried at 30° C./40-45 mbar until constant weight was obtained. 48.9 g (93%) 6-acetamido-4-(trifluoromethyl)pyridin-3-ylboronic acid B3 were obtained.

Example 9

5-(2,6-Di-4-morpholinyl-4-pyrimidinyl)-4-trifluoromethylpyridin-2-amine (5)

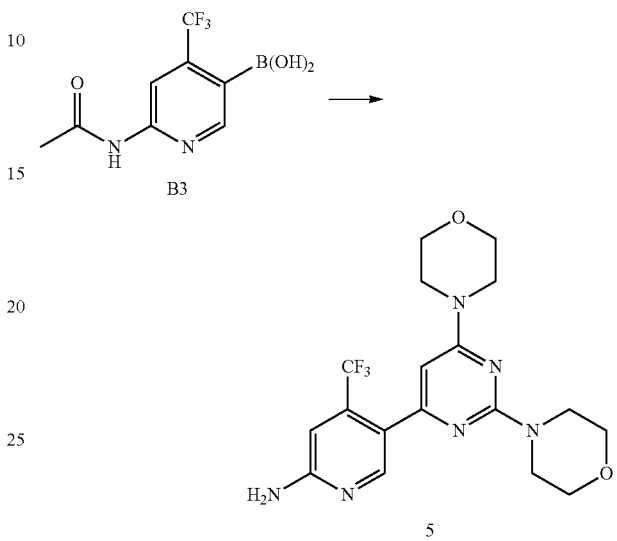

The reactor was charged at 20° C. with 111.7 g 4,4'-(6-chloropyrimidine-2,4-diyl)dimorpholine 3, 108.5 g K₂CO₃ and 4.54 g Tetrakis(Triphenylphosphin)Palladium (0). 125 ml water and 500 ml 1,2-Dimethoxyethan were added. The white suspension was warmed within 30 min to 90° C. A solution of 100 g 6-acetamido-4-(trifluoromethyl)pyridin-3-ylboronic acid B3 in 450 ml 1,2-Dimethoxyethan was constantly added within a period of 4½ h. The funnel was washed with 50 ml 1,2-Dimethoxyethan. The reaction mixture was cooled to 70° C. within 30 min. 1000 ml water were added. 1000 ml solvent was removed by distillation (70° C., 400 mbar to 260 mbar). 1000 ml water was added. 1000 ml solvent was removed by distillation (70° C., 400 mbar to 260 mbar). The reaction mixture was cooled to 20° C. within 30 min. The precipitate was collected by filtration and washed with 300 ml water. The reactor was charged with the precipitate and 1900 g 1N HCl were added. The reaction mixture was warmed to 75° C. within 30 min. The reaction mixture was stirred for 3 h at 75° C. The reaction mixture cooled to 20° C. within 1 h and stirred over night at 20° C. The precipitate was removed by filtration and washed with 200 ml water. The reactor was charged with the filtrate and everything was rinsed with 100 ml water. pH was adjusted to pH11.9. 1800 ml Isopropylacetate were added and the mixture was stirred. The phases were separated and the organic layer was collected. Solvent was removed (70° C., 280 mbar) until the volume was reduced to 725 ml. 1800 ml Isopropylacetate were added and the mixture was stirred. The phases were separated and the organic layer was collected. Solvent was removed (70° C., 280 mbar) until the volume was reduced to 725 ml. The reaction mixture was cooled to 20° C. within 30 min and stored over the week end. The reaction mixture was filtered over a bed of HYO and washed with 225 ml Isopropylacetate. The reactor was charged with the filtrate and 735.5 g of solution 1 (61.2 g N-Acetyl-cystein and 600 g water, pH adjusted to pH 7 with 4 N NaOH) were added. The reaction mixture was warmed to 64° C. within 15 min. The reaction mixture was stirred at 64° C. for 2 h. The reaction mixture was cooled to 20° C. within 45 min. The phases were separated and the aqueous layer was removed. 1926.5 ml 1N HCl were added and the mixture was stirred for 15 min. The phases were separated and the aqueous layer was collected. 947 ml 1N HCl were added and the mixture was stirred for 15 min. The phases were separated and the aqueous layer was collected. The organic layer was removed from the reactor. The reactor was charged with the combined aqueous layers. pH was adjusted to pH 2.3. 39 g Silabond were added. The reaction mixture was warmed to 64° C. within 20 min. The reaction mixture was stirred for 2 h at 64° C. The reaction mixture was coiled to 20° C. within 30 min. The precipitate was removed by filtration. The residue was washed with 500 g water. The reactor was charged with the combined filtrates. pH was adjusted to pH 5.0 with 4 N NaOH The reaction mixture was cooled to 0° C. The reaction mixture was stirred for 60 min. The product was collected by filtration and washed with 500 g cold (~10° C.) water. The product was dried until constant weight was obtained to yield 136.8 g (84.9%) 5-(2,6-Di-4-morpholinyl-4-pyrimidinyl)-4-trifluoromethylpyridin-2-amine 5.

Example 10

Polymorph Form A of 5-(2,6-Di-4-morpholinyl-4-pyrimidinyl)-4-trifluoromethylpyridin-2-amine 40 mg of 5 of Example 4 is equilibrated in 0.5 mL acetonitrile in a vial at 25° C.±0.1 for 24 hours equilibration time (with constant agitation). The resulting solids are collected by filtration, air-dried to remove residual excess solvent and then analyzed by X-ray powder diffraction to yield anhydrous Polymorph Form A of the compound of Formula A.

Example 11

Polymorph Form B of 5-(2,6-Di-4-morpholinyl-4-pyrimidinyl)-4-trifluoromethylpyridin-2-amine monohydrochloride 40 mg of 5-(2,6-Di-4-morpholinyl-4-pyrimidinyl)-4-(trifluoromethyl)pyridin-2-amine monohydrate monohydrochloride of Example 6 is equilibrated in 0.5 mL ethanol in a vial at 25° C.±0.1 for 3 weeks equilibration time (with constant agitation). The resulting solids are collected by filtration, air-dried to remove residual excess solvent and then analyzed by X-ray powder diffraction to yield anhydrous Polymorph Form B of the monohydrochloride salt of the compound of Formula A.

Example 12

Polymorph Form $S_A$ of 5-(2,6-Di-4-morpholinyl-4-pyrimidinyl)-4-(trifluoromethyl)pyridin-2-amine monohydrochloride 40 mg of 5-(2,6-Di-4-morpholinyl-4-pyrimidinyl)-4-(trifluoromethyl)pyridin-2-amine monohydrate monohydrochloride of Example 6 is equilibrated in 0.5 mL acetonitrile in a vial at 25° C.±0.1 for 3 days equilibration time (with constant agitation). The resulting solids are collected by filtration, air-dried to remove residual excess solvent and then analyzed by X-ray powder diffraction to yield Polymorph Form $S_A$ of the monohydrochloride salt of the compound of Formula A.

Example 13

Polymorph Form $S_E$ of 5-(2,6-Di-4-morpholinyl-4-pyrimidinyl)-4-(trifluoromethyl)pyridin-2-amine monohydrochloride 40 mg of 5-(2,6-Di-4-morpholinyl-4-pyrimidinyl)-4-(trifluoromethyl)pyridin-2-amine monohydrate monohydrochloride of Example 6 is equilibrated in 0.4 mL methanol in a vial at 25° C.±0.1 for 24 hours equilibration time (with constant agitation). The solution is evaporated to dryness by nitrogen flow at room temperature. The resulting solid is collected prior to complete dryness and examined by X-ray powder diffraction to yield Polymorph Form $S_E$ of the monohydrochloride salt of the compound of Formula A.

Example 14

Polymorph Form S, of 5-(2,6-Di-4-morpholinyl-4-pyrimidinyl)-4-(trifluoromethyl)pyridin-2-amine monohydrochloride 40 mg of 5-(2,6-Di-4-morpholinyl-4-pyrimidinyl)-4-(trifluoromethyl)pyridin-2-amine monohydrate monohydrochloride of Example 6 is equilibrated in 0.5 mL isopropyl acetate in a vial at 25° C.±0.1 for 24 hours equilibration time (with constant agitation). The resulting solids are collected by filtration, air-dried to remove residual excess solvent and then analyzed by X-ray powder diffraction to yield Polymorph Form $S_C$ of the monohydrochloride salt of the compound of Formula A.

Example 15

Polymorph Form $S_E$ of 5-(2,6-Di-4-morpholinyl-4-pyrimidinyl)-4-(trifluoromethyl)pyridin-2-amine monohydrochloride 40 mg of 6 of Example 5 is stirred in a solution having ethanol and water in a 1:1 ratio or a solution having acetonitrile and water in a 1:1 ratio in a vial at 25° C.±0.1 for 24 hours equilibration time (with constant agitation). The resulting solids are collected by filtration to yield Polymorph Form $S_D$ of the monohydrochloride salt of the compound of Formula A.

Example 16

Polymorph Form $S_E$ of 5-(2,6-Di-4-morpholinyl-4-pyrimidinyl)-4-(trifluoromethyl)pyridin-2-amine monohydrochloride 40 mg of 6 of Example 5 is stirred in a solution having acetone and water in a 1:1 ratio in a vial at 25° C.±0.1 for 24 hours equilibration time (with constant agitation). The resulting solids are collected by filtration to yield Polymorph Form $S_E$ of the monohydrochloride salt of the compound of Formula A.

Tables

TABLE 1

List of most significant peaks of FIG. 4
(Hemihydrate polymorph form H$_A$)

| 2-Theta in deg | Intensity in % |
|---|---|
| 7.7 | 66 |
| 9.0 | 40 |
| 10.0 | 42 |
| 11.1 | 52 |
| 12.5 | 49 |
| 13.7 | 44 |
| 15.5 | 80 |
| 16.0 | 49 |
| 16.7 | 76 |
| 17.3 | 49 |
| 18.1 | 41 |
| 18.7 | 96 |
| 19.2 | 100 |
| 19.9 | 48 |
| 20.8 | 39 |
| 21.4 | 35 |
| 22.0 | 64 |
| 22.9 | 56 |
| 23.2 | 40 |
| 24.2 | 62 |
| 24.5 | 53 |
| 25.4 | 47 |
| 27.5 | 44 |
| 27.5 | 44 |

TABLE 2

List of most significant peaks of FIG. 5
(Anhydrous polymorph form A)

| 2-Theta in degrees | Intensity in % |
|---|---|
| 7.4 | 15.3 |
| 10.2 | 93.1 |
| 10.8 | 18.6 |
| 12.0 | 19 |
| 14.8 | 100 |
| 16.5 | 16.2 |
| 17.4 | 90.1 |
| 19.3 | 20 |
| 21.1 | 33.5 |
| 21.8 | 41.8 |
| 22.3 | 13.5 |
| 23.4 | 16.9 |
| 23.9 | 23.3 |
| 24.3 | 27.1 |
| 25.0 | 13.5 |

TABLE 3

List of most significant peaks of FIG. 6
(Hydrochloride polymorph form Ha)

| 2-Theta in deg | Intensity in % |
|---|---|
| 7.2 | 31 |
| 9.3 | 100 |
| 14.5 | 12 |
| 15.8 | 96 |
| 18.6 | 47 |
| 21.2 | 15 |
| 22.2 | 15 |
| 23.7 | 18 |
| 24.7 | 14 |
| 25.8 | 16 |

TABLE 4

List of most significant peaks of FIG. 7
(Hydrochloride polymorph form A)

| 2-Theta in degrees | Intensity in % |
|---|---|
| 8.8 | 58 |
| 9.9 | 100 |
| 12.8 | 50 |
| 14.0 | 40 |
| 14.9 | 37 |
| 15.4 | 33 |
| 18.0 | 87 |
| 18.8 | 54 |
| 20.0 | 87 |
| 20.7 | 76 |
| 22.5 | 38 |
| 23.9 | 59 |
| 24.3 | 58 |
| 25.0 | 66 |
| 27.5 | 48 |
| 29.1 | 36 |
| 31.3 | 39 |

TABLE 5

List of most significant peaks of FIG. 8
(Hydrochloride polymorph form B)

| 2-Theta in degrees | Intensity in % |
|---|---|
| 8.3 | 29 |
| 11.7 | 59 |
| 12.3 | 35 |
| 14.6 | 32 |
| 16.7 | 87 |
| 17.3 | 30 |
| 18.3 | 88 |
| 18.7 | 100 |
| 19.7 | 33 |
| 20.1 | 91 |
| 21.1 | 29 |
| 21.8 | 100 |
| 23.5 | 41 |
| 23.9 | 56 |
| 24.8 | 68 |
| 25.1 | 69 |
| 26.8 | 59 |
| 29.5 | 42 |

TABLE 6

List of most significant peaks of FIG. 9
(Polymorph form S$_A$)

| 2-Theta in degrees | Intensity in % |
|---|---|
| 7.6 | 37 |
| 14.8 | 70 |
| 15.2 | 98 |
| 16.6 | 100 |
| 17.7 | 55 |
| 19.0 | 62 |
| 20.1 | 54 |
| 21.2 | 27 |
| 22.4 | 78 |
| 23.4 | 35 |
| 23.8 | 70 |
| 24.1 | 57 |
| 26.3 | 54 |
| 27.3 | 46 |
| 28.4 | 97 |
| 29.7 | 36 |
| 30.7 | 40 |

TABLE 7

List of most significant peaks of FIG. 10
(Polymorph form $S_B$)

| 2-Theta in degrees | Intensity in % |
|---|---|
| 6.6 | 31 |
| 8.2 | 31 |
| 9.6 | 19 |
| 13.2 | 21 |
| 13.8 | 22 |
| 14.8 | 28 |
| 16.3 | 21 |
| 17.2 | 31 |
| 17.5 | 51 |
| 19.2 | 23 |
| 19.8 | 100 |
| 20.4 | 19 |
| 23.5 | 39 |
| 25.1 | 19 |

TABLE 8

List of most significant peaks of FIG. 11
(Polymorph form $S_C$)

| 2-Theta in degrees | Intensity in % |
|---|---|
| 8.8 | 19 |
| 9.4 | 24 |
| 9.9 | 75 |
| 12.3 | 18 |
| 12.8 | 25 |
| 14.0 | 21 |
| 14.9 | 32 |
| 15.8 | 37 |
| 18.0 | 38 |
| 18.8 | 34 |
| 20.0 | 100 |
| 20.7 | 31 |
| 21.1 | 20 |
| 24.0 | 23 |
| 25.1 | 26 |
| 27.5 | 26 |
| 31.4 | 22 |
| 24.3 | 19 |

TABLE 9

List of most significant peaks of FIG. 12
(Polymorph form $S_D$)

| 2-Theta in deg | Intensity in % |
|---|---|
| 4.3 | 39 |
| 6.6 | 95 |
| 7.4 | 42 |
| 8.1 | 90 |
| 9.6 | 54 |
| 13.8 | 35 |
| 14.8 | 59 |
| 16.4 | 31 |
| 17.6 | 88 |
| 19.7 | 66 |
| 20.0 | 66 |
| 20.5 | 36 |
| 22.0 | 45 |
| 22.9 | 62 |
| 23.5 | 100 |
| 25.2 | 40 |
| 25.7 | 35 |

TABLE 10

List of most significant peaks of FIG. 13
(Polymorph form $S_E$)

| 2-Theta in deg | Intensity in % |
|---|---|
| 4.3 | 91 |
| 4.9 | 42 |
| 6.9 | 67 |
| 7.3 | 83 |
| 8.6 | 39 |
| 8.8 | 39 |
| 9.9 | 91 |
| 11.9 | 47 |
| 12.7 | 40 |
| 13.9 | 34 |
| 14.7 | 63 |
| 17.6 | 100 |
| 18.1 | 61 |
| 18.8 | 39 |
| 19.4 | 45 |
| 19.8 | 66 |
| 20.6 | 54 |
| 22.0 | 40 |
| 22.9 | 46 |
| 23.5 | 47 |

The invention claimed is:

1. A crystalline form of the compound of formula A

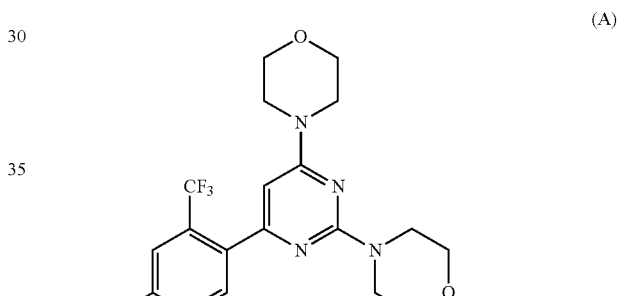

(A)

or of a hydrate or solvate of the compound of formula A, or of a salt of the compound of formula A, or of a hydrate or solvate of a salt of the compound of formula A, wherein said crystalline form is selected from the group consisting of a crystalline form of the compound of formula A in polymorph Form A anhydrous, a monohydrate of the monohydrochloride salt of the Compound of formula A in polymorph Form Ha, a monohydrochloride salt of the Compound of formula A in polymorph Form A, a monohydrochloride salt of the Compound of formula A in polymorph Form B, a solvate of the monohydrochloride salt of the Compound of formula A in polymorph Form $S_A$, a solvate of the monohydrochloride salt of the Compound of formula A in polymorph Form $S_B$, a solvate of the monohydrochloride salt of the Compound of formula A in polymorph Form $S_C$, a solvate of the monohydrochloride salt of the Compound of formula A in polymorph Form $S_D$, and a solvate of the monohydrochloride salt of the Compound of formula A in polymorph Form $S_E$.

2. A crystalline form of the compound of formula A according to claim 1 in polymorph Form A anhydrous, wherein the crystalline form of the Compound of formula A shows on X-ray diffraction a peak at an angle of diffraction 2theta of 14.8+/−0.3° and 10.2+/−0.3°.

3. A monohydrate of the monohydrochloride salt of the Compound of formula A according to claim 1 in polymorph Form Ha, wherein the monohydrate shows on X-ray diffraction a peak at an angle of diffraction 2theta of 9.3°+/−0.3° and 15.8+/−0.3°.

4. A monohydrochloride salt of the Compound of formula A according to claim 1 in polymorph Form A, wherein said monohydrochloride salt shows on X-ray diffraction a peak at an angle of diffraction 2theta of 9.9°+/−0.3° and 20.0°+/−0.3°.

5. A monohydrochloride salt of the Compound of formula A according to claim 1 in polymorph Form B, wherein said monohydrochloride salt shows on X-ray diffraction a peak at an angle of diffraction 2theta of 18.7°+/−0.3° and 21.8°+/−0.3°.

6. A solvate of the monohydrochloride salt of the Compound of formula A according to claim 1 in the form of polymorph Form $S_A$, wherein said solvate of the monohydrochloride salt of the Compound of formula A shows on X-ray diffraction a peak at an angle of diffraction 2theta of 16.6°+/−0.3° and 28.4°+/−0.3°.

7. A solvate of the monohydrochloride salt of the Compound of formula A according to claim 1 in the form of polymorph Form $S_B$, wherein said solvate of the monohydrochloride salt of the Compound of formula A shows on X-ray diffraction a peak at an angle of diffraction 2theta of 19.8°+/−0.3° and 17.5°+/−0.3°.

8. A solvate of the monohydrochloride salt of the Compound of formula A according to claim 1 the form of polymorph Form $S_C$, wherein said solvate of the monohydrochloride salt of the Compound of formula A shows on X-ray diffraction a peak at an angle of diffraction 2theta of 9.9°+/−0.3° and 20.0°+/−0.3°.

9. A solvate of the monohydrochloride salt of the Compound of formula A according to claim 1 in the form of polymorph Form $S_D$, wherein said solvate of the monohydrochloride salt of the Compound of formula A shows on X-ray diffraction a peak at an angle of diffraction 2theta of 9.9°+/−0.3° and 23.5°+/−0.3°.

10. A solvate of the monohydrochloride salt of the Compound of formula A according to claim 1 in the form of polymorph Form $S_E$, wherein said solvate of the monohydrochloride salt of the Compound of formula A shows on X-ray diffraction a peak at an angle of diffraction 2theta of 4.3°+/−0.3° and 17.6°+/−0.3°.

11. The solid form of Compound A or of a hydrate or solvate of the Compound of formula A or of a salt of the Compound of formula A, or of a hydrate or solvate of a salt of the Compound of formula A according to claim 1, which is present in essentially pure form.

12. A pharmaceutical composition comprising a crystalline form of the Compound of formula A, its hydrates or solvates, its salts and hydrates or solvates of its salts according to claim 1, and optionally at least one pharmaceutically acceptable carrier.

13. The method for the treatment of a warm-blooded animal suffering from a proliferative disorder comprising administering a therapeutically effective amount of a crystalline form of Compound A, its hydrates, its salts and hydrates or solvates of its salts according to claim 1 to said warm-blooded animal in need thereof, wherein said proliferative disease is selected from the group consisting of a benign or malignant tumor, carcinoma of the brain, kidney, liver, adrenal gland, bladder, breast, stomach, gastric tumors, ovaries, colon, rectum, prostate, pancreas, lung, vagina, thyroid, sarcoma, glioblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, lymphomas, a mammary carcinoma, a leukemia, Cowden syndrome, Lhermitte-Dudos disease and Bannayan-Zonana syndrome, and diseases in which the PI3K/PKB pathway is aberrantly activated.

* * * * *